United States Patent
Schmidlin et al.

(10) Patent No.: US 12,426,594 B2
(45) Date of Patent: Sep. 30, 2025

(54) CRYOPROTECTIVE COMPOSITIONS AND METHODS FOR PROTECTION OF A SURGICAL SITE DURING CRYOSURGERY

(71) Applicants: Everest Medical Innovation GmbH, Zug (CH); Regents of the University of Minnesota, Minneapolis, MN (US)

(72) Inventors: Franz Schmidlin, Geneva (CH); John Bischof, St. Paul, MN (US); Paul A. Iaizzo, White Bear Lake, MN (US); Qi Shao, Plymouth, MN (US); Pegah Ranjbartehrani, Falcon Heights, MN (US); David A. Ramirez, St. Paul, MN (US)

(73) Assignees: Everest Medical Innovation GmbH, Zug (CH); Regents of the University of Minnesota, Minneapolis, MN (US)

( * ) Notice: Subject to any disclaimer, the term of this patent is extended or adjusted under 35 U.S.C. 154(b) by 876 days.

(21) Appl. No.: 17/482,898

(22) Filed: Sep. 23, 2021

(65) Prior Publication Data
US 2022/0087250 A1 Mar. 24, 2022

Related U.S. Application Data

(60) Provisional application No. 63/082,790, filed on Sep. 24, 2020.

(51) Int. Cl.
*A61B 18/02* (2006.01)
*A01N 1/125* (2025.01)
*A01N 1/128* (2025.01)
*A61B 18/00* (2006.01)

(52) U.S. Cl.
CPC ............. *A01N 1/125* (2025.01); *A01N 1/128* (2025.01); *A61B 18/02* (2013.01); *A61B 2018/00547* (2013.01); *A61B 2018/00577* (2013.01); *A61B 2018/0088* (2013.01); *A61B 2018/0293* (2013.01)

(58) Field of Classification Search
CPC .... A01N 1/0221; A01N 1/0231; A61B 18/02; A61B 2018/00547; A61B 2018/00577; A61B 2018/0088; A61B 2018/0293; A61B 5/4381; A61B 5/388; A61B 2018/00839; A61B 2090/378; A61B 2505/05; A61P 9/00; A61P 41/00; A61P 13/08; A61P 43/00; A61K 9/0019; A61K 9/0014; A61K 9/06; A61K 31/10; A61K 31/7016; A61K 47/26
See application file for complete search history.

(56) References Cited

U.S. PATENT DOCUMENTS

| | | |
|---|---|---|
| 4,559,298 A | 12/1985 | Fahy |
| 4,865,871 A | 9/1989 | Livesey et al. |
| 5,071,741 A | 12/1991 | Brockbank |
| 5,131,850 A | 7/1992 | Brockbank |
| 5,158,867 A | 10/1992 | McNally et al. |
| 5,369,110 A | 11/1994 | Schmidlin et al. |
| 5,399,578 A | 3/1995 | Buhlmayer et al. |
| 5,795,711 A | 8/1998 | Mullon et al. |
| 5,958,670 A | 9/1999 | Goodrich, Jr. et al. |
| 5,965,592 A | 10/1999 | Buhlmayer et al. |
| 6,041,787 A * | 3/2000 | Rubinsky ............... A01N 1/02 606/23 |
| 6,194,136 B1 | 2/2001 | Livesey et al. |
| 6,368,784 B1 | 4/2002 | Murray |
| 6,395,467 B1 | 5/2002 | Fahy et al. |
| 6,616,858 B2 | 9/2003 | Fahy et al. |
| 6,618,858 B1 | 9/2003 | Gautier |
| 6,638,709 B2 | 10/2003 | Tai et al. |
| 6,673,607 B2 | 1/2004 | Toner et al. |
| 6,869,757 B2 | 3/2005 | Fahy |
| 6,921,633 B2 | 7/2005 | Baust et al. |
| 6,949,335 B2 | 9/2005 | Fahy et al. |
| 6,951,712 B2 | 10/2005 | Soane et al. |
| 7,094,601 B2 | 8/2006 | Toner et al. |

(Continued)

FOREIGN PATENT DOCUMENTS

| | | |
|---|---|---|
| CN | 106890193 A | 6/2017 |
| CN | 107156108 A | 9/2017 |

(Continued)

OTHER PUBLICATIONS

Shah et al., Protection of the Rectum during Prostate Radiation. Semin Intervent Radiol 2020;37:324-329 (Year: 2020).*
Schroeder et al., Trehalose as a Cryoprotective Agent for use During Prostate Cryoablation. Proc. of SPIE vol. 6842. 2008 (Year: 2008).*
Babaian et al., Best Practice Statement on Cryosurgery for the Treatment of Localized Prostate Cancer. vol. 180, 1993-2004, Nov. 2008 (Year: 2008).*
Al-Hussein et al., Investigation of the stabilizing effects of hydroxyethyl cellulose on LDH during freeze drying and freeze thawing cycles. Pharm Dev Technol, 2015; 20(1): 50-59 (Year: 2015).*

(Continued)

*Primary Examiner* — Robert A Wax
*Assistant Examiner* — Ngoc-Anh Thi Nguyen
(74) *Attorney, Agent, or Firm* — The Webb Law Firm

(57) ABSTRACT

A cryoprotective composition configured to be applied during cryotreatment of a patient includes at least one biodegradable and/or bioerodible fluid agent and at least one non-toxic cryoprotectant agent. A therapeutically effective amount of the cryoprotective composition deposited in a body space of the patient in proximity to the cryotreatment remains within at least a portion of the body space for a duration of the cryotreatment. At least a portion of a body tissue proximate to the body space is viable after the cryotreatment. A method of protecting a surgical site during prostate cryosurgery is also provided. The method includes injecting a therapeutically effective amount of the cryoprotective composition into the body space, wherein the body space is a periprostatic space of a patient.

27 Claims, 33 Drawing Sheets

(56) References Cited

U.S. PATENT DOCUMENTS

| | | | |
|---|---|---|---|
| 7,169,606 | B2 | 1/2007 | DePablo et al. |
| 7,250,292 | B2 | 7/2007 | Fahy |
| 7,270,946 | B2 | 9/2007 | Brockbank et al. |
| 7,276,359 | B1 | 10/2007 | Musunuri et al. |
| 7,344,530 | B2 | 3/2008 | Bischof et al. |
| 7,344,531 | B2 | 3/2008 | Bischof et al. |
| 7,479,139 | B2 | 1/2009 | Cytron et al. |
| 7,550,255 | B2 | 6/2009 | Fahy |
| 7,674,767 | B2 | 3/2010 | Pai et al. |
| 7,731,758 | B2 | 6/2010 | Asius et al. |
| 7,741,018 | B2 | 6/2010 | Fahy |
| 8,017,311 | B2 | 9/2011 | Brockbank et al. |
| 8,097,403 | B2 | 1/2012 | Ho et al. |
| 8,367,059 | B2 | 2/2013 | Ma |
| 8,420,307 | B2 | 4/2013 | Ostermeier et al. |
| 8,435,729 | B2 | 5/2013 | Ostermeier et al. |
| 8,440,390 | B2 | 5/2013 | Brockbank |
| 8,460,926 | B2 | 6/2013 | Yamashiro et al. |
| 8,623,591 | B2 | 1/2014 | Taylor et al. |
| 8,679,735 | B2 | 3/2014 | Fahy et al. |
| 8,685,637 | B2 | 4/2014 | Ostermeier et al. |
| 8,703,411 | B2 | 4/2014 | Chang et al. |
| 8,715,639 | B2 | 5/2014 | Suzuki et al. |
| 8,790,923 | B2 | 7/2014 | Ennis et al. |
| 9,163,210 | B2 | 10/2015 | Chung et al. |
| 9,402,388 | B2 | 8/2016 | Fong et al. |
| 9,485,984 | B2 | 11/2016 | Burbank et al. |
| 9,538,745 | B2 | 1/2017 | He et al. |
| 9,642,352 | B2 | 5/2017 | Burbank et al. |
| 9,651,508 | B2 | 5/2017 | Bischof et al. |
| 9,664,431 | B2 | 5/2017 | Mullen et al. |
| 9,848,615 | B2 | 12/2017 | Bisgaard-Frantzen et al. |
| 9,851,316 | B2 | 12/2017 | Lubner et al. |
| 9,938,495 | B2 | 4/2018 | Comhaire et al. |
| 10,006,003 | B2 | 6/2018 | Spencer et al. |
| 10,098,685 | B2 | 10/2018 | Lalonde et al. |
| 10,104,880 | B2 | 10/2018 | Zeitlin et al. |
| 10,104,881 | B2 | 10/2018 | Lee et al. |
| 10,117,822 | B2 | 11/2018 | Citernesi et al. |
| 10,292,382 | B2 | 5/2019 | Bouaita et al. |
| 10,314,302 | B2 | 6/2019 | Hubel et al. |
| 10,329,526 | B2 | 6/2019 | Salmons et al. |
| 10,602,739 | B2 | 3/2020 | Meier et al. |
| 10,611,996 | B2 | 4/2020 | Copeland |
| 10,632,182 | B2 | 4/2020 | Genin et al. |
| 10,660,688 | B2 | 5/2020 | Kalser et al. |
| 10,767,037 | B2 | 9/2020 | Maudens et al. |
| 10,806,758 | B2 | 10/2020 | De Vos et al. |
| 10,815,456 | B2 | 10/2020 | She et al. |
| 10,821,138 | B2 | 11/2020 | Borody |
| 10,881,695 | B2 | 1/2021 | Maslowski |
| 10,945,427 | B2 | 3/2021 | Nishimura et al. |
| 10,952,891 | B1 | 3/2021 | Yee et al. |
| 10,980,839 | B2 | 4/2021 | Affagard et al. |
| 11,504,322 | B2 * | 11/2022 | Garibyan ............ A61K 47/02 |
| 2001/0036665 | A1 | 11/2001 | Young et al. |
| 2002/0051963 | A1 | 5/2002 | Bronshtein |
| 2003/0031998 | A1 | 2/2003 | Kadkade |
| 2003/0054331 | A1 | 3/2003 | Fraser et al. |
| 2004/0018482 | A1 | 1/2004 | Bronshtein |
| 2004/0039381 | A1 | 2/2004 | Bischof et al. |
| 2004/0053409 | A1 | 3/2004 | Tai et al. |
| 2004/0161735 | A1 | 8/2004 | Nottle et al. |
| 2004/0247580 | A1 | 12/2004 | Chung et al. |
| 2004/0248778 | A1 | 12/2004 | Gloger et al. |
| 2005/0026133 | A1 | 2/2005 | Nakatsuji et al. |
| 2005/0048460 | A1 | 3/2005 | Crowe et al. |
| 2005/0080405 | A1 | 4/2005 | Bischof et al. |
| 2005/0153272 | A1 | 7/2005 | Fahy |
| 2005/0250088 | A1 | 11/2005 | Boldt |
| 2006/0024360 | A1 | 2/2006 | Chen |
| 2006/0024657 | A1 | 2/2006 | Fahy et al. |
| 2006/0078538 | A1 | 4/2006 | Bischof et al. |
| 2006/0122588 | A1 | 6/2006 | Bischof et al. |
| 2006/0134069 | A1 | 6/2006 | Crowe et al. |
| 2006/0204484 | A1 | 9/2006 | Bisgaard-Frantzen et al. |
| 2006/0223050 | A1 | 10/2006 | Crowe et al. |
| 2006/0240399 | A1 | 10/2006 | Bronshtein |
| 2006/0252026 | A1 | 11/2006 | Tervit et al. |
| 2007/0042337 | A1 | 2/2007 | Rubinsky et al. |
| 2007/0167776 | A1 | 7/2007 | Kochavi et al. |
| 2007/0212674 | A1 | 9/2007 | Spiers |
| 2008/0050815 | A1 | 2/2008 | Sher et al. |
| 2008/0081366 | A1 | 4/2008 | Musunuri et al. |
| 2008/0114348 | A1 * | 5/2008 | Vancelette ............ A61B 18/02 606/23 |
| 2009/0041727 | A1 | 2/2009 | Suzuki et al. |
| 2009/0093054 | A1 | 4/2009 | Sjogren et al. |
| 2009/0170059 | A1 | 7/2009 | Klingemann |
| 2011/0020307 | A1 | 1/2011 | Suzuki et al. |
| 2011/0045524 | A1 | 2/2011 | Callahan et al. |
| 2011/0159585 | A1 | 6/2011 | Frey et al. |
| 2011/0200708 | A1 | 8/2011 | Orme et al. |
| 2012/0077181 | A1 | 3/2012 | Schmidt et al. |
| 2012/0077271 | A1 | 3/2012 | Collins |
| 2012/0135017 | A1 | 5/2012 | Harel et al. |
| 2012/0149108 | A1 | 6/2012 | Tanabe et al. |
| 2012/0219940 | A1 | 8/2012 | Moragas et al. |
| 2012/0251999 | A1 | 10/2012 | Demirci et al. |
| 2012/0276581 | A1 | 11/2012 | Arav et al. |
| 2012/0308660 | A1 | 12/2012 | Patel et al. |
| 2013/0059381 | A1 | 3/2013 | Mo et al. |
| 2013/0062569 | A1 | 3/2013 | Mo et al. |
| 2013/0230494 | A1 | 9/2013 | Simon |
| 2013/0236930 | A1 | 9/2013 | Leung et al. |
| 2013/0236960 | A1 | 9/2013 | Kunitomi et al. |
| 2013/0260459 | A1 | 10/2013 | Coleman et al. |
| 2013/0267008 | A1 | 10/2013 | Shon et al. |
| 2014/0356948 | A1 | 12/2014 | Jeon et al. |
| 2015/0110759 | A1 | 4/2015 | Suzuki et al. |
| 2015/0111247 | A1 | 4/2015 | Chung et al. |
| 2015/0127294 | A1 | 5/2015 | Lubner et al. |
| 2015/0216816 | A1 | 8/2015 | O'Neil et al. |
| 2015/0313211 | A1 | 11/2015 | Ng et al. |
| 2015/0320473 | A1 | 11/2015 | Kalser et al. |
| 2016/0015025 | A1 | 1/2016 | Bischof et al. |
| 2016/0021873 | A1 | 1/2016 | Akuta et al. |
| 2016/0051722 | A1 | 2/2016 | Lee et al. |
| 2016/0066563 | A1 | 3/2016 | Moscatello |
| 2016/0130606 | A1 | 5/2016 | Buschmann et al. |
| 2016/0184364 | A1 | 6/2016 | Gupta et al. |
| 2017/0166868 | A1 | 6/2017 | Coleman et al. |
| 2017/0234817 | A1 | 8/2017 | Bischof et al. |
| 2017/0266660 | A1 | 9/2017 | Anchan et al. |
| 2018/0077922 | A1 | 3/2018 | Basford et al. |
| 2018/0128827 | A1 | 5/2018 | Bischof et al. |
| 2018/0133006 | A1 | 5/2018 | Jones et al. |
| 2018/0153155 | A1 | 6/2018 | Ohashi et al. |
| 2018/0187150 | A1 | 7/2018 | De Larichaudy |
| 2018/0192639 | A1 | 7/2018 | Brockbank et al. |
| 2018/0295834 | A1 | 10/2018 | Reid et al. |
| 2018/0325957 | A1 | 11/2018 | Kastrup et al. |
| 2019/0000070 | A1 | 1/2019 | De Larichaudy |
| 2019/0008572 | A1 | 1/2019 | Lalonde et al. |
| 2019/0037831 | A1 | 2/2019 | Hwang et al. |
| 2019/0090475 | A1 | 3/2019 | Wu et al. |
| 2019/0098891 | A1 | 4/2019 | Eroglu |
| 2019/0099449 | A1 | 4/2019 | Galipeau et al. |
| 2019/0105094 | A1 | 4/2019 | Azarin et al. |
| 2019/0116783 | A1 | 4/2019 | Bischof et al. |
| 2019/0177683 | A1 | 6/2019 | Lin et al. |
| 2019/0208769 | A1 | 7/2019 | Tokle et al. |
| 2019/0216078 | A1 | 7/2019 | Morales Ueno et al. |
| 2019/0274299 | A1 | 9/2019 | Guo et al. |
| 2019/0307118 | A1 | 10/2019 | Connan et al. |
| 2019/0313632 | A1 | 10/2019 | Han et al. |
| 2019/0321334 | A1 | 10/2019 | Horn |
| 2019/0357525 | A1 | 11/2019 | Wang et al. |
| 2019/0365948 | A1 | 12/2019 | Deegan et al. |
| 2019/0380330 | A1 | 12/2019 | Buntru et al. |
| 2020/0022361 | A1 | 1/2020 | Wu et al. |
| 2020/0046771 | A1 | 2/2020 | Kuhn et al. |
| 2020/0077643 | A1 | 3/2020 | Nishimura et al. |
| 2020/0146280 | A1 | 5/2020 | Silverman et al. |

(56) References Cited

U.S. PATENT DOCUMENTS

| | | |
|---|---|---|
| 2020/0170000 A1 | 5/2020 | Hang et al. |
| 2020/0224154 A1 | 7/2020 | Garrison |
| 2020/0229425 A1 | 7/2020 | Kilbride et al. |
| 2020/0229427 A1 | 7/2020 | Kilbride et al. |
| 2020/0254027 A1 | 8/2020 | Dixit |
| 2020/0325439 A1 | 10/2020 | Chung |
| 2020/0325448 A1 | 10/2020 | Minami |
| 2020/0345000 A1 | 11/2020 | Jones et al. |
| 2020/0345055 A1 | 11/2020 | Frese |
| 2020/0383317 A1 | 12/2020 | Zacharias et al. |
| 2020/0405776 A1 | 12/2020 | Schwintner et al. |
| 2021/0007984 A1 | 1/2021 | Inacio et al. |
| 2021/0008191 A1 | 1/2021 | Conlan et al. |
| 2021/0030688 A1 | 2/2021 | Ganey et al. |
| 2021/0127663 A1 | 5/2021 | Paukkonen et al. |
| 2021/0169069 A1 | 6/2021 | Nagamura et al. |
| 2021/0186007 A1 | 6/2021 | Sanchez Gutierrez et al. |
| 2021/0195891 A1 | 7/2021 | Uygun et al. |
| 2021/0207088 A1 | 7/2021 | Koizumi et al. |
| 2021/0220411 A1 | 7/2021 | Farquhar et al. |

FOREIGN PATENT DOCUMENTS

| | | |
|---|---|---|
| CN | 107787959 A | 3/2018 |
| CN | 110115265 A | 8/2019 |
| EP | 0443983 A1 | 8/1991 |
| EP | 0564786 A2 | 10/1993 |
| EP | 1181865 A1 | 2/2002 |
| EP | 1326492 B1 | 5/2004 |
| EP | 1514553 A1 | 3/2005 |
| EP | 2434873 B1 | 7/2013 |
| EP | 2810052 B1 | 12/2017 |
| EP | 3321666 A1 | 5/2018 |
| EP | 3342288 A1 | 7/2018 |
| EP | 3403502 A1 | 11/2018 |
| EP | 3062721 B1 | 3/2019 |
| EP | 3839039 A1 | 6/2021 |
| KR | 101954120 B1 | 3/2019 |
| WO | 9221234 A1 | 12/1992 |
| WO | 9745010 A1 | 12/1997 |
| WO | 9814058 A1 | 4/1998 |
| WO | 9841156 A1 | 9/1998 |
| WO | 9931977 A1 | 7/1999 |
| WO | 0030441 A1 | 6/2000 |
| WO | 03046162 A2 | 6/2003 |
| WO | 03105672 A2 | 12/2003 |
| WO | 2004000103 A2 | 12/2003 |
| WO | 2004052098 A1 | 6/2004 |
| WO | 2004084629 A1 | 10/2004 |
| WO | 2004088233 A2 | 10/2004 |
| WO | 2004106501 A1 | 12/2004 |
| WO | 2005045007 A1 | 5/2005 |
| WO | 2006000425 A2 | 1/2006 |
| WO | 2007009285 A1 | 1/2007 |
| WO | 2010141317 A1 | 12/2010 |
| WO | 2011069587 A1 | 6/2011 |
| WO | 2012054892 A1 | 4/2012 |
| WO | 2012123606 A1 | 9/2012 |
| WO | 2013041542 A1 | 3/2013 |
| WO | 2013096659 A1 | 6/2013 |
| WO | 2013116333 A2 | 8/2013 |
| WO | 2014112675 A1 | 7/2014 |
| WO | 2014143961 A1 | 9/2014 |
| WO | 2015007773 A1 | 1/2015 |
| WO | 2015061883 A1 | 5/2015 |
| WO | 2015171142 A1 | 11/2015 |
| WO | 2016033380 A1 | 3/2016 |
| WO | 2016063208 A1 | 4/2016 |
| WO | 2017143162 A1 | 8/2017 |
| WO | 2017184721 A1 | 10/2017 |
| WO | 2017195179 A1 | 11/2017 |
| WO | 2018106844 A1 | 6/2018 |
| WO | 2018211454 A2 | 11/2018 |
| WO | 2019099922 A1 | 5/2019 |
| WO | 2019102172 A1 | 5/2019 |
| WO | 2019126270 A1 | 6/2019 |
| WO | 2019135779 A1 | 7/2019 |
| WO | 2019165910 A1 | 9/2019 |
| WO | 2019172112 A1 | 9/2019 |
| WO | 2020006150 A1 | 1/2020 |
| WO | 2020014245 A1 | 1/2020 |
| WO | 2020023387 A1 | 1/2020 |
| WO | 2020037416 A1 | 2/2020 |
| WO | 2020161273 A1 | 8/2020 |
| WO | 2020186206 A1 | 9/2020 |
| WO | 2020207151 A1 | 10/2020 |
| WO | 2020207152 A1 | 10/2020 |
| WO | 2020223125 A1 | 11/2020 |
| WO | 2021012763 A1 | 1/2021 |
| WO | 2021025719 A1 | 2/2021 |
| WO | 2021040544 A1 | 3/2021 |
| WO | 2021040545 A1 | 3/2021 |
| WO | 2021050896 A1 | 3/2021 |
| WO | 2021129560 A1 | 7/2021 |

OTHER PUBLICATIONS

Gurruchaga et al., Low molecular-weight hyaluronan as a cryoprotectant for the storage of microencapsulated cells. International Journal of Pharmaceutics 548 (2018) 206-216 (Year: 2018).*
Sams, "the Effects of Dimethyl Sulfoxide on Nerve Conduction", Annals of the New York Academy of Sciences, 1967, pp. 242-247.
Schroeder et al., "Trehalose as a cryoprotective agent for use during prostate cryoablation", Proceedings of SPIE, Feb. 2008, pp. 1-9, vol. 6842.
Shepherd et al., "PD23-10 Salvage Cryoablation of Prostate With Transperineal Denonvilliers' Space Expansion With Spaceoar: Post-operative Outcomes", The Journal of Urology, May 2019, p. e397, vol. 201:4S.
Sievert et al., "Extended periprostatic nerve distributions on the prostate surface confirmed using diffusion tensor Imaging", BJU International, 2019, pp. 995-1004, vol. 123.
"Sodium Hyaluronate", Lifecore Biomedical, Jan. 2019, https://web.archive.org/web/20190129052259/https://www.lifecore.com/sodium-hyaluronate/.
Stakenborg et al., "Comparison between the cervical and abdominal vagus nerves in mice, pigs, and humans", Neurogastroenterology & Motility, 2020, pp. 1-8, vol. 32.
"Super Cool X-1000™", 21st Century Medicine, Mar. 2019, pp. 1-2, https://web.archive.org/web/20190329171720/https://www.21cm.com/x1000.html.
"Super Cool Z-1000™", 21st Century Medicine, Aug. 2019, pp. 1-2, https://web.archive.org/web/20190825193058/http://www.21cm.com/z1000.html.
Sze et al., "Biotechnological production of hyaluronic acid: a mini review", Biotech, 2016, pp. 1-9, vol. 6:67.
"Thickening agent", Wikipedia, Jan. 2019, https://web.archive.org/web/20190129150919/https://en.wikipedia.org/wiki/Thickening_agent.
Trumble et al., "The Effects of Cryosurgery and Cryoprotectants on Peripheral Nerve Function", Journal of Reconstructive Microsurgery, Jan. 1992, pp. 53-58.
Ward et al., "Focal cryotherapy for localized prostate cancer: a report from the national Cryo On-Line Database (COLD) Registry", BJU International, 2011, pp. 1648-1654, vol. 109.
Witzsch et al., "Cryoablation of prostate cancer", Der Urologe, Feb. 2015, pp. 191-201, vol. 54. [English-language Abstract].
Zhou et al., "The incidence proportion of erectile dysfunction in patients treated with cryotherapy for prostate cancer: a meta-analysis", Clinical and Translational Oncology, 2019, pp. 1152-1158, vol. 21.
"3D Slicer", Slicer Solutions, Jul. 2020, https://web.archive.org/web/20200709213929/https://www.slicer.org/.
"AQUASONIC® 100: Ultrasound Transmission Gel", Parker Laboratories, May 2019, https://web.archive.org/web/20190525163929/https://www.parkerlabs.com/aquasonic-100.asp.
"Award Abstract #1941543: NSF Engineering Research Center for Advanced Technologies for Preservation of Biological Systems (ATP-Bio)", National Science Foundation, Aug. 2020, pp. 1-3,

(56) References Cited

OTHER PUBLICATIONS https://web.archive.org/web/20200810012512/https://nsf.gov/awardsearch/showAward?AWD_ID=1941543.

Barret et al., "Morbidity of Focal Therapy in the Treatment of Localized Prostate Cancer", European Urology, 2013, pp. 618-622, vol. 63.

Baust et al., "Cryoablation of Prostate—Improving Efficacy and Safety", Medical Research Archives, May 2020, pp. 1-14, vol. 8:5.

Baust et al., "Investigation of neuronal cell stress response to transient freezing associated with cryosurgical ablation of the prostate", Cryobiology, 2010, pp. 364, vol. 61.

Belavy et al., "Absence of neurotoxicity with perineural injection of ultrasound gels: assessment using an animal model", BMC Anesthesiology, 2013, pp. 1-6, vol. 13:18.

Bischof et al., "Use of X-ray Tomography to Map Crystalline and Amorphous Phases in Frozen Biomaterials", Annals of Biomedical Engineering, Feb. 2007, pp. 292-304, vol. 35:2.

Burt et al., "Factors influencing prostate cancer patterns of care: An analysis of treatment variation using the SEER database", Advances in Radiation Oncology, 2018, pp. 170-180, vol. 3.

"Cancer Stat Facts: Prostate Cancer", National Cancer Institute: Surveillance, Epidemiology, and End Results Program, Jul. 2020, pp. 1-15, https://web.archive.org/web/20200729225031/https://seer.cancer.gov/statfacts/html/prost.html.

Charny, "Mathematical Models of Bioheat Transfer", Advances in Heat Transfer, 1992, pp. 19-155, vol. 22.

De Wolf, "Vitrification Agents In Cryonics: M22", Biostasis, Jul. 2008, pp. 1-10, https://www.biostasis.com/vitrification-agents-in-cryonics-m22/.

Dibaj et al., "In Vivo Recording of Nerve Conduction Velocity of Spinal CNS Fibers in the Mouse", Physiol. Res., 2017, pp. 545-548, vol. 66.

Ding et al., "Anatomical anomalies of the laryngeal branches of the vagus nerve in pigs (*Sus scrofa*)", Laboratory Animals, 2012, pp. 338-340, vol. 46.

Elliot et al., "Cryoprotectants: A review of the actions and applications of cryoprotective solutes that modulate cell recovery from ultra-low temperatures", Cryobiology, 2017, pp. 74-91, vol. 76.

"Endocare ™ Precision Cryoprobes", HealthTronics, 2017, pp. 1-2.

Etheridge et al., "Methods for Characterizing Convective Cryoprobe Heat Transfer in Ultrasound Gel Phantoms", Journal of Biomechanical Engineering, Feb. 2013, pp. 1-10, vol. 135.

"Experimental preparation", McGill Physiology Virtual Lab, Sep. 2019, https://web.archive.org/web/20190906022311/http://www.medicine.mcgill.ca/physio/vlab/CAP/prep.htm.

Fu et al., "The Cellular and Molecular Basis of Peripheral Nerve Regeneration," Molecular Neurobiology, 1997, pp. 67-116, vol. 14.

Gage et al., "Cryosurgery—a Review of Recent Advances and Current Issues", CryoLetters, 2002, pp. 69-78, vol. 23.

Galvao et al., "Unexpected low-dose toxicity of the universal solvent DMSO", The FASEB Journal, 2014, pp. 1317-1330, vol. 28.

Ganzer et al., "Topographical Anatomy of Periprostatic and Capsular Nerves: Quantification and Computerised Planimetry", European Urology, 2008, pp. 353-361, vol. 54.

Gao et al., "Preparation of Scalable Silica-Coated Iron Oxide Nanoparticles for Nanowarming", Adv. Sci., 2020, pp. 1-12, vol. 7.

Goff et al., "In vitro assessment of induced phrenic nerve cryothermal injury", Heart Rhythm, 2014, pp. 1779-1784, vol. 11.

Guillaumier et al., "A Multicentre Study of 5-year Outcomes Following Focal Therapy in Treating Clinically Significant Nonmetastatic Prostate Cancer", European Urology, 2018, pp. 422-429, vol. 74.

Hatiboglu et al., "Application technique: placement of a prostate-rectum spacer in men undergoing prostate radiation therapy", BJU International, 2012, pp. E647-E652, vol. 110.

"How Does SpaceOAR™ Hydrogel Work?", Boston Scientific, Aug. 2020, pp. 1-10, https://web.archive.org/web/20200812143950/https://www.spaceoar.com/about-spaceoar-hydrogel/how-spaceoar-hydrogel-works/.

Hubbard et al., "Cryosurgery for the Treatment of Localized Prostate Cancer", American Urological Association Education and Research, Inc., 2008, pp. 1-51.

Janzen et al., "Feasibility of Nerve-Sparing Prostate Cryosurgery: Applications and Limitations in a Canine Model", Journal of Endourology, May 2005, pp. 520-525, vol. 19:4.

Kasivisvanathan et al., "Focal Therapy for Prostate Cancer: Rationale and Treatment Opportunities", Clinical Oncology, 2013, pp. 461-473, vol. 25.

Lenz et al., "The Freezing Threshold of the Peripheral Motor Nerve: An Electrophysiological and Light-Microscopical Study on the Sciatic Nerve of the Rabbit", Cryobiology, 1975, pp. 486-496, vol. 12.

Levy et al., "Definition of Biochemical Success Following Primary Whole Gland Prostate Cryoablation", The Journal of Jrology, Nov. 2014, pp. 1380-1384, vol. 192.

Liu et al., "Ultrasound-Enhanced Drug Transport and Distribution in the Brain", AAPS PharmSciTech, Sep. 2010, pp. 1005-1017, vol. 11:3.

Manuchehrabadi et al., "Improved Tissue Cryopreservation using Inductive Heating of Magnetic Nanoparticles", Sci. Transl. Med., 2017, Mar. 2001, pp. 1-24, vol. 9:379.

Martin et al., "Multipoint Thermal Sensors Associated with Improved Oncologic Outcomes Following Cryoablation", Journal of Endourology, Apr. 2017, pp. 355-360, vol. 31:4.

Menz, "Effect of Cryoprotective Agents on Rat Cutaneous Nerves", Cryobiology, 1975, pp. 405-416, vol. 12.

Mouraviev et al., "Contemporary Results of Focal Therapy for Prostate Cancer Using Cryoablation", Journal of Endourology, May 2010, pp. 827-834, vol. 24:5.

Mouraviev et al., "Update on cryotherapy for prostate cancer in 2006", Current Opinion in Urology, 2006, pp. 152-156, vol. 16.

Mukherjee et al., "Cryoprotectant transport through articular cartilage for long-term storage: experimental and modeling studies", Osteoarthritis and Cartilage, 2008, pp. 1379-1386, vol. 16.

Onik et al., "Focal "Nerve-Sparing" Cryosurgery for Treatment of Primary Prostate Cancer: a New Approach To Preserving Potency", Urology, 2002, pp. 109-114, vol. 60.

Pei et al., "An electroneurography-based assay for identifying injured nerve segment during surgery: design and in vivo application in the rat", Journal of Neural Engineering, 2019, pp. 1-9, vol. 16.

Pelot et al., "Quantified Morphology of the Cervical and Subdiaphragmatic Vagus Nerves of Human, Pig, and Rat", Frontiers in Neuroscience, 2020, pp. 1-19, vol. 14.

Polascik et al., "Nerve-sparing focal cryoablation of prostate cancer", Current Opinion in Urology, 2009, pp. 182-187, vol. 19.

Poltawski et al., "Relative transmissivity of ultrasound coupling agents commonly used by therapists in the UK", US couplant transmissivity, 2007, pp. 1-13.

Porto et al., "The addition of albumin improves Schwann cells viability in nerve cryopreservation", Cell Tissue Bank, 2018, pp. 507-517, vol. 19.

Prepellca et al., "Cryosurgical Ablation of the Prostate: High-Risk Patient Outcomes", Cancer, Apr. 2005, pp. 1625-1630, vol. 103.

Rabin et al., "The thermal effect of urethral warming during cryosurgery", CryoLetters, 2002, pp. 361-374, vol. 23.

Resnick et al., "Long-Term Functional Outcomes after Treatment for Localized Prostate Cancer", The New England Journal of Medicine, 2013, pp. 436-445, vol. 368.

Robinson et al., "Quality of Life and Sexuality of Men With Prostate Cancer 3 Years After Cryosurgery", Urology, 2002, pp. 12-18, vol. 60.

Rubinsky et al., "a Finite Element Method for the Solution of One-Dimensional Phase Change Problems", International Journal of Heat and Mass Transfer, 1981, pp. 1987-1989, vol. 24:12.

Katarina Antolic, et al, (2019) Cryocornea-toward Enhancing the capacity and throughout of ex vivo corneal model, Drug Development and Industrial Pharmacy, 45:12, 1856-1861, DOI: 10.1080/03639045.2019.1672713.

(56) References Cited

OTHER PUBLICATIONS

T. Schroeder, et al., Trehalose as a Cryoprotective Agent for Use During Prostrate Cryoablation, American Medical Systems, Inc., 2008 SPIE Digital Library, Proc. of SPIE vol. 6842 68420U-1-8.

* cited by examiner

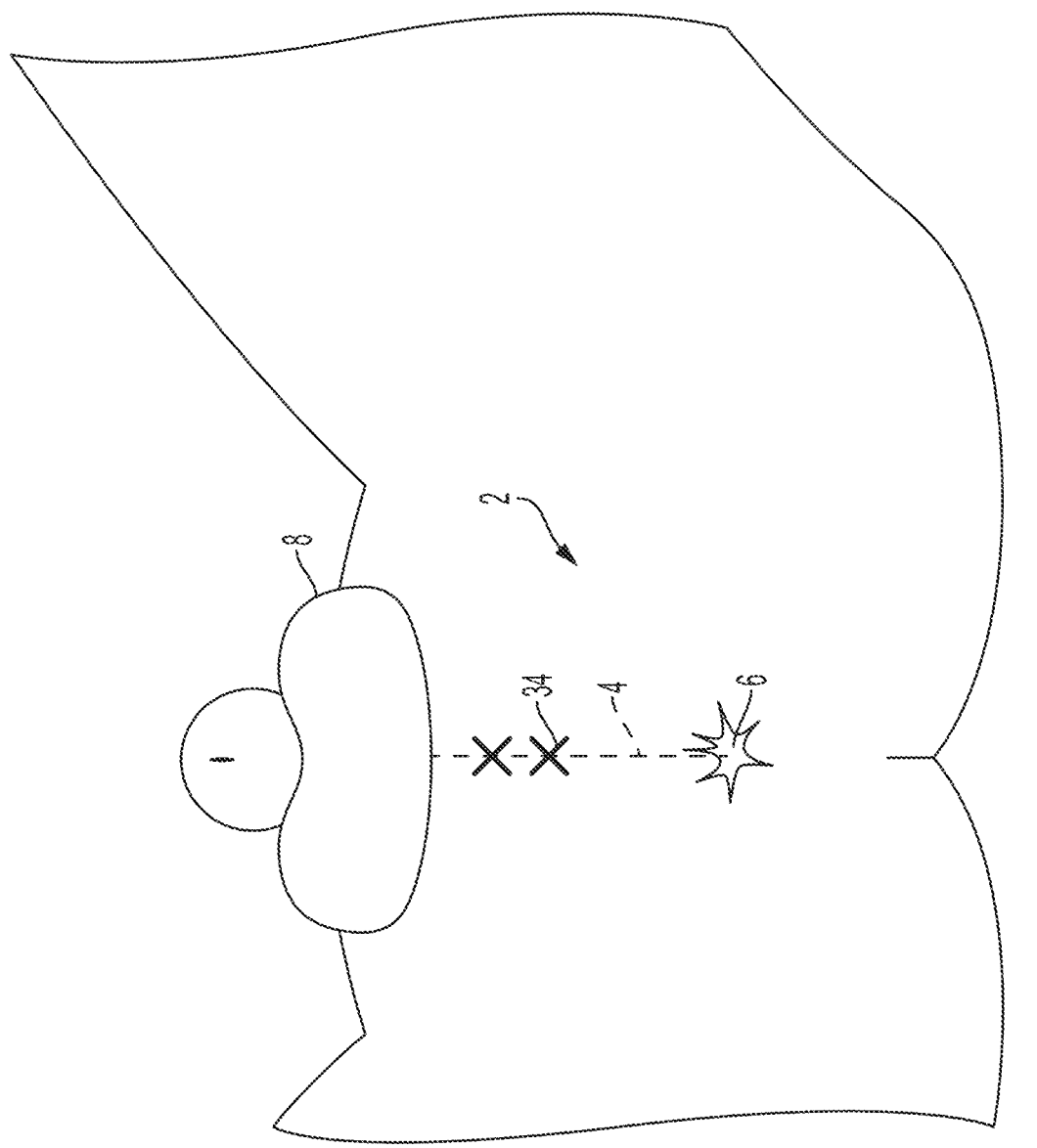

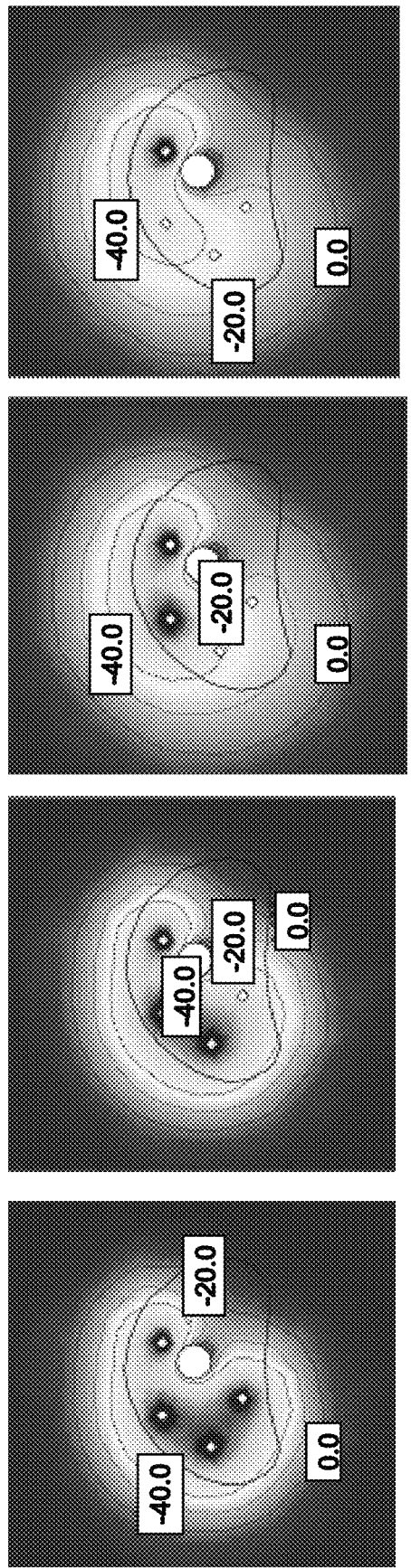

CRYOPROTECTIVE COMPOSITIONS AND METHODS FOR PROTECTION OF A SURGICAL SITE DURING CRYOSURGERY

CROSS REFERENCE TO RELATED APPLICATION

The present application claims the benefit of U.S. Provisional Patent Application No. 63/082,790, filed Sep. 24, 2020, the disclosure of which is hereby incorporated by reference in its entirety.

BACKGROUND

Technical Field

The present disclosure relates to cryoprotective compositions comprising cryoprotectant agents (CPAs) of low toxicity and sufficient viscosity to remain within body spaces, for example surrounding organs and nerve structures, for sufficient duration for performing certain treatments or cryosurgical procedures. Also included are cryoprotective compositions for protecting internal and/or external body tissues or organs of patients or plants from exposure to cold temperatures that may result in damage to body tissue, organs, or to surfaces of plants exposed to frost and/or freezing temperatures.

Background

Prostate cancer is the second-most common cancer among men (after skin cancer) and the second leading cause of cancer death for men in the United States and most Western European countries. Prostate cancer can often be treated successfully. However, many of the current treatment options and procedures have associated risks and common complications that affect quality of life of survivors following treatment. Radical therapy (e.g., radical prostatectomy and radiotherapy) has been shown to have excellent outcomes in terms of prostate cancer specific survival for localized prostate cancer. However, such procedures can have undesirable side effects, such as urinary incontinence or erectile dysfunction.

Cryoablation has been shown to be an effective therapy for all stages of prostate cancer, serving as both a primary treatment option and a salvage treatment option. Minimally invasive cryoablation therapy has similar 5 year and 10 year outcomes for low and intermediate risk prostate cancer (D'Amico risk classification). Minimally invasive cryoablation therapy also has encouraging outcomes for high risk prostate cancer compared to other therapies, including radical prostatectomy, radiation (conformal and external beam), and brachytherapy. In recent decades, technological advancements for prostate cryosurgery have been focused on improving the efficacy of targeted freezing and protection of the adjacent extra-prostatic tissues.

Despite such advances, a major complication of cryotherapy continues to be the injury to adjacent normal tissues, which can cause erectile dysfunction. In cryotherapy treatment of prostate cancer, for example, a significant side effect is injury to the neurovascular bundle, which contributes to erectile dysfunction, because these nerves can be directly exposed to lethal levels of cold temperature during cryotherapy. This detrimental side effect is extremely common because injury to these nerves occurs in 80% to 90% of performed procedures in the case of whole gland treatment. In focal prostate cryotherapy, the incidence is lower with 40%. This high incident rate of injury to these nerves is due to the close proximity of the neurovascular bundle to the prostate. While a significant number of patients may experience full or partial recovery within about twelve months following therapy, some patients are left to seek alternative therapies aimed at restoration of potency.

Efforts have been made to spare the neurovascular bundle and increase quality of life for patients by, for example, active heating of tissues in proximity to the treatment area and focal cryotherapy under image guidance. However, such approaches may suffer from a lack of precision in positioning and/or an increase in the possibility of cancer reoccurrence.

Active heating by placement of a heated needle to the surgical site creates a "divot" of warming to counteract effects of tissue freezing. However, challenges of this procedure relating to probe placement and lack of precision in temperature control reduce reliability of this procedure, which has not been widely accepted.

For focal therapy, only a quadrant or section of the prostate that contains the cancer is treated. Focal cryotherapy was developed to minimize injuries to adjacent structures, such as the urethral sphincter, rectum, and nerve tissues, thereby reducing the risk of urinary incontinence, rectal injury, and to help preserve erectile function. However, focal cryotherapy has succeeded only in exchange for an increase in the possibility of cancer reoccurrence. Moreover, focal cryotherapy is reserved for a select group of patients whose probability of cancer reoccurrence in another section of the prostate is minimal.

In view of these challenges, there is a need in the art for cryoprotective composition(s) and surgical method(s) that provide sufficient protection for the entire periprostatic space, while allowing for treatment of the prostate without risks and complications often associated with cryotherapies. Also, cryosurgical method(s) are needed to reduce instances of cancer reoccurrence, which can occur from focal therapy.

More generally, there is a need in the art for cryoprotective composition(s) for use within the body and/or externally to protect body tissue from the effects of cold temperatures. Also, there is a need in the art for cryoprotective composition(s) for use with plants to protect the plants from the effects of cold temperatures.

SUMMARY

According to an example of the disclosure, a cryoprotective composition configured to be applied during cryotreatment of a patient includes at least one biodegradable and/or bioerodible fluid agent and at least one non-toxic cryoprotectant agent. A therapeutically effective amount of the cryoprotective composition deposited in a body space of the patient in proximity to the cryotreatment remains within at least a portion of the body space for a duration of the cryotreatment. At least a portion of a body tissue proximate to the body space is viable after the cryotreatment.

According to another example of the disclosure, a method of protecting a surgical site during prostate cryosurgery includes injecting a therapeutically effective amount of the previously described cryoprotective composition into the body space, wherein the body space is a periprostatic space of a patient.

According to another example of the disclosure, a surgical method for destruction of a solid mass includes: injecting any of the previously described cryoprotective compositions into the body space of the patient, which is adjacent to the solid mass, and performing a cryosurgical procedure for removal and/or destruction of the solid mass while the cryoprotective composition is positioned in the space adjacent to the solid mass.

According to another example of the disclosure, a surgical method for use during neurosurgery includes: injecting any of the previously described cryoprotective compositions into the body space of the patient, wherein the body space includes spaces adjacent to the spine and/or brain; and performing a cryosurgical procedure for treatment of neurological conditions while the cryoprotective composition is positioned in the spaces adjacent to the spine and/or brain.

According to another example of the disclosure, a cryosurgical method for treating one or more of cardiac arrhythmia, ablation of aberrant nerves in proximity to a pulmonary artery, tumor(s) and/or lesions around an eye or eye orbit, esophageal tumor(s) and/or cancer, pancreatitis, pancreatic tumor(s) and/or cancer, rectal proctitis, liver tumor(s) and/or cancer, brain tumor(s) and/or cancer, cryolipolysis, chronic pain caused by trigeminal neuralgia, and/or organ transplantation is provided. The method includes injecting any of the previously described cryoprotective compositions into the body space of the patient, wherein the body space includes spaces adjacent to organs and/or body tissues to be treated by at least one cryosurgical procedure. The method also includes performing the at least one cryosurgical procedure while the cryoprotective composition is positioned in the spaces adjacent to the organs and/or body tissues to be treated.

According to another example of the disclosure, a topical protective composition configured to be applied to skin includes: at least one biodegradable and/or bioerodible fluid agent; and at least one non-toxic cryoprotectant agent. The protective composition is configured to protect the skin from damage caused by environmental conditions. The composition does not cause substantial damage to the skin.

According to another example of the disclosure, a cryoprotective composition for use in cryosurgery includes: at least one biodegradable and/or bioerodible fluid agent comprising a gel of from about 1 weight percent to about 10 weight percent of the composition; and at least one non-toxic cryoprotectant agent. The cryoprotective composition does not cause substantial nerve damage when positioned in a body space for a duration of a cryosurgical procedure.

According to another example of the present disclosure, a composition for protecting plants from frost and/or freezing includes at least one biodegradable and/or bioerodible fluid agent and at least one non-toxic cryoprotectant agent. The protective composition is configured to protect portions of a plant from damage caused by frost and/or freezing. The composition does not cause substantial damage to the plant.

According to another example of the disclosure, a method for protecting a plant from frost and/or freezing includes coating at least a portion of a surface of the plant with the previously described composition for protecting plants from frost and/or freezing.

Non-limiting examples of the present invention will now be described in the following numbered clauses:

Clause 1: A cryoprotective composition configured to be applied during cryotreatment of a patient, the composition comprising: at least one biodegradable and/or bioerodible fluid agent; and at least one non-toxic cryoprotectant agent, wherein a therapeutically effective amount of the cryoprotective composition deposited in a body space of the patient in proximity to the cryotreatment remains within at least a portion of the body space for a duration of the cryotreatment, and wherein at least a portion of a body tissue proximate to the body space is viable after the cryotreatment.

Clause 2: The cryoprotective composition of clause 1, wherein the cryotreatment of the patient comprises a cryosurgical procedure.

Clause 3: The cryoprotective composition of clause 1 or clause 2, wherein the at least one fluid agent comprises a gel, the gel comprising from about 1 weight percent to about 10 weight percent of the cryoprotective composition.

Clause 4: The cryoprotective composition of any of clauses 1-3, wherein the at least one non-toxic cryoprotectant agent comprises from about 1 weight percent to about 10 weight percent of the cryoprotective composition.

Clause 5: The cryoprotective composition of any of clauses 1-4, wherein the at least one non-toxic cryoprotectant agent comprises Dimethyl sulfoxide (DMSO) comprising from about 1 weight percent to about 5 weight percent of the cryoprotective composition.

Clause 6: The cryoprotective composition of any of clauses 1-5, wherein the at least one non-toxic cryoprotectant agent is free of Dimethyl sulfoxide (DMSO) or ethylene glycol.

Clause 7: The cryoprotective composition of any of clauses 1-6, wherein the at least one non-toxic cryoprotectant agent comprises at least one of alcohol(s), saccharide(s), polysaccharide(s), polymer(s), sulfoxide(s), amide(s), or amine(s).

Clause 8: The cryoprotective composition of any of clauses 1-7, wherein the at least one non-toxic cryoprotectant agent comprises trehalose.

Clause 9: The cryoprotective composition of any of clauses 1-8, wherein the at least one non-toxic cryoprotectant agent comprises propylene glycol.

Clause 10: The cryoprotective composition of any of clauses 1-9, wherein the duration sufficient for performing the cryosurgical procedure ranges from about 10 minutes to about 5 hours.

Clause 11: The cryoprotective composition of any of clauses 1-10, wherein the at least one non-toxic cryoprotectant agent causes less than about a 30% decrease of viability compared to saline and/or causes less than a 30% decrease of action potential amplitude compared to Krebs solution.

Clause 12: The cryoprotectant composition of any of clauses 1-11, wherein the cryoprotective composition does not cause substantial nerve damage when positioned in the body space for the duration of the cryotreatment.

Clause 13: The cryoprotective composition of any of clauses 1-12, wherein the cryoprotective composition inhibits freezing and/or crystallization of the body tissue proximate to the body space when cryotherapy agents are used for the cryosurgical procedure.

Clause 14: The cryoprotective composition of any of clauses 1-13, wherein the therapeutically effective amount of the cryoprotective composition comprises an amount of the cryoprotective composition sufficient to inhibit freezing and/or crystallization of the body tissue proximate to the body space when cryotherapy agents are used for the cryosurgical procedure.

Clause 15: The cryoprotective composition of any of clauses 1-14, wherein, when applied to a neurovascular bundle of the patient, the cryoprotective composition does not substantially inhibit generation of action potentials by nerves of the neurovascular bundle.

Clause 16: The cryoprotective composition of any of clauses 1-15, wherein, when the cryoprotective composition is applied to the body space, the cryoprotective composition maintains a temperature of surrounding body tissues of at least about 30° C.

Clause 17: The cryoprotective composition of any of clauses 1-16, wherein the body space comprises a periprostatic space.

Clause 18: The cryoprotective composition of any of clauses 1-17, further comprising Krebs phosphate solution.

Clause 19: The cryoprotective composition of any of clauses 1-18, wherein the gel comprises at least one of cellulose and/or hyaluronic acid.

Clause 20: The cryoprotective composition of any of clauses 1-19, wherein the at least one non-toxic cryoprotectant agent comprises Dimethyl sulfoxide (DMSO) comprising from about 1 weight percent to about 5 weight percent of the cryoprotective composition, and wherein the at least one biodegradable and/or bioerodible fluid agent comprises hydroxyethyl cellulose comprising from about 1 weight percent to about 4 weight percent of the cryoprotective composition.

Clause 21: The cryoprotective composition of any of clauses 1-20, wherein the at least one non-toxic cryoprotectant agent comprises Dimethyl sulfoxide (DMSO) comprising from about 1 weight percent to about 5 weight percent of the cryoprotective composition and from about 0.2M to about 0.4M trehalose, and wherein the at least one biodegradable and/or bioerodible fluid agent comprises hydroxyethyl cellulose comprising from about 1 weight percent to about 4 weight percent of the cryoprotective composition.

Clause 22: The cryoprotective composition of any of clauses 1-21, wherein the at least one non-toxic cryoprotectant agent comprises Dimethyl sulfoxide (DMSO) comprising about 5 weight percent of the cryoprotective composition and about 0.2M trehalose, and wherein the at least one biodegradable and/or bioerodible fluid agent comprises hydroxyethyl cellulose comprising from about 1 weight percent to about 4 weight percent of the cryoprotective composition.

Clause 23: The cryoprotective composition of any of clauses 1-22, wherein the at least one non-toxic cryoprotectant agent comprises Dimethyl sulfoxide (DMSO) comprising from about 1 weight percent to about 5 weight percent of the cryoprotective composition and from about 0.2M to about 0.4M trehalose, and wherein the at least one biodegradable and/or bioerodible fluid agent comprises hyaluronic acid comprising from about 1 weight percent to about 4 weight percent of the cryoprotective composition.

Clause 24: The cryoprotective composition of any of clauses 1-23, wherein the at least one non-toxic cryoprotectant agent comprises Dimethyl sulfoxide (DMSO) comprising about 5 weight percent of the cryoprotective composition and about 0.2M trehalose, and wherein the at least one biodegradable and/or bioerodible fluid agent comprises hyaluronic acid comprising from about 1 weight percent to about 2 weight percent of the cryoprotective composition.

Clause 25: A method of protecting a surgical site during prostate cryosurgery comprising injecting the therapeutically effective amount of the cryoprotective composition of any of clauses 1-24 into the body space, wherein the body space is a periprostatic space of a patient.

Clause 26: The method of clause 25, wherein injecting the cryoprotective composition comprises injecting the cryoprotective composition to portions of the periprostatic space surrounding a neurovascular bundle (NVB) adjacent to a prostate of the patient.

Clause 27: The method of clause 25 or clause 26, wherein a size of a needle used for the injection of the cryoprotective composition into the periprostatic space ranges from an 18 gauge needle to a 22 gauge needle.

Clause 28: The method of clause 27, wherein the injection is performed with ultrasound visualization of the needle and the periprostatic space with the patient in a lithotomy position.

Clause 29: The method of clause 28, wherein the ultrasound visualization is provided by a transrectal ultrasound.

Clause 30: The method of any of clauses 25-29, wherein the injection of the cryoprotective composition to the periprostatic space comprises: inserting a tip of a syringe needle through a perineum of the patient, under ultrasound guidance, advancing the tip of the needle from an insertion site in the perineum to perforate a Denonvillier's fascia of the periprostatic space distal to the prostate, injecting a first amount of the cryoprotective composition to a portion of the periprostatic space between the prostate and rectum, and continuing to inject the cryoprotective composition from the tip of the needle while retracting the needle from a base of the prostate to an apex of the prostate.

Clause 31: The method of clause 30, wherein the injection of the cryoprotective composition to the periprostatic space further comprises injecting a second amount of the cryoprotective composition to spaces surrounding a neurovascular bundle adjacent to the prostate.

Clause 32: The method of any of clauses 1-31, wherein the cryoprotective composition is injected into the body space, wherein the body space is a space between a base of the prostate and an apex of the prostate.

Clause 33: The method of any of clauses 25-32, wherein the injected cryoprotective composition substantially or fully envelops a neurovascular bundle of the patient adjacent to the prostate.

Clause 34: The method of any of clauses 25-33, wherein the cryosurgical procedure comprises tumor ablation of a prostate tumor.

Clause 35: A surgical method for destruction of a solid mass, comprising: injecting the cryoprotective composition of any of clauses 25-34 into the body space of the patient, the body space being adjacent to the solid mass; and performing a cryosurgical procedure for removal and/or destruction of the solid mass while the cryoprotective composition is positioned in the space adjacent to the solid mass.

Clause 36: The surgical method of clause 35, wherein the solid mass comprises a tumor located or adjacent to at least one of a prostate, lungs, liver, kidney, adrenals, breast, or skin of a patient.

Clause 37: A surgical method for use during neurosurgery, the method comprising: injecting the cryoprotective composition of any of clauses 1-24 into the body space of the patient, wherein the body space comprises spaces adjacent to the spine and/or brain; and performing a cryosurgical procedure for treatment of neurological conditions while the cryoprotective composition is positioned in the spaces adjacent to the spine and/or brain.

Clause 38: A cryosurgical method for treating one or more of cardiac arrhythmia, ablation of aberrant nerves in proximity to a pulmonary artery, tumor(s) and/or lesions around an eye or eye orbit, esophageal tumor(s) and/or cancer, pancreatitis, pancreatic tumor(s) and/or cancer, rectal proctitis, liver tumor(s) and/or cancer, brain tumor(s) and/or cancer, cryolipolysis, chronic pain caused by trigeminal neuralgia, and/or organ transplantation, the method comprising: injecting the cryoprotective composition of any of clauses 1-24 into the body space of the patient, wherein the body space comprises spaces adjacent to organs and/or body tissues to be treated by at least one cryosurgical procedure; and performing the at least one cryosurgical procedure while the cryoprotective composition is positioned in the spaces adjacent to the organs and/or body tissues to be treated.

Clause 39: A topical protective composition configured to be applied to skin, the protective composition comprising: at least one biodegradable and/or bioerodible fluid agent; and at least one non-toxic cryoprotectant agent, wherein the protective composition is configured to protect the skin from damage caused by environmental conditions, and wherein the composition does not cause substantial damage to the skin.

Clause 40: The topical protective composition of clause 39, wherein the protective composition is configured to protect the skin from frostbite.

Clause 41: A cryoprotective composition for use in cryosurgery comprising: at least one biodegradable and/or bioerodible fluid agent comprising a gel of from about 1 weight percent to about 10 weight percent of the composition; and at least one non-toxic cryoprotectant agent, wherein the cryoprotective composition does not cause substantial nerve damage when positioned in a body space for a duration of a cryosurgical procedure.

Clause 42: The cryoprotective composition of clause 41, wherein the at least one non-toxic cryoprotectant agent comprises from about 1 weight percent to about 10 weight percent of the composition.

Clause 43: The cryoprotective composition of clause 41 or clause 42, wherein the at least one non-toxic cryoprotectant agent comprises Dimethyl sulfoxide (DMSO) comprising from about 1 weight percent to about 5 weight percent of the cryoprotective composition.

Clause 44: The cryoprotective composition of any of clauses 41-43, wherein the at least one non-toxic cryoprotectant agent comprises Dimethyl sulfoxide (DMSO) comprising from about 1 weight percent to about 5 weight percent of the cryoprotective composition and from about 0.2M to about 0.4M trehalose, and wherein the at least one biodegradable and/or bioerodible fluid agent comprises hydroxyethyl cellulose comprising from about 1 weight percent to about 4 weight percent of the cryoprotective composition.

Clause 45: The cryoprotective composition of clauses 41-44, wherein the at least one non-toxic cryoprotectant agent comprises Dimethyl sulfoxide (DMSO) comprising from about 1 weight percent to about 5 weight percent of the cryoprotective composition and from about 0.2M to about 0.4M trehalose, and wherein the at least one biodegradable and/or bioerodible fluid agent comprises hyaluronic acid comprising from about 1 weight percent to about 4 weight percent of the cryoprotective composition.

Clause 46: A composition for protecting plants from frost and/or freezing, the composition comprising: at least one biodegradable and/or bioerodible fluid agent; and at least one non-toxic cryoprotectant agent, wherein the protective composition is configured to protect portions of a plant from damage caused by frost and/or freezing, and wherein the composition does not cause substantial damage to the plant.

Clause 47: The composition for protecting plants of clause 46, wherein the at least one fluid agent comprises a gel, the gel comprising from about 1 weight percent to about 10 weight percent of the composition.

Clause 48: The composition for protecting plants of clause 47, wherein the gel comprise hydroxyethyl cellulose and/or hyaluronic acid.

Clause 49: The composition for protecting plants of any of clauses 46-48, wherein the at least one non-toxic cryoprotectant agent comprises from about 1 weight percent to about 10 weight percent of the composition.

Clause 50: The composition for protecting plants of any of clauses 46-49, wherein the at least one non-toxic cryoprotectant agent comprises Dimethyl sulfoxide (DMSO) comprising from about 1 weight percent to about 5 weight percent of the composition.

Clause 51: The composition for protecting plants of any of clauses 46-50, wherein the at least one non-toxic cryoprotectant agent comprises Dimethyl sulfoxide (DMSO) comprising from about 1 weight percent to about 5 weight percent of the composition and from about 0.2M to about 0.4M trehalose.

Clause 52: A method for protecting a plant from frost and/or freezing, comprising coating at least a portion of a surface of the plant with the composition of any of clauses 46-51.

Clause 53: The method of clause 52, wherein coating the surface of the plant comprises at least one of spraying the composition over the surface of the plant, pouring the composition over the surface of the plant, or immersing a portion of the plant in a bath of the composition.

Clause 54: The method of clause 52 or clause 53, wherein coating the surface of the plant comprises immersing roots of the plant in a bath of the composition.

Clause 55: The method of any of clauses 52-54, wherein the plant comprises at least one of a fruit tree, citrus tree, grape vine, flowering tree, flowering bush, hay, grains, grasses, corn, or soybeans.

Clause 56: The method of any of clauses 52-55, wherein applying the composition to the portion of the surface of the plant comprises applying the composition to leaves, stems, buds, flowers, or fruit of the plant.

BRIEF DESCRIPTION OF THE DRAWINGS

These and other features and characteristics of the present disclosure, as well as the methods of operation, use, and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

Further features and other examples and advantages will become apparent from the following detailed description made with reference to the drawings in which:

FIGS. 1A and 1B are schematic drawings of a patient showing an injection site on the perineum for injecting cryoprotective composition(s) of the present disclosure to the periprostatic space;

FIGS. 7A-7D are temperature profiles for cross sections of a prostate after cryoprobes are sequentially turned off, which can be used to create a model of prostate temperature during cryosurgery, according to an example of the present disclosure;

DETAILED DESCRIPTION

Figure 1A:
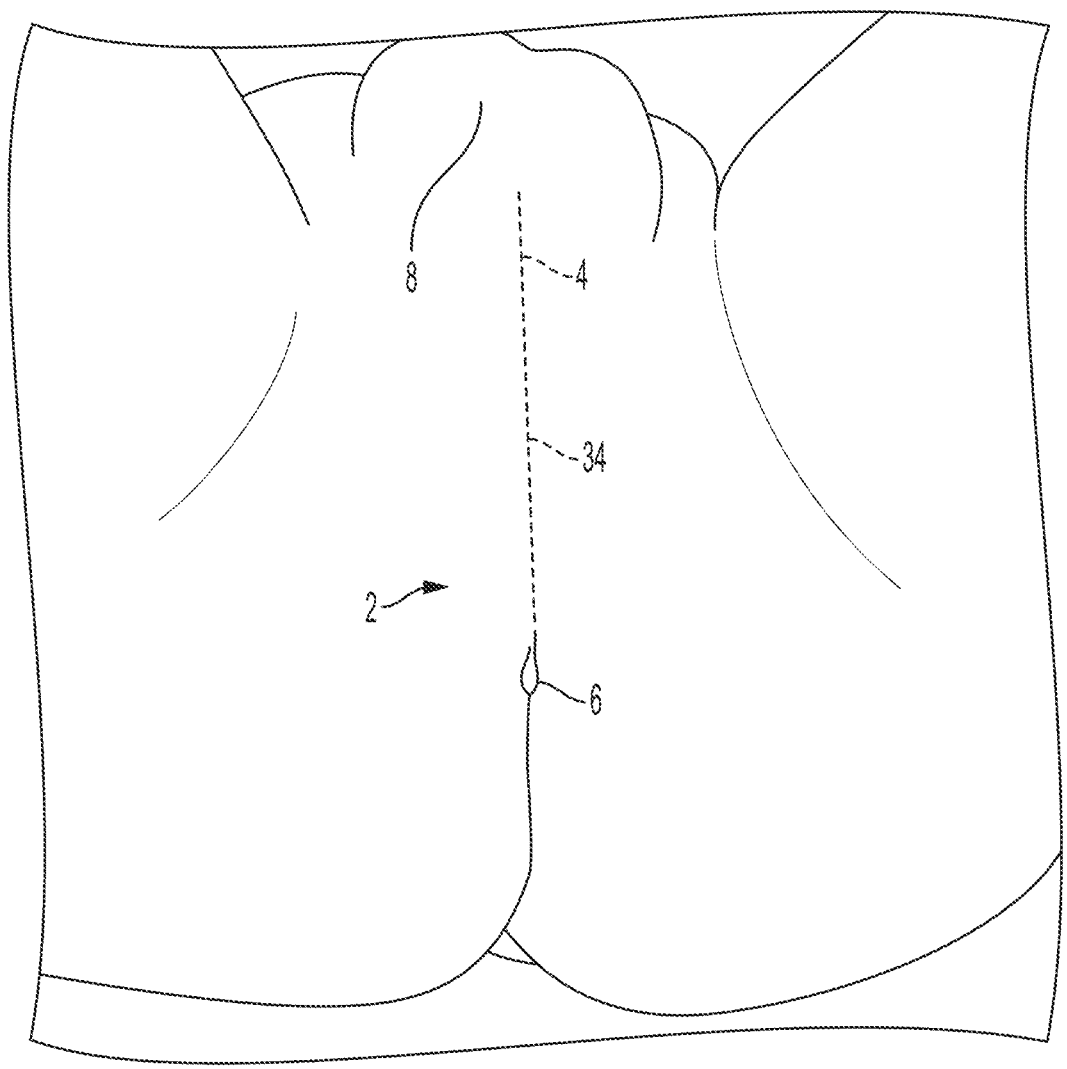

As used herein, the singular form of "a", "an", and "the" include plural referents unless the context clearly states otherwise.

As used herein, the terms "right", "left", "top", and derivatives thereof shall relate to the invention as it is oriented in the drawing figures. For a device, system, or surgical tool, the term "proximal" refers to a portion of the device, system, or tool nearest to the access site through which the device, system, or tool enters the body. The term "proximal" can also refer to the portion of the tool being held or manipulated by a user. For example, a handle of a tool may be located at the "proximal end" of the tool. The term "distal" refers to the opposite end of a device, system, or tool from the proximal end and, for example, to the portion of the device or system that is inserted farthest into the patient's body (e.g., farthest into the periprostatic space). The term "distal" can also refer to an end or portion of a tool farthest from the portion of the tool held or manipulated by the user. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

For the purposes of this specification, unless otherwise indicated, all numbers expressing quantities of ingredients, reaction conditions, dimensions, physical characteristics, and so forth used in the specification and claims are to be understood as being modified in all instances by the term "about." Unless indicated to the contrary, the numerical parameters set forth in the following specification and attached claims are approximations that can vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Numerical values may inherently contain certain errors resulting from a standard deviation found in their respective testing measurements.

Also, it should be understood that any numerical range recited herein is intended to include all sub-ranges subsumed therein. For example, a range of "1 to 10" is intended to include any and all sub-ranges between and including the recited minimum value of 1 and the recited maximum value of 10, that is, all subranges beginning with a minimum value equal to or greater than 1 and ending with a maximum value equal to or less than 10, and all subranges in between, e.g., 1 to 6.3, or 5.5 to 10, or 2.7 to 6.1.

The present disclosure is directed to a cryoprotective composition(s) that protects internal or external body tissues of patients or tissues and surfaces of plants from exposure to cold temperatures, which may result in damage to the body tissue. As used herein, "body tissue" of the patient refers to arrangements of cells grouped together by structure and/or function. Non-limiting examples of body tissue may include muscle tissues, epithelial tissues, connective tissues, and/or nervous tissues. Body tissue can also include internal organs, such as the prostate, rectum, liver, lung, heart, kidney, brain, or any other organ that may be exposed to cold temperatures during, for example, a cryosurgical treatment or procedure. Body tissue can also include external tissues, such as skin. Body tissue can also include tissues of plants including, for example, parenchyma, collenchyma, and sclerenchyma tissues of a plant, as well as vascular tissues and dermal tissues of plants.

Protecting body tissue means that the cryoprotective composition(s) preserves the body tissue so that it can function normally or substantially normally following exposure to a damaging condition. For example, the cryoprotective composition may preserve nerve cells so that after freezing and thawing, the nerve cells are able to generate an action potential and/or an action potential is able to translate along a length of the nerve cells, as could occur prior to the freezing and thawing.

As used herein, the "patient" can be any species of the human or animal kingdom having body tissues, such as nerve cells, that can be damaged by exposure to cold or freezing temperatures. Non-limiting examples of patients include mammal(s), such as human(s) and/or non-mammalian animal(s). Non-limiting examples of mammal(s) include primate(s) and/or non-primate(s). Primate(s) include human(s) and non-human primate(s), including but not limited to male(s), female(s), adult(s), and children. Non-limiting examples of non-human primate(s) include monkey(s) and/or ape(s), for example, chimpanzee(s). Non-limiting examples of non-primate(s) include cattle (such as cow(s), bull(s) and/or calves), pig(s), camel(s), llama(s), alpaca(s), horse(s), donkey(s), goat(s), rabbit(s), sheep, hamster(s), guinea pig(s), cat(s), dog(s), rat(s), mice, lion(s), whale(s), and/or dolphin(s). Non-limiting examples of non-mammalian animal(s) include bird(s) (e.g., duck(s) or geese), reptile(s) (e.g., lizard(s), snake(s), or alligator(s)), amphibian(s) (e.g., frog(s)), and/or fish. In some examples, the animals can be zoological animals, human pets, and/or wild animals.

As used herein, "cold temperature" for patients means that a temperature of a material or object contacting the body tissue that should be preserved or protected is below about 0° C., or about −10° C., or about −30° C. Non-limiting examples of the objects or materials that may contact the body tissue can include cryoprobes used for surgical procedures, other frozen and/or super-cooled medical devices, or fluids capable of being cooled to below 0° C. injected to the patient for certain cryotherapy treatments and procedures. The "material" can also be air if, for example, the patient's skin is exposed to cold temperatures.

For plants, "cold temperature" means that the temperature of a material contacting exposed surfaces or portions of the plant is below about 0° C., or about −5° C., or about −15° C. The material contacting the body tissue can be in gaseous, liquid, and/or solid form, or any combination thereof. Non-limiting examples of materials that can contact exposed surfaces of plants includes air (when air temperature is at or below freezing) or precipitation (e.g., ice or snow). For plants, non-limiting examples of surfaces or portions of a plant that can be protected by the cryoprotective composition can include ground, vascular, and/or dermal tissue of the plant. Non-limiting examples of ground tissue include parenchyma, collenchyma, and sclerenchyma. Non limiting examples of vascular tissue include tracheids and vessel elements, sieve tubes, and companion cells. Non-limiting examples of dermal tissue include epidermal cell, stomata and trichromes. Each plant organ (roots, stems, leaves) contains all three types of tissue. Dermal tissue covers and protects the plant, and controls gas exchange and water absorption (in the roots).

During treatments and/or surgical procedures of patients, cryoprotectant agents can be used to prevent freezing or damage to body tissues during or after the treatment and/or surgery. As discussed previously, there are many treatments and surgical procedures that involve treatment with cold temperatures to prevent pain, lessen swelling, or destroy or treat defective or injured tissue, such as cancer cells, including, for example, cryosurgical treatment for prostate cancer, liver cancer, cervical cancer, and other conditions. It may be desirable to protect adjacent tissue which is not the target of such treatment or surgery from the effects of the cold temperatures or freezing.

The cryoprotective composition(s) desirably remain in place at an injection or deposition site for a duration of a treatment or surgical procedure. After the completion of the procedure, the cryoprotective composition(s) can begin to degrade or erode and can be absorbed by or passed through the body. Further, the cryoprotective composition(s) desirably has low toxicity and does not appreciably damage nerves or body tissue in proximity to the injection or deposition site for the cryoprotective composition(s).

In some examples, the cryoprotective composition(s) of the present disclosure are intended to preserve body tissues and nerves from damage during prostate cryotherapy treatment. While the inventive cryoprotective composition(s) will be discussed first with reference to prostate cryotherapy treatment, one of ordinary skill in the art will appreciate that these cryoprotective composition(s) can be useful in any treatment, surgical, or cryosurgical applications to inhibit damage to adjacent tissues and organs, as desired.

In other examples, the cryoprotective composition(s) of the present disclosure can be used to diminish side effects in focal cryotherapy with regards to erectile function. The cryoprotective composition(s) of the present disclosure can also be used to increase surgical safety with regard to damage to surrounding organs, namely the intestines. The cryoprotective composition(s) of the present disclosure can also be used for other cryo-applications in the body including, for example, metastases of the liver, lung, or skeleton. It is believed that the cryoprotective composition(s) of the present disclosure may become safer and more efficient allowing for protection of surrounding structures, such as vessels and nerves.

In other examples, the cryoprotective composition(s) of the present disclosure can be used for any surgery involving neuronal tissue where tissue cooling is involved. In such cases, it is believed that a cryoprotective composition(s) comprising a gel may protect non-targeted areas during, for example, brain surgery or spinal surgery, from negative effects caused by cooling and/or exposure to cold temperatures.

In some other examples, the cryoprotective composition(s) of the present disclosure can be used to protect body tissues during other types of cryo-treatments as are presently performed or as may be identified in the future. For example, it may be possible that cryotherapy could be used as an alternative treatment for presently-performed neuromodulation therapy (e.g., neuromodulation for treatment of hyperactive bladder, intestinal disorders, and chronic pain). If cryotherapy is used to treat such conditions, then the cryoprotective composition(s) of the present disclosure may be used to protect body tissues surrounding treatment sites during such procedures.

In some examples, the cryoprotective composition(s) can be used in topical protective composition(s) and skin creams or locations for protecting external portions of the body tissue, such as the skin, from exposure to cold temperatures.

In some examples, the cryoprotective composition(s) can be used to protect surfaces, external tissues, and/or internal tissues of plants from exposure to cold temperatures, which might result in damage to the tissue. For example, the cryoprotective composition(s) of the present disclosure can protect surfaces of plants from freezing and/or exposure to freezing temperatures, which would otherwise damage portions of the plant. The cryoprotective composition(s) of the present disclosure can also be used for protecting other internal and/or external tissue and organs of plants including, for example, ground, vascular, and/or dermal tissues of plants. Non-limiting examples of ground tissues include parenchyma, collenchyma and sclerenchyma. Non-limiting examples of vascular tissues include tracheids and vessel elements, sieve tubes and companion cells. Non-limiting examples of dermal tissues include epidermal cell, stomata and trichomes. Each plant organ (roots, stems, leaves) contains all three types of tissue: Dermal tissue covers and protects the plant, and controls gas exchange and water absorption (in the roots).

Cryosurgery Examples

While current prostate cryotherapy procedures have low morbidity for urinary incontinence with 0-1%, as previously discussed, complications related to erectile dysfunction occur more frequently (about 40% erectile dysfunction for focal therapy and 70% for whole gland therapy). It is believed that when using the cryoprotective composition(s) of the present disclosure, cryotherapy can become a viable treatment option for patients, while reducing the risk of complications, such as erectile dysfunction and other conditions caused by damage to adjacent tissue and organs.

In order to provide such protection, as described in further detail herein, the cryoprotective composition(s) can be applied during prostate cryotherapy to at least partially, or fully, surround the prostate and/or neurovascular nerve bundle. It is believed that applying the cryoprotective composition in this manner will also address other common complications associated with prostate cryotherapy procedures comprising, but not limited to, rectal injury due to the close proximity of the anterior rectum to the posterior prostate. It is believed that risks of rectal injury during cryotherapy are particularly high when the prostate has been previously irradiated, as radiation treatment causes scarring that reduces the space between the rectum and prostate. The cryoprotective composition(s) may also be used to protect other non-targeted anatomical structures during prostate cryotherapy procedures comprising, for example, the urethra, urogenital diaphragm, external urinary sphincter, and/or bladder neck smooth muscle sphincter, which may be susceptible to damage from exposure to cold and/or freezing.

In some examples, the cryoprotective composition(s) creates space around the prostate, which physically separates sensitive structures, such as the neurovascular bundle and the rectum, from the prostate to reduce direct and indirect effects of the cold (e.g., cryotherapy agents) on such sensitive structures. In addition to creating physical separation, the cryoprotective composition(s) are also configured to interfere with various electrochemical and/or chemical mechanisms that cause cryoinjury. For example, the injected cryoprotective composition(s) are believed to preserve an ability of the neurovascular bundle to generate action potentials, which may be inhibited when the neurovascular bundle is exposed to cold (e.g., cryotherapy agents). Further, use of the cryoprotective composition(s) of the present disclosure can confine cryoinjury to selected target zones (e.g., the entire prostate and/or select quadrants of the prostate), which protects surrounding structures from thermal damage.

In some examples, it is believed that the cryoprotective composition(s) can be used in clinical practice with image guidance by commonly used ultrasound, such as transrectal ultrasound, and delivered by a conventional needle to surgical sites that would otherwise be subjected to damage by exposure to cold during cryotherapy. Image guidance for delivery of the cryoprotective composition(s) can also be provided by other known medical imaging systems, such as MRI or CT. In some examples, the cryoprotective composition is delivered during a pre-treatment phase of a cryosurgical procedure. As such, it is believed that no changes may need to be made to existing cryosurgical protocols. For example, for procedures using the cryoprotective composition(s) of the present disclosure, there is no need for complicated control systems (e.g., electronic control systems for active heating devices), modifications of existing surgical equipment, or introduction of new devices, as is often needed for active heating devices and newly developed focal treatment methods. Further, since the cryoprotective composition(s) is not expected to come into contact with the target tumor, there is no risk of compromising efficacy of tumor ablation, which could increase the possibility for cancer recurrence.

The cryoprotective composition(s) of the present disclosure may also have numerous uses beyond use in cryotherapy of the prostate. For example, in many oncological fields, there may be an interest in treating certain tumor(s) and/or cancers by performing in situ (e.g., a tissue preserving approach) tumor treatment instead of organ removal for solid tumors or tumor metastasis. For example, the cryoprotective composition(s) may be used in surgical procedures for treatment of one or more of tumor(s) and/or lesions around an eye or eye orbit, esophageal tumor(s) and/or cancer, pancreatic tumor(s) and/or cancer, liver tumor(s) and/or cancer, brain tumor(s) and/or cancer, kidney tumor(s) and/or cancer, lung tumor(s) and/or cancer, or breast tumor(s) and/or cancer.

For example, during treatment of tumors and lesions around the eye and the eye orbit by cryosurgery, vital structures such as the retina, the lacrimal duct, and the optic nerve can become damaged. The cryoprotective composition(s) can also be applied in proximity to such vital structures to avoid tissue damage and complications.

Cryotherapy is also used to treat Barrett's esophagus and esophageal tumor(s) and/or cancer. In such procedures, there is a potential for perforation of the esophagus, which can be a serious and life-threatening complication. The cryoprotective composition(s) can be applied adjacent to the esophagus to protect the esophagus and, in particular, to prevent perforation of esophageal structures or damage to adjacent neural tissue.

The cryoprotective composition(s) of the present disclosure can also be used for treatment of pancreatitis and pancreatic tumor(s) and/or cancer, to avoid serious complications caused by injuries to the bile duct during cryosurgery, and for treatment of liver tumor(s) and/or cancer. For example, during cryosurgery on the liver, where tumors are located close to large blood vessels, it is important to freeze the tumors as close to the blood vessels as possible without damaging the blood vessels themselves. The cryoprotective composition(s) may be applied in proximity to the large blood vessels, which allows the cryotherapy agent to be applied close to the vessels, while reducing risks that the blood vessels will be damaged.

The cryoprotective composition(s) and surgical methods described herein may also be applicable for non-oncological surgical procedures where cryotherapy is desirable and adjacent tissues need to be protected. For example, cryotherapy can be performed in order to treat cardiac arrhythmias and/or for ablation of aberrant nerves in proximity to the pulmonary artery. A serious complication of these procedures can be damage to phrenic nerves, such that the diaphragm is no longer able to contract and normal breathing is not possible. The cryoprotective composition(s) of the present disclosure may be deposited in proximity to phrenic nerves to preserve normal function for these structures.

The cryoprotective composition(s) can also be used during rectal surgeries, such as cryotherapy of rectal proctitis. For example, the cryoprotective composition(s) can be used to avoid complications, such as vascular necrosis, that can occur during cryotherapy of cutaneous lesions and/or perforation(s) and fistula formation.

Cryoprotective Composition(s)

In some examples, the cryoprotective composition(s) of the present disclosure is configured for use in cryosurgery. In order to provide suitable protection for body tissues surrounding and/or in proximity to a surgical site, in some examples the cryoprotective composition(s) is configured to be of a viscosity such that a therapeutically effective amount of the cryoprotective composition(s) deposited in a body space of a patient in proximity to a cryotreatment site or a surgical site remains within or approximately within at least a portion of the body space for a duration of the cryotreatment or surgical procedure. Also, in some examples, at least a portion of a body tissue(s) proximate to the body space of the patient in proximity to a cryotreatment site or a surgical site is or remains viable after the cryotreatment or surgical procedure. Also, in some examples, the cryoprotective composition(s) does not cause substantial nerve and/or tissue damage when positioned in the body space for the duration of the cryosurgical procedure.

As used herein, "substantial nerve damage" can refer to nerves that do not have at least about 10%, about 15%, about 30%, or about 50% action potential recovery after being frozen. Methods for measuring action potential recovery of nerves are described in Experimental Examples described elsewhere in the present disclosure.

The cryoprotective composition(s) may protect tissues adjacent to surgical sites during cryosurgical procedures by creating space between target tissues exposed to cryosurgical agents and surrounding body tissue. Also, the cryoprotective composition(s) have cryoprotective or antifreeze characteristics that prevent the cryoprotective composition(s) from freezing and prevent the freezing temperatures from passing from the cryotherapy injection site and/or target tissue through the cryoprotective composition(s) to surrounding tissues. In some examples, the combination of spacing and cryoprotective properties may protect surrounding tissues from being exposed to cold temperatures that might cause cellular structures of the surrounding body tissues to crystallize and/or freeze, thereby injuring and/or destroying the cellular structures of the surrounding body tissues. Further, in order to avoid causing damage to the surrounding body tissues, in some examples the cryoprotective composition(s) may comprise primarily biocompatible materials.

A "biocompatible material" means that the material and degradation products thereof are substantially non-toxic to cells or organisms within acceptable tolerances, for example, comprising substantially non-carcinogenic and substantially non-immunogenic substances, and can be cleared or otherwise degraded in a biological system, such as an organism (patient or plant) without substantial toxic effect. Non-limiting examples of degradation mechanisms within a biological system can comprise chemical reactions, hydrolysis reactions, and enzymatic cleavage. For example, as described in further detail herein, cryoprotectant agents of the cryoprotective composition(s) can be selected that, in concentrations used for the cryoprotective composition(s), do not appreciably affect an ability of nerve cells to generate action potentials. Methods for determining action potential recovery for nerves are described in Experimental Examples described elsewhere in the present disclosure.

In some examples, the cryoprotective composition(s) comprises at least one biodegradable and/or bioerodible fluid agent(s). As used herein, a "fluid agent" means a liquid, foam, suspension, mixture, aerosol, or gel configured to be deposited or injected into a predetermined area of the internal or external body of the patient or to be coated on or applied within a portion of a plant. In some examples, once deposited or injected, the fluid agent(s) remain in place for the duration of a treatment or cryosurgical procedure or for the time period in which resistance to freezing is desired. In some examples, the fluid agent comprises a biocompatible liquid. Alternatively or in addition, the fluid agent can comprise a biocompatible gel, such as a gel comprising a biocompatible polymer. The fluid agent can also comprise and/or be mixed with various thickening agents, as are commonly used in the food and cosmetic industries, as well as with selected biocides and/or preservatives.

For example, the cryoprotective composition can comprise one or more of the following gels and/or thickening agents: protein-based ingredients (e.g., gelatin and collagen); sugar-based ingredients (e.g., honey and syrup); polymer-based ingredients (e.g., polyvinyl alcohol and Poloxamer 407); and/or polysaccharides (e.g., hyaluronic acid). Poloxamer 407 is a triblock copolymer comprising a central hydrophobic block of polypropylene glycol flanked by two hydrophilic blocks of polyethylene glycol. Other suitable fluid agents can comprise other additives that have been generally recognized as safe (GRAS) for use in foods and medications. In some examples, the biocompatible gel can comprise cellulose, cellulose ethers, such as hydroxyethyl cellulose, hydroxypropyl cellulose, and/or hydroxypropyl methylcellulose.

In other examples, the thickening agent or gel can comprise hyaluronic acid, such as hyaluronic acid produced from plant, animal, or microbial sources. In some examples, the thickening agent or gel is a cross-linked hyaluronic acid as described, for example, in U.S. Pat. No. 10,117,822 entitled "Cross-linked hyaluronic acid, process for the preparation thereof and use thereof in the aesthetic field", which is incorporated by reference herein in its entirety.

As described in further detail herein, in some examples, the fluid agent can be selected to permit sufficient diffusion into body tissue and/or to remain within a body space or body cavity for a duration of a treatment or surgical procedure prior to substantially degrading or eroding. Also, the fluid agent can be selected so that the cryoprotective composition, at about room temperature (e.g., between about 20° C. and about 25° C.), is of suitable viscosity to be ejected from a syringe through a needle cannula, such as a cannula of an 18 gauge needle to a 22 gauge needle. In some examples, in order to provide a composition of suitable viscosity, the fluid agent or gel can comprise up to about 10 weight percent of the cryoprotective composition, less than about 5 weight percent of the cryoprotective composition, less than about 2 weight percent of the cryoprotective composition, about 1 weight percent to about 10 weight percent of the cryoprotective composition, about 1 weight percent to about 5 weight percent of the cryoprotective composition, 1 weight perfect to 4 weight percent of the cryoprotective composition, or about 1 weight percent to about 2 weight percent of the cryoprotective composition.

In some examples, the fluid agent is used to produce a stable deposit in the body space to provide sufficient time for the delivered cryoprotectant agent (CPA) to diffuse into the targeted tissue without being quickly absorbed into the intracellular space and bloodstream. However, mixing the cryoprotectant agent with higher viscosity substances, such as gels having high viscosity at body temperature, may impede diffusion of the cryoprotectant agent contained in the gel. Therefore, viscosity of the fluid agent and cryoprotective composition can be selected to permit sufficient diffusion into target tissues.

In some examples, the fluid agent can comprise an ultrasound gel (e.g., Aquasonic 100 ultrasound gel manufactured by Parker Laboratories, Inc.). The ultrasound gel can comprise, for example: thickening agents or texture enhancers (e.g., polymers of acrylic acids, such as poly(acrylic acids) and/or acrylates/C10-30 alkyl acrylate crosspolymer); surfactants and emulsifiers (e.g., triethanolamine); preservative, antibacterial, and/or antifungal agents (methylchloroisothiazolinone and methylisothiazolinone); and deionized water. For example, an exemplary ultrasound gel can comprise: 0.3 to 1 percentage weight per volume (w/v %) of Carbomer; 0.3 to 1 w/v % of triethanolamine; 0.5 to 2 w/v % of monopropylene glycol; 0.05 to 0.15 w/v % of methylchloroisothiazolinone and methylisothiazolinone; and deionized water.

In some examples, a viscosity of the fluid agent and/or the cryoprotective composition(s) prior to application in or to the patient can range from about 150 cP to about 3,000 cP at a temperature of about 20° C. to about 37° C., or about 25° C. Viscosity can be measured using a viscometer or rheometer.

In some examples, the pH of the fluid agent and/or cryoprotective composition(s) can range from about 4 to about 8, or from about 6.5 to about 7.5 or a pH of about 7, at a temperature of about 20° C. to about 37° C., or about 25° C.

As used herein, "biodegradable or "bioerodible" means a material that, once deposited or injected into the body and placed in contact with bodily fluids and tissues, will degrade either partially or completely through chemical and/or biological reactions with the bodily fluids and/or tissues. Non-limiting examples of such chemical reactions can comprise acid/base reactions, hydrolysis reactions, and enzymatic cleavage. The biodegradation or erosion rate of the fluid agent may be manipulated, optimized, or otherwise adjusted so that the cryoprotective composition(s) remains in place in the body for the duration of the surgery before passing from the injection site.

As used herein, remaining in place (e.g., at a deposited location or an injected location) for the "duration of the treatment" or "duration of the surgery" means that the cryoprotective composition(s) has a viscosity such that a therapeutically effective amount of the cryoprotective composition(s) sufficient to protect body tissues (e.g., the neurovascular bundle, other quadrants of the prostate, nerves, organs, and other body tissues) remains in place for at least a duration of the treatment or surgical procedure.

As used herein, a "therapeutically effective amount" means an amount of the cryoprotective composition(s) sufficient to protect surrounding tissues from cold created by cryotherapy agents used during cryosurgery, for example, to prevent and/or inhibit freezing of cellular structures of the surrounding tissues. This prevention and/or inhibition of freezing can be a result of physical spacing between target tissues and surrounding tissues created by the injected cryoprotective composition(s) and/or cryoprotective or antifreeze properties of the cryoprotective composition(s). For example, when the cryoprotective composition(s) is used for cryosurgery of the prostate, the "therapeutically effective amount" of the cryoprotective composition may be an amount of the cryoprotective composition(s) sufficient to prevent and/or inhibit crystallization or freezing of nerve cells of the neurovascular bundle and to preserve an ability of nerves of the neurovascular bundle to generate action potentials. The "therapeutically effective amount" could also be an amount of the cryoprotective composition(s) sufficient to maintain a temperature of body structures or tissues (e.g., the neurovascular bundle, rectum, or bladder) encapsulated, covered, or in proximity to the cryoprotective composition(s) at a temperature ranging from about 30° C. to about 36° C., or at least about 30° C. as cryotherapy agents are applied to the surgical site and target tissue (e.g., to the prostate and/or to tumor(s) or cancerous tissue to be destroyed). It is believed that nerve tissues might continue to function even after being exposed to temperatures of about negative 10° C. However, it is believed that a threshold for non-recoverable injury without a cryoprotectant agent may be exposure to negative 3° C. for at least about 5 minutes. In some examples, when the cryoprotective composition is applied to the neurovascular bundle, the threshold for non-recoverable injury may be improved to be from about negative 10° C. to about negative 15° C. for at least about 10 minutes.

Desirably, the cryoprotective composition passes, deteriorates, or is eliminated from the body shortly after completion of the treatment or surgical procedure. For example, the duration of the treatment or surgical procedure (e.g., duration that the cryoprotective composition remains at its deposited or injection location) can be, for example, from about 10 minutes to about 5 hours, from about 20 minutes to about 2 hours, or from about 30 minutes to about 2 hours. It is believed that most cryosurgical treatments or procedures can be performed within a period of about 10 minute to about 5 hours.

As previously discussed, the "body space" can refer to any cavity or space surrounding a body tissue or organ to be treated by a cryosurgical treatment or procedure. When the cryoprotective composition(s) is used for prostate surgery, the body space can refer to the periprostatic space, which is the space surrounding the prostate and/or a space defined by the prostate, bladder, and rectum. The periprostatic space refers to a space that is limited posteriorly by the rectum, anteriorly by fat tissue and the pubic bone (symphysis), and laterally by the periprostatic fat tissue and/or pelvic floor muscles. Anatomical structures of the periprostatic space are shown in the schematic drawings of FIGS. 2A-4B, and are described in further detail in the discussion of surgical methods using the cryoprotective composition(s) disclosed herein.

In other examples, the body space can refer to spaces surrounding a solid mass, such as a primary or metastasized tumor. In other examples, the body space can refer to spaces surrounding other organs, such as the liver, heart, lungs, eyes, brain, or spine.

The cryoprotective composition(s) further comprises at least one non-toxic cryoprotectant agent that does not cause substantial nerve damage when positioned in the body space for the duration of the treatment or cryosurgical procedure, or as applied externally. In some examples, the at least one non-toxic cryoprotectant agent can comprise up to about 20 weight percent, or about 0.01 to about 20 weight percent, or about 1 to about 20 weight percent, or about 2 to about 20 weight percent, or about 5 to about 20 weight percent, or about 10 to about 20 weight percent, or about 10 to about 15 weight percent, or about 5 weight percent, or less than about 5 weight percent of the cryoprotective composition(s).

In some examples, the cryoprotectant agent can be relatively transparent to ultrasound, so as not to interfere with ultrasonic imaging (e.g., images from a transrectal ultrasound probe) used to guide injection of the cryoprotective composition. As used herein, "relatively transparent to ultrasound" means a material having a relative transmissivity of at least about 88% or ranging from about 88% to about 100% for a frequency range of from about 4 MHz to about 10 MHz using the method for determining relative transmissivity in Poltawski, L., & Watson, T. (2007), *Relative transmissivity of ultrasound coupling agents commonly used by therapists in the UK, Ultrasound in medicine & biology,* 33(1), 120-128.

The cryoprotective composition(s) comprising the cryoprotectant agent(s) can have a thermal conductivity similar to water. For example, the thermal conductivity can be less than about 150% of water, which is 598.03 mW/mK at 20° C., 555.75 mW/mK at 0.01° C. For example, thermal conductivity of the cryoprotective composition(s) can be less than about 900 mW/mK between 0.01 and 20° C., as measured by ASTM standard D7896 (Transient Hot Wire Liquid Thermal Conductivity Method).

The cryoprotectant agent is configured to be mixed with the fluid agent prior to or during application of the cryoprotective composition(s) to the body space of the patient. As used herein, "non-toxic" means that the cryoprotectant agent should be of limited cellular and neurological toxicity to a patient so that it does not appreciably damage body tissues, such as skin, nerves, organs, and/or nerve bundles for patients or plant tissues for plants, when deposited or injected into the body or applied to external portions of the body. Cellular toxicity (i.e., toxicity to cellular or body tissues) is measured by the viability of cells after exposure to the cryoprotectant agent (under specific time and temperature). The viability is measured using membrane integrity dye (e.g., Trypan Blue) and metabolic activity assay (e.g., CCK8 assay). As used herein, for body tissues, a "non-toxic" cryoprotectant agent means a cryoprotectant agent having no more than a 50% decrease of "viability" and/or that at least 50% of a tissue sample treated with the cryoprotectant agent remains viable compared to a sample treated under the same conditions with saline (e.g., phosphate-buffered saline (PBS)). As used herein, maintaining "viability" or "viable" means that cells, tissues, or nerves retain or regain an ability to perform an intended function following removal of a damaging condition, such as removal of exposure to cold or freezing temperature. Neurological toxicity is measured with the electrically evoked compound action potential (eCAP) methods. As used herein, for nerves, a "non-toxic" cryoprotectant agent refers to a cryoprotectant agent having no more than a 50% decrease of action potential amplitude (compared to a sample treated under the same conditions with Krebs solution). Thus, nerve tissues are or remain viable when nerves of the tissue sample show no more than a 50% decrease of action potential amplitude (compared to a sample treated under the same conditions with Krebs solution). Exposure condition for evaluating toxicity of nerve tissue is defined as 30 min at 37° C.

Various cryoprotectant agents that can be used with the cryoprotective composition(s) of the present disclosure are described in Elliott, G. D., Wang, S., & Fuller, B. J. (2017). *Cryoprotectants: A review of the actions and applications of cryoprotective solutes that modulate cell recovery from ultra-low temperatures. Cryobiology,* 76, 74-91, which is hereby incorporated by reference. Non-limiting examples of cryoprotectant agents can comprise at least one of: alcohol(s) and/or derivative(s) thereof (e.g., methanol, ethanol, glycerol, propylene glycol, and/or ethylene glycol); sugar(s) and/or sugar alcohol(s), (e.g., monosaccharides and/or disaccharides, for example, glucose, galactose, lactose, fructose, sucrose, trehalose, raffinose, mannitol, and/or sorbitol); polymer(s) (e.g., polyethylene glycol, polyvinyl pyrrolidone, milk proteins, serum proteins, and/or peptones); polysaccharides (e.g., dextrans, Ficoll, and/or hydroxyethyl starch); sulfoxides (e.g., Dimethyl sulfoxide (DMSO)); amides (e.g., acetamide, formamide, and/or Dimethylacetamide); and amines (e.g., proline, glutamine, and/or betaine).

In some examples, the cryoprotective composition(s) can comprise solutions or mixtures comprising, but not limited to: 3-OMG (3-O-methyl-D-glucose); DP6 (3.0M dimethylsulfoxide ($Me_2SO$)+3.0M 1,2-propanediol (DP)); VS55 (a vitrification solution comprising DMSO, formamide, and propylene glycol); and/or M22. M22 is a cryoprotectant agent solution comprising: Dimethyl sulfoxide (22.305 w/v %); formamide (12.858 w/v %); ethylene glycol (16.837 w/v %); N-methylformamide (3 w/v %); 3-methoxy-1,2-propanediol (4 w/v %); polyvinyl pyrrolidone K12 (2.8 w/v %); X-1000 ice blocker (1 w/v %); and Z-1000 ice blocker (2 w/v %).

In some examples, the cryoprotective composition(s) can comprise less than 20%, less than 10%, less than 5%, or less than 1% by weight of Dimethyl sulfoxide (DMSO) and/or ethylene glycol, or about 1 to about 20 weight percent, or about 5 to about 15 weight percent, or less than about 10 weight percent of DMSO and/or ethylene glycol, or is free of DMSO and/or ethylene glycol to avoid nerve damage.

In some examples, the cryoprotectant agent can comprise molecule(s), compound(s) and/or polymer(s) that resist freezing below a temperature of about negative 15° C. to about 0° C., or about negative 10° C. As used herein, "polymers" or "polymer compositions" comprise, without limitation, homopolymers, heteropolymers, co-polymers, block polymers, block co-polymers, and can be both natural and/or synthetic. A polymer "comprises" or is "derived from" a stated monomer if that monomer is incorporated into the polymer. Thus, the incorporated monomer (monomer residue) that the polymer comprises is not the same as the monomer prior to incorporation into a polymer, in that at the very least, certain groups are missing and/or modified when incorporated into the polymer backbone. For example, the cryoprotectant agent comprising a polymer can comprise one or more of polyethylene glycol, polyvinyl pyrrolidone, milk proteins, serum proteins, peptones, dextrans, Ficoll, or hydroxyethyl starch.

In some examples, the cryoprotective composition(s) can further comprise additional materials to adapt the cryoprotective composition(s) for particular uses. For example, the cryoprotective composition(s) can comprise Krebs phosphate solution for improving distribution of the cryoprotectant agent through the other components of the cryoprotective composition(s). In some examples, the amount of Krebs phosphate solution in the cryoprotective composition(s) can range from about 1.0 weight percent to about 95 weight percent, or about 5.0 weight percent to about 90 weight percent of the cryoprotective composition(s).

In some examples, the cryoprotective composition(s) can comprise multiple cryoprotectant agents. For example, the cryoprotective composition(s) can comprise 5.0 weight percent DMSO+0.2M trehalose in Krebs solution, 5.0 weight percent DMSO+0.4M trehalose in Krebs solution, or 10 weight percent DMSO+0.2M trehalose in Krebs solution.

As discussed previously, in some other examples, the cryoprotective composition(s) comprises a topical cryoprotective composition configured to be applied to skin. In such examples, the cryoprotective composition can comprise the biodegradable and/or bioerodible fluid agent and the non-toxic cryoprotectant agent. The topical cryoprotective composition(s) can be configured to protect skin from damage caused by environmental conditions, such as exposure to cold or freezing, for example, by exposure to cryotherapy agents. In some examples, the cryoprotective composition(s) can be configured to protect the skin from frostbite. As used herein, "substantial damage" to the skin means frostbite, such as frostnip, superficial frostbite, and/or deep frostbite, and can comprise damage to the epidermis, dermis, and/or subcutaneous tissue, redness, skin whitening, blisters, and/or numbness. The topical composition can also include other components and compositions commonly used for lotions, balms, solutions, and compositions that are applied to skin including, for example, water, oil(s), alcohol(s), propylene glycol(s), wax(es), preservatives, emulsifiers, antimicrobials, absorption promoters, and/or fragrances.

As previously discussed, in some examples, the cryoprotective composition(s) can also be applied to plants by coating, spraying, immersion, or any other application method. The cryoprotective composition(s) for plants can be configured to protect surfaces of the plants from environmental conditions, such as exposure to cold or freezing temperatures or frozen materials, such as precipitation (e.g., ice or snow). The cryoprotective composition(s) for plants can also include other components and compositions commonly applied to plants including, for example, micronutrients, macronutrients, pesticides, insecticides, herbicides, rodenticides, fungicides, biocides, plant growth regulators, fertilizers, microbes, soil additives, adhesion promoting-agents, and/or surfactants, as are known in the art.

Methods for Performing Cryotherapy Procedures

As previously described, the cryoprotective composition(s) can be used in various cryosurgical procedures comprising, for examples, treatment of prostate cancer and/or for destruction and removal of other cancers and/or tumors. In some examples, a method for preparing a surgical site, for protecting the surgical site during cryosurgery, and/or for performing cryosurgery comprises injecting a therapeutically effective amount of any of the previously described cryoprotective compositions into a body space, such as into a periprostatic space 10 (shown in FIGS. 2A-4B) surrounding the prostate of a patient. In some examples, the protective composition(s) is injected after the cryotherapy probes are positioned in the target tissue(s). Alternatively, the protective composition(s) may be applied prior to introducing the cryotherapy probes to the target tissue(s). As shown in FIGS. 2A-4B, the periprostatic space 10 is defined by or comprises the prostate 12, rectum 14, neurovascular bundle 16, and bladder 18. As described in further detail herein, therapeutically effective amounts (shown generally by reference numbers 28 and 36) of the cryoprotective composition(s) are injected into the periprostatic space 10 to protect the prostate 12 and neurovascular bundle 16 during cryosurgical procedures.

As previously discussed, the cryoprotective composition(s) comprises, for example, the at least one biodegradable and/or bioerodible fluid agent and the at least one non-toxic cryoprotectant agent. The cryoprotective composition is desirably of sufficient viscosity to remain within a body space, such as the periprostatic space 10, for a duration sufficient for performing a cryosurgical procedure in proximity to the body space. Desirably, the cryoprotective composition does not cause substantial nerve damage when positioned in the body space for the duration of the cryosurgical procedure.

As previously discussed, as used herein, a "therapeutically effective amount" means an amount of the cryoprotective composition(s) sufficient to protect surrounding tissues from cold created by cryotherapy agents used during cryosurgery, for example, to prevent and/or inhibit freezing of cellular structures of the surrounding tissues. This prevention and/or inhibition of freezing can be a result of physical spacing between target tissues and surrounding tissues created by the injected cryoprotective composition(s) and/or cryoprotective or antifreeze properties of the cryoprotective composition(s). For example, when the cryoprotective composition(s) is used for cryosurgery of the prostate, the "therapeutically effective amount" of the cryoprotective composition may be an amount of the cryoprotective composition(s) sufficient to preserve an ability of nerves of the neurovascular bundle 16 to generate action potentials. For example, for a cryosurgical procedure for the prostate 12, it is expected that from about 1.0 mL to about 100 mL, or about 5.0 mL to about 75 mL, or about 10 mL to about 50 mL, or more of the cryoprotective composition(s) may be needed to provide appropriate protection for the prostate 12 and neurovascular bundle 16. One of ordinary skill in the art understands that the amount of the cryoprotective composition(s) injected to the surgical site can vary based upon the size of the area/volume to be protected.

Figure 5:
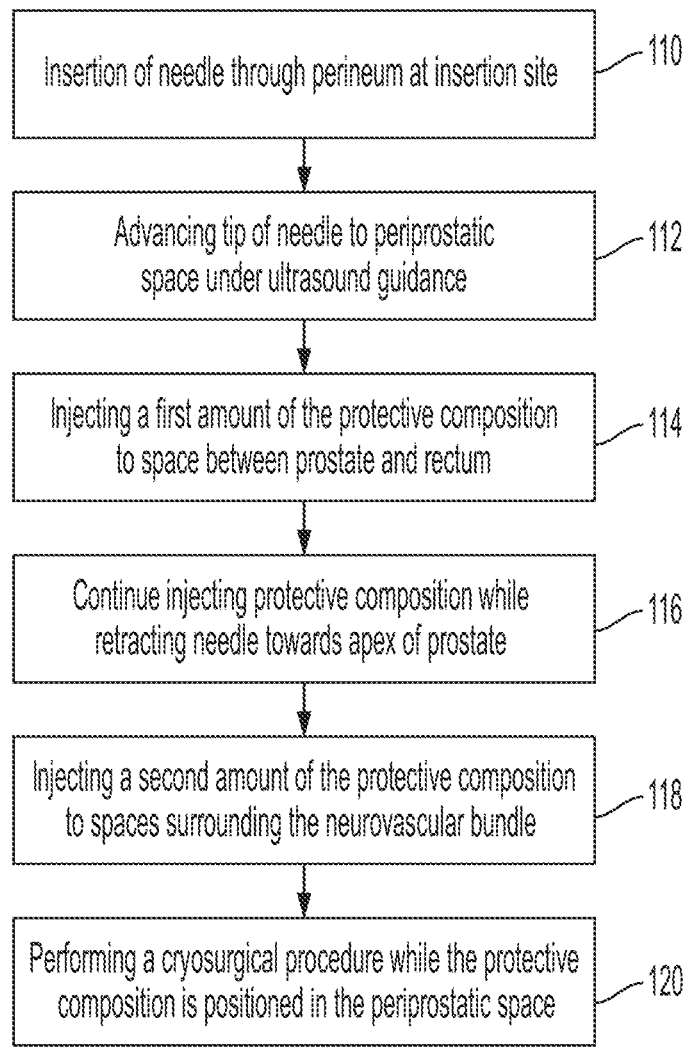
FIG. 5 is a flow chart showing a surgical method using the cryoprotective composition(s) of the present disclosure.

With reference to FIG. 5, in some examples, the injection of the cryoprotective composition comprises, at step 110, inserting a tip 20 of a syringe needle 22 (shown in FIGS. 2A and 2B) through a perineum region 2 of the patient at, for example, the midline position (shown by dashed line 4) extending from the anus 6 to the scrotum 8, as shown in FIGS. 1A and 1B. The proposed injection site is shown by reference number 34 in FIGS. 1A and 1B. As previously discussed, in some examples, the cryoprotective composition(s) is applied after the cryotherapy probes are in place. Alternatively, the cryoprotective composition(s) can be applied prior to insertion of the cryotherapy probes to the target tissues of the prostate 12. For cryosurgical procedures for the prostate 12, the patient is in the lithotomy position. As used herein, the "lithotomy position" refers to a position with the patient lying on his back with the legs flexed 90 degrees at the hips. The patient's knees are bent at 70 to 90 degrees and padded footrests attached to the table support the patient's legs. A size of the needle 22 can, for example, range from an 18 gauge needle to a 22 gauge needle, though one of ordinary skill in the art may select an appropriately needle size depending upon, for example, the type of surgical procedure being performed, the amount of the cryoprotective composition(s) needed to provide sufficient protection for surrounding tissues and structures, and viscosity and other characteristics of the cryoprotective composition(s) being injected.

Figure 2A:
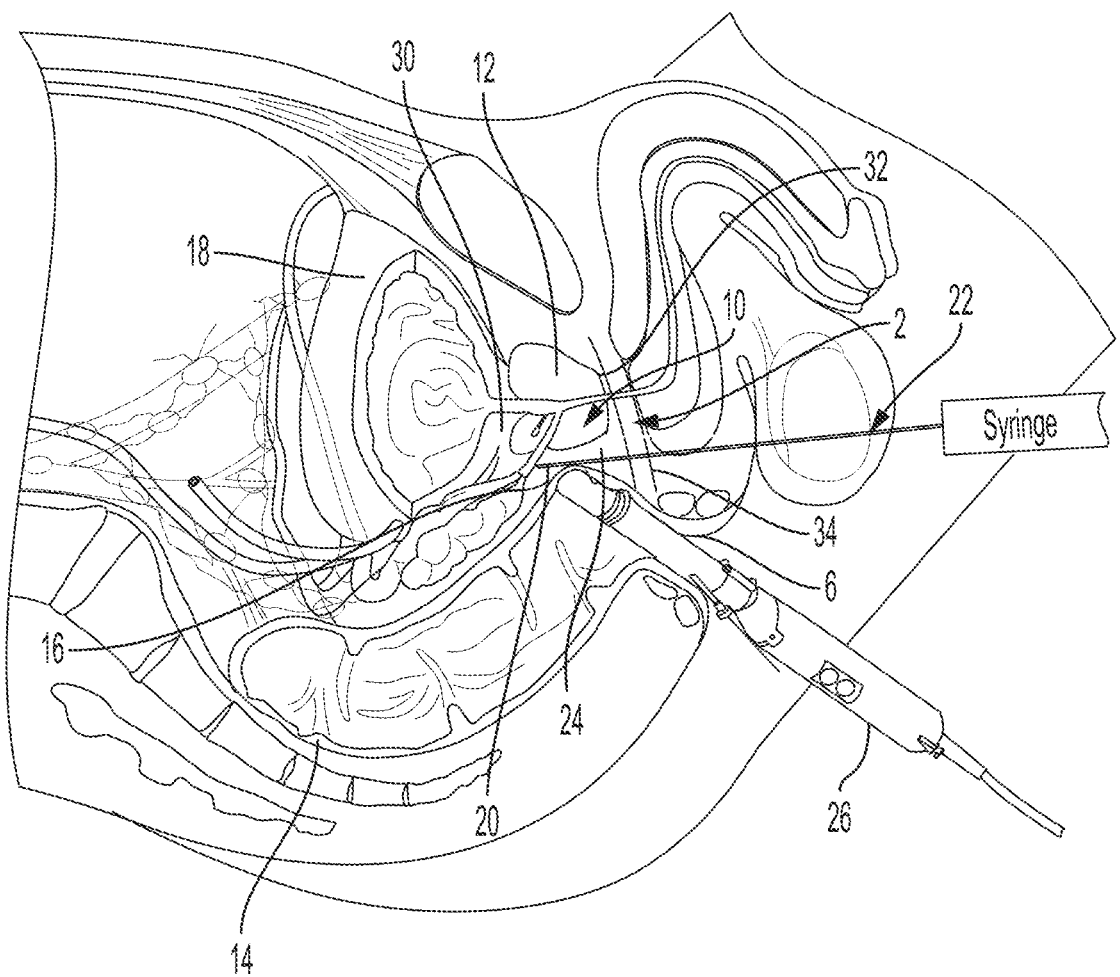
FIGS. 2A and 2B are schematic drawings of anatomical structures of the periprostatic space showing insertion of the needle for injecting the cryoprotective composition(s) of the present disclosure.
Figure 2B:
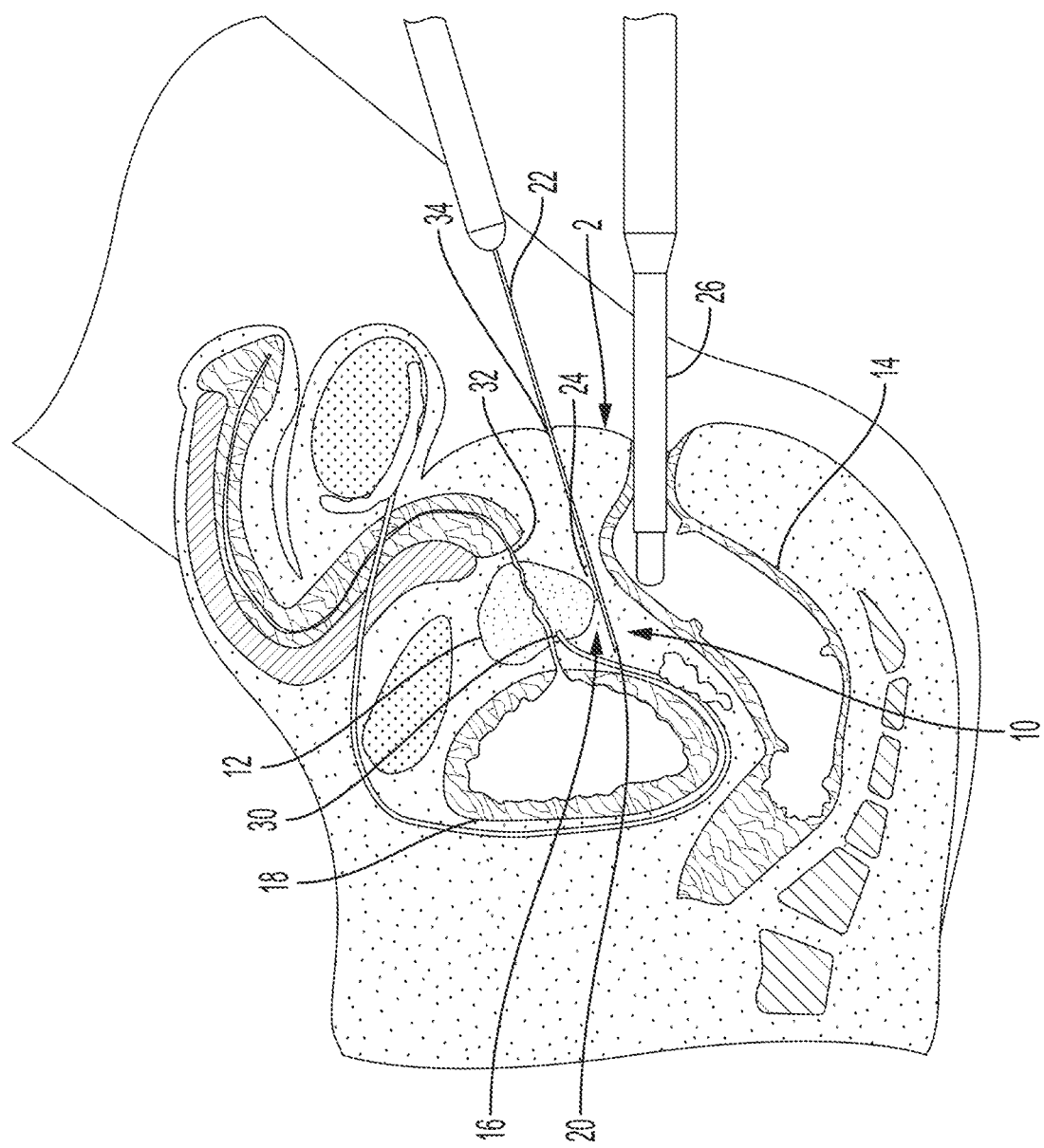
Figure 3A:
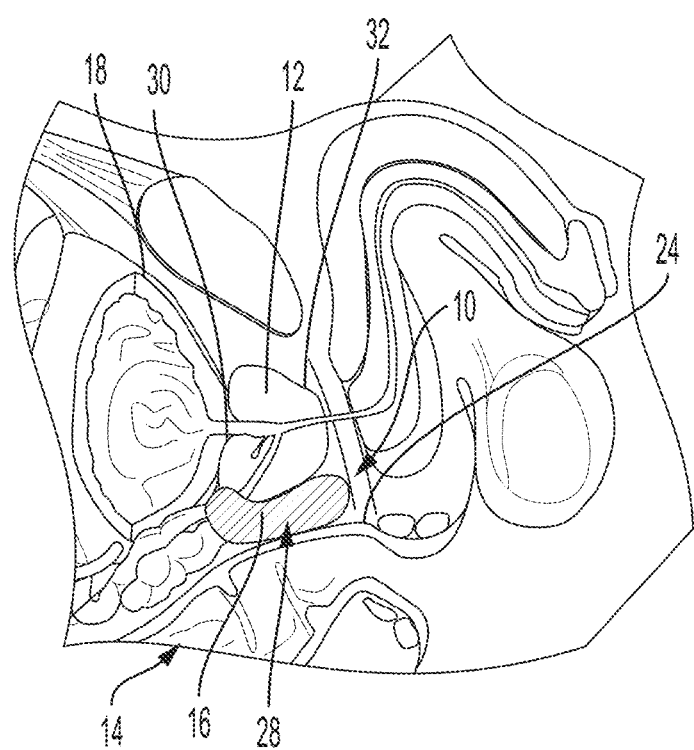
FIGS. 3A and 3B are schematic drawings of the periprostatic space showing an amount of the cryoprotective composition(s) dispersed between the prostate and rectum near the base of the prostate.
Figure 3B:
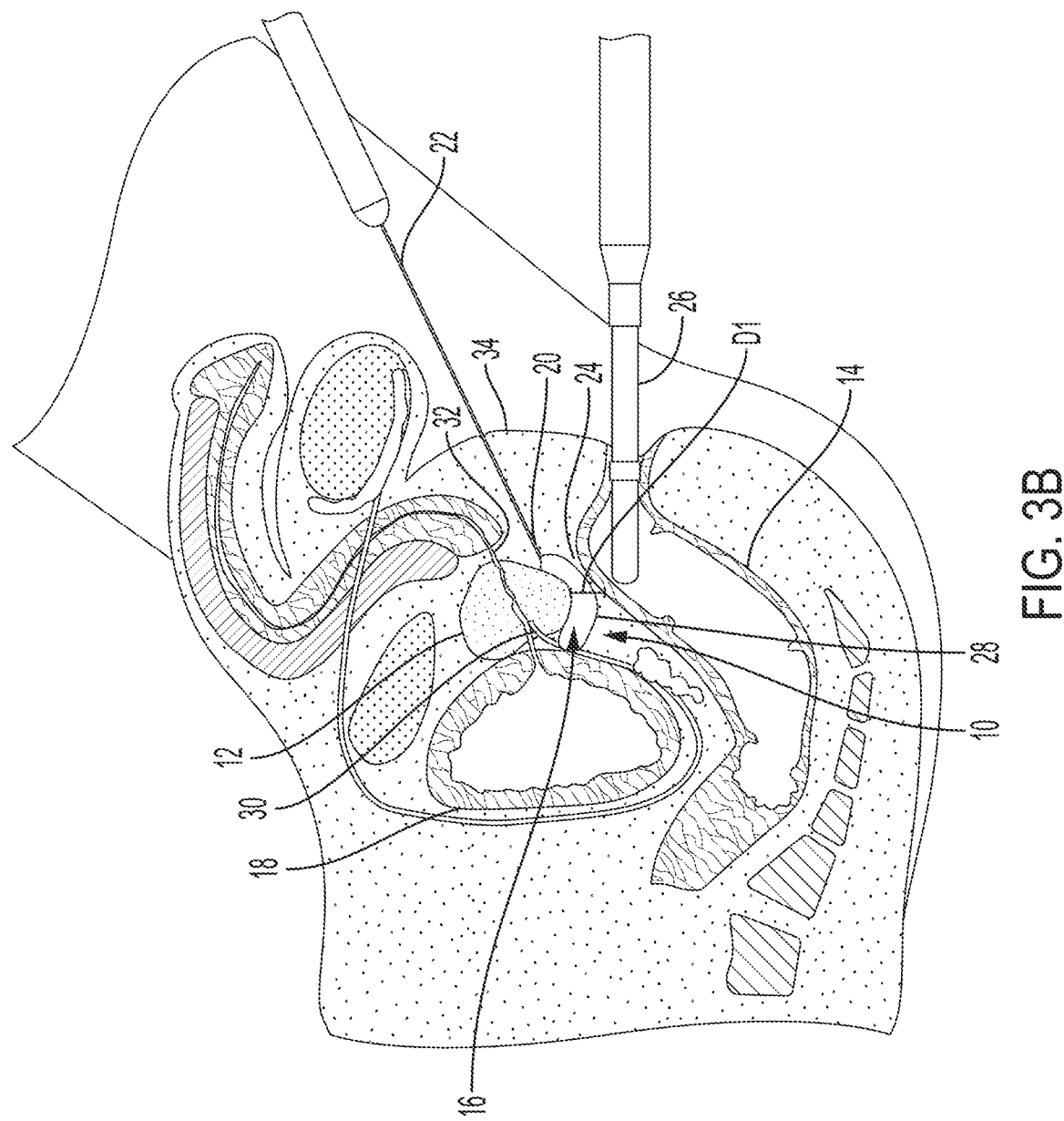
Figure 4A:
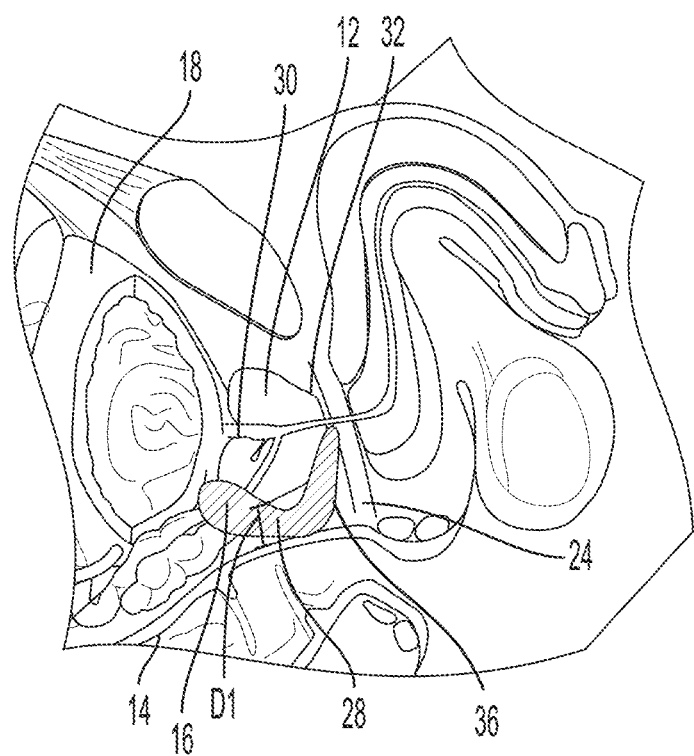
FIGS. 4A and 4B are additional schematic drawings of the periprostatic space showing an additional amount of the cryoprotective composition(s) applied laterally about the prostate creating additional space between the prostate and rectum.
Figure 4B:
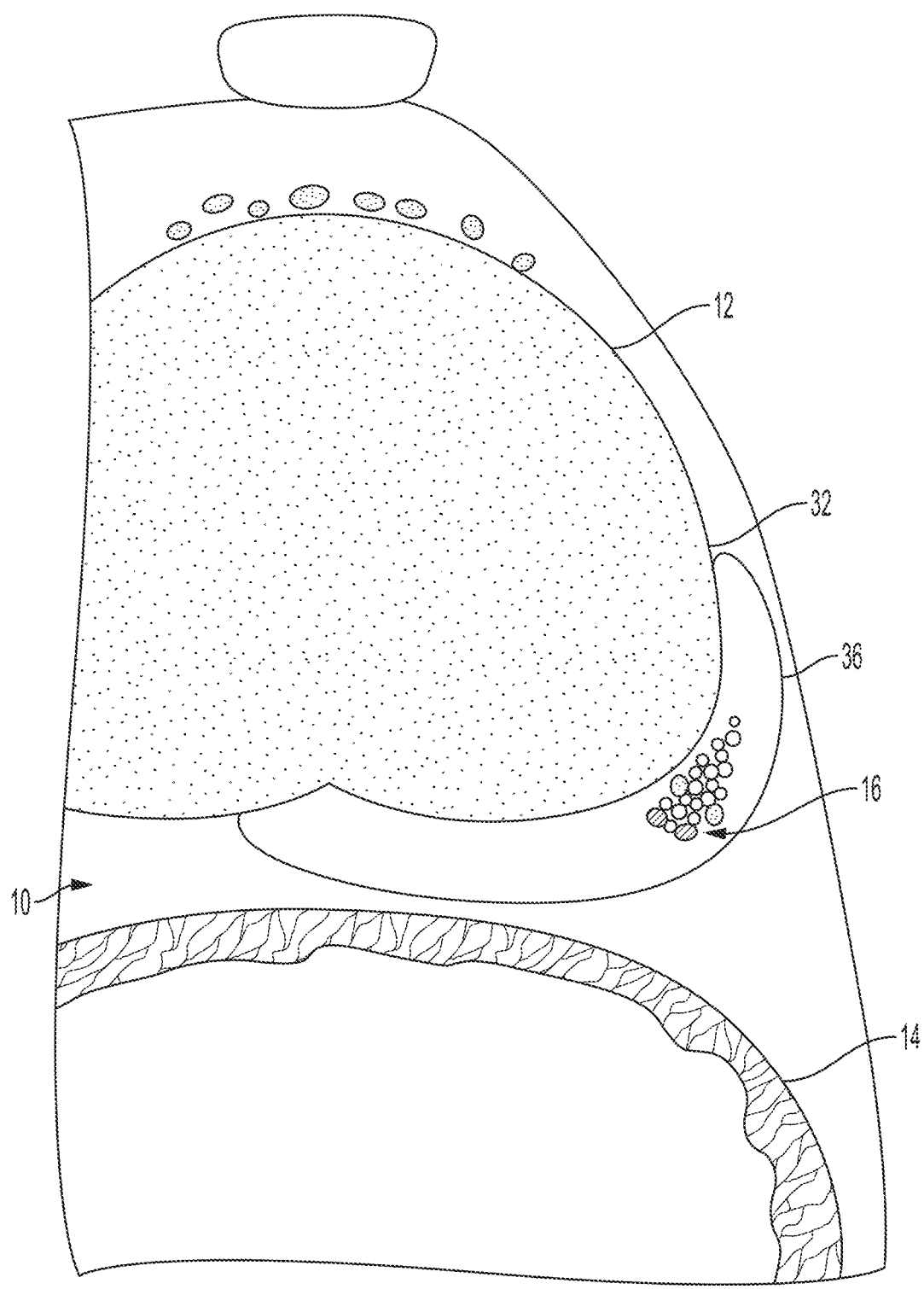

At step 112, under ultrasound guidance, the method comprises advancing the tip 20 of the needle 22 from the insertion site 34 in the perineum region 2 to perforate the Denonvillier's fascia extending between the prostate 12 and rectum 14 (shown generally by reference number 24) of the periprostatic space 10 distal to the prostate 12. Ultrasound guidance can be provided, for example, by a transrectal ultrasound probe 26, as shown in FIGS. 2A and 2B, inserted into the rectum 14 of the patient.

At step 114, the method further comprises injecting a first amount 28 of the cryoprotective composition(s) to a portion of the periprostatic space 10 between the prostate 12 and the rectum 14 near a base 30 of the prostate 12. The first amount 28 of the cryoprotective composition(s) is shown schematically in FIGS. 3A and 3B. At step 116, the method further comprises continuing to inject the first amount 28 of the cryoprotective composition(s) from the tip 20 of the needle 22 while retracting the needle 22 from the base 30 of the prostate 12 towards an apex 32 of the prostate 12. It is believed that the space created by this initial injection of the cryoprotective composition(s) (e.g., the first amount 28 of the cryoprotective composition shown in FIGS. 3A and 3B) allows for easy movement of the needle 22 in the periprostatic space 10, thereby enabling further injection laterally to regions surrounding the prostate 12 and neurovascular bundle 16. For example, the first amount 28 of the cryoprotective composition can create a space or distance D1 (shown in FIG. 4A) between the lower surface of the prostate 12 and an upper surface of the rectum 14. In order to provide suitable protection for tissues of the rectum 14 during cryosurgery and/or to permit lateral movement of the needle 22 towards the neurovascular bundle 16, the distance D1 can be from about 1.0 mm to about 50 mm or from about 5.0 mm to about 20 mm.

When the first amount 28 of the cryoprotective composition is released into the periprostatic space 10, the cryoprotective composition covers spaces between the base 30 and an apex 32 of the prostate 12. At step 118, the method can further comprise moving the tip 20 of the needle 22 laterally while injecting a second amount (shown generally be reference number 36 in FIGS. 4A and 4B) of the cryoprotective composition to cover additional portions of the prostate 12 and to more fully surround portions of the neurovascular bundle 16. In addition to moving the needle 22 laterally, the needle 22 may also be inserted or retracted to obtain desired coverage of the prostate 12. Once the first amount 28 and the second amount 36 of the protective composition(s) is applied to the periprostatic space 10 and the prostate 12, the cryoprotective composition may substantially or fully envelop the prostate 12, providing suitable protection for structures surrounding the prostate 12. In other examples, the cryoprotective composition may only be applied in proximity to selected areas or portions of the prostate 12 dependent upon the type of localized procedure being performed. For many surgical procedures, it is expected that following injection of the first amount 28 and the second amount 36, the protective composition(s) will cover from about 10% to about 90%, or about 50% to about 75%, or about 60% to about 70% of the surface of the prostate 12.

As discussed previously, the cryoprotective composition comprises the biodegradable and/or bioerodible fluid agent. The fluid agent is configured and/or selected to remain in place within the periprostatic space 10 for a duration of the cryosurgical procedure. For example, the duration of the surgical procedure (e.g., duration that the cryoprotective composition remains at its injection location) can be, for example, from about 10 minutes to about 5 hours, from about 20 minutes to about 2 hours, or from about 30 minutes to about 2 hours.

At step 120, a method for cryosurgery further comprises, following injection of the therapeutically effective amount of the cryoprotective composition to the selected portions of the periprostatic space 10, performing a cryosurgical procedure while the cryoprotective composition is positioned in the periprostatic space 10. As discussed herein, the cryosurgical procedure can be a cryosurgical procedure for removal or destruction of cancerous tissue in the prostate, such as tumor ablation or any cryosurgical procedure.

As discussed herein, the cryoprotective composition(s), method(s) of preparing a surgical site, and surgical method(s) of the present disclosure can also be used for treatment of conditions and/or for use with other surgical procedures in addition to treatment of prostate cancer and/or removal of tumor(s) from the prostate. For example, the cryoprotective composition(s) can be used with surgical methods for destruction or removal of solid masses comprising, for example, tumor(s) and/or cancer (e.g., metastasized tumor(s) and/or primary tumor(s)) located in the lungs, liver, kidney, adrenals, breast, and/or skin of the patient. In some examples, the cryoprotective composition(s) can be used with cryosurgical methods for treating one or more of cardiac arrhythmia, ablation of aberrant nerves in proximity to a pulmonary artery, tumor(s) and/or lesions around an eye or eye orbit, esophageal tumor(s) and/or cancer, pancreatitis, pancreatic tumor(s) and/or cancer, rectal proctitis, liver tumor(s) and/or cancer, brain tumor(s) and/or cancer, cryolipolysis, chronic pain caused by trigeminal neuralgia, neurologic pain at various regions in the body, and/or organ transplantation.

In some examples, the protective composition(s) can be applied to external portions of the body tissue, such as all or a portion of the skin of a patient. For example, the protective composition(s) can be applied before or during, for example, cryolipolysis in order to preserve the appearance of the skin. Specifically, in cryolipolysis, the outer appearance of the skin should be preserved while freezing fatty tissue below the skin. It is believed that the protective composition(s) can provide such protection for outer layers of skin without interfering with freezing of fat cells in proximity to the skin. The protective composition may also be added to skin creams or lotions and applied, for example, to reduce risks of exposure to cold and to avoid developing frostbite.

Methods of Use for Topical Cryoprotective Compositions

In some examples, as previously described, the cryoprotective composition is a topical composition that is applied to skin to protect the skin from exposure to environmental conditions, such as freezing temperatures or wind. The topical composition can be applied to skin in a manner similar to how other topical compositions and locations are applied to skin. For example, a user or patient can obtain a container, such as a bottle, tube, vial, or another suitable container holding the composition. The user can apply the cryoprotective composition directly to the skin by, for example, squeezing the composition from a tube or pouring the composition from a bottle onto the skin. The user or patient can then rub or otherwise disperse the composition over a surface of the skin to ensure appropriate coverage for any areas of skin exposed to harsh environmental conditions. In order to ensure proper protection, the cryoprotective composition may be periodically reapplied, such as one ever few hours.

Methods for Applying a Cryoprotective Composition to Plants

As previously described, in some examples, the cryoprotective composition(s) can be used to protect internal or external tissues of plants from exposure to cold temperatures. In some examples, a method for applying the cryoprotective composition to a plant to protect the plant from frost and/or freezing can comprise coating at least a portion of a surface of the plant with the cryoprotective composition. The plant can be, for example, a fruit tree, citrus tree, grape vine, flowering tree, flowering bush, grasses, hay, grains, corn, or any other plant that may be exposed to freezing temperatures. Applying the cryoprotective composition to the surface of the plant can include applying the cryoprotective composition to, for example, leaves, stems, buds, flowers, or fruit of the plant. In some examples, the composition can also be applied to roots of the plant. Portions of the applied composition in proximity to the roots can be absorbed by the roots, thereby introducing the cryoprotectant agent into internal structures or tissues of the plant. Once absorbed by the plant, the cryoprotectant agent can protect internal tissues of the plant from cold temperatures, freezing, or frost. For some plants, components of the cryoprotective composition can also be absorbed by leaves, stems, or flowers of the plant, or by any other portion of the plant capable of absorbing liquids, emulsions, or solutions.

In some examples, applying the cryoprotective composition to surfaces of the plant can include coating surfaces of the plant with the composition by, for example, spraying the composition over the surface of the plant, pouring the composition over the surface of the plant, or immersing a portion of the plant in a bath of the cryoprotective composition. For example, roots of the plant may be immersed in a bath of the cryoprotective composition so that the composition can be absorbed into interior tissues of the plant.

EXPERIMENTAL EXAMPLES

To evaluate cryoinjury of the nerves and cryoprotection effectiveness of the cryoprotective composition(s) disclosed herein, the present inventors have performed the following examples.

Example 1: Establishment of the NVB Temperature Profile and Models for Cryoprotectant Agent Loading 3D models of the prostates were created from image data showing prostate cancer (PCa). Tumor locations and cryoprobes were placed in analogy to clinical cases based on surgical experience. Freezing cycles were then performed that mirror clinical processes. The 3D models were generated from a heat transfer finite element model (FEM) used to derive a spatial-temporal temperature distribution across the prostate and adjacent tissue. The temperature histories of the neurovascular bundle (NVB) under various cryosurgery scenarios were then created according to the generated models. The created temperature histories were then used for testing of different cryoprotectant agents (in Example 2) in order to model effectiveness and toxicity of the different cryoprotectant agents based in realistic clinical applications.

Figure 6B:
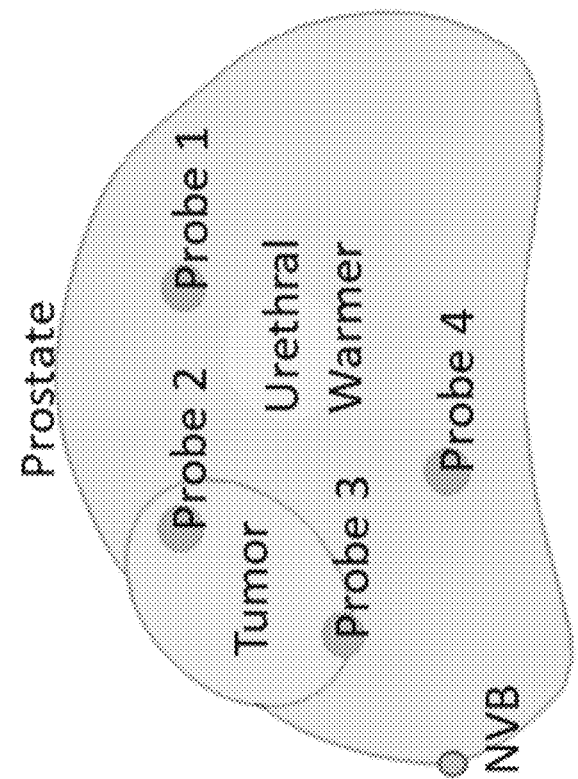
FIGS. 6A and 6B are examples of 3D prostate models created from image data of prostates with prostate cancer, according to an example of the present disclosure.
Figure 6A:
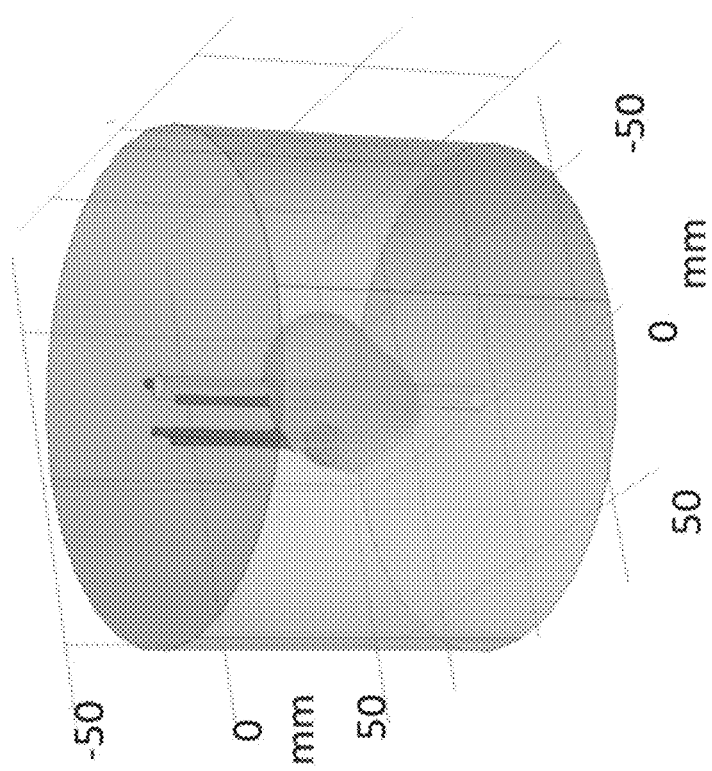
Figure 7E:
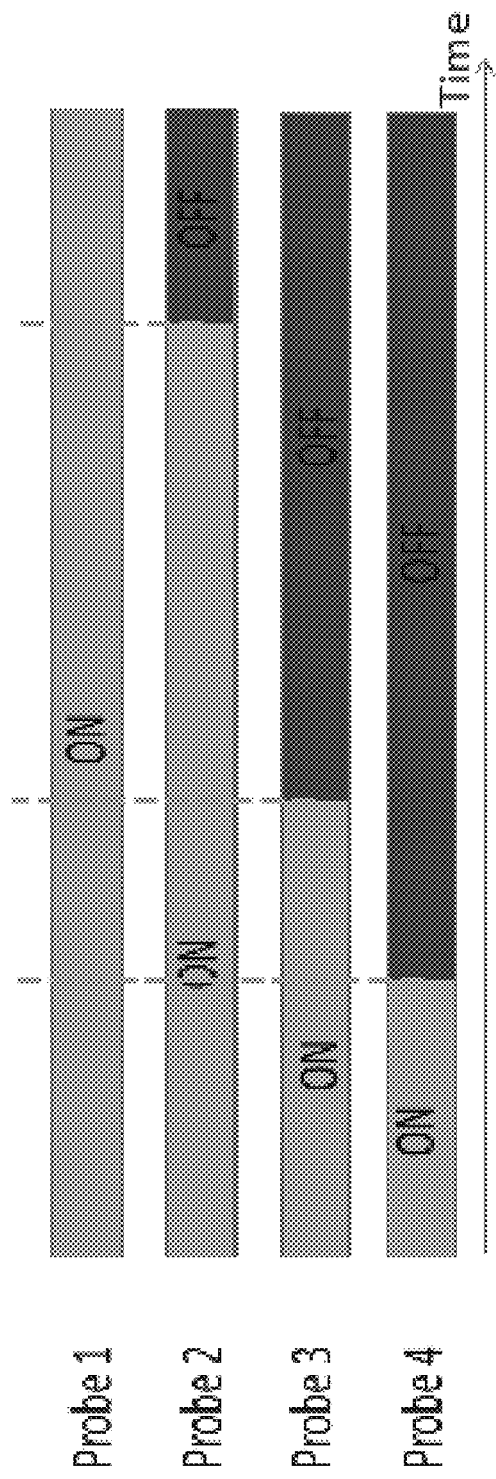
FIG. 7E is a graph showing timing of turning cryoprobes on and off for cryoprobes used during a cryosurgical procedure, according to an example of the present disclosure.

More specifically, in order to produce the 3D models of the prostate, MR images were imported using native Digital Imaging and Communications in Medicine (DICOM) data files that were converted to 3D renditions. The tumor regions within the prostate and the placement of cryoprobes were annotated in analogy to clinical cases based on a surgeon's experience. The DICOM files were viewed in 3D Slicer as segmented prostate regions. The 3D prostate model was converted to Standard Triangle Language (STL) format and imported into COMSOL Multiphysics® simulation software, which is a proprietary finite element analysis and modeling software program produced by COMSOL Inc. (Stockholm, Sweden). The size, shape, and location of the tumors were marked in the 3D prostate model, as well as the actual locations and real-world geometries of the cryoprobes. A urethral warming catheter, through which warm saline continuously flows during a surgical procedure, was also included in the model. The topographical anatomy and distribution of the NVB were modeled by computerized planimetry and diffusion tensor imaging (DTI). Examples of a PCa cryosurgery model reconstructed based on data for the created image files are shown in FIGS. 6A and 6B.

It is recognized that characterization of the cryoprobe is necessary for accurately recreating the cryosurgical process in the model. Therefore, in order to accurately model boundary conditions, the distributed cryogen temperature and convective coefficient were adjusted to match the temperatures at various locations around the cryoprobes and the locations of the 0° C., −20° C., and −40° C. isotherms using known methods, as described in Etheridge, et al., "Methods for Characterizing Convective Cryoprobe Heat Transfer in Ultrasound Gel Phantoms", *J Biomech Eng.*, February 2013, 135(2), and as shown in FIGS. 7A-7D for one specific cryoprobe model.

A heat transfer finite element method (FBM) was then used to derive the spatial-temporal temperature distribution across the prostate and adjacent tissue. In the simulation, the cryoprobes of a selection of models were turned "on" and "off" based on the timings from the surgical records. The timings for the cryoprobes are shown schematically in FIG. 7E. Pennes' bioheat equation was used as the governing equation for the analytical solution of the temperature distribution. The phase changes occurring during the freezing process were modeled based on an enthalpy method and the thermal properties were derived from the literature.

Figure 8B:
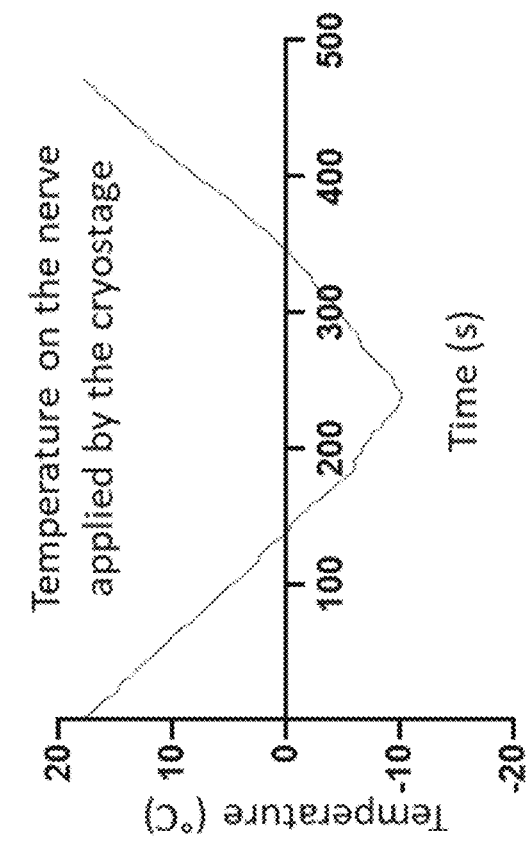
FIG. 8B is a temperature profile applied by a cryostage device during ex vivo testing of nerves used for the examples of the present disclosure.
Figure 8A:
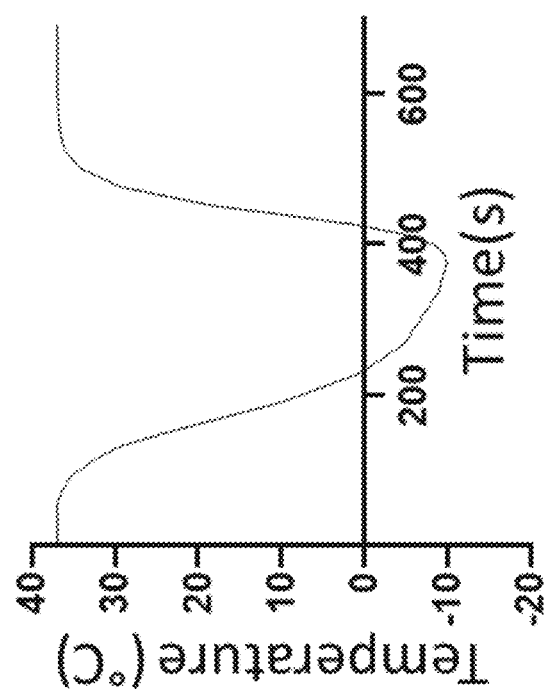
FIG. 8A is a graph showing a temperature of the neurovascular bundle determined from a computer-generated model for a cryosurgical procedure performed for the prostate.

It is believed that the simulations described hereinabove for recreating PCa cryosurgeries simulate conditions that the NVB is subjected to during surgery, which provides a temperature history of the NVB throughout the surgical process. Accordingly, the generated model was used to determine a time-dependent graph of temperatures to which the NVB is exposed to during prostate surgery. An exemplary generated time-dependent graph created from the 3D model is shown in FIG. 8A. As shown in FIG. 8A, in the modeled example, it was determined that the temperature of the NVB was as low as −10° C. with a cooling rate of about −10° C./min. These simulated NVB temperature histories were validated against temperature records collected during cryosurgery procedures. The time-dependent graph was used to control temperatures applied to nerves during ex vivo testing, as described hereinafter. Specifically, a graph showing temperatures on the nerves applied by a cryostage device over a testing cycle is shown in FIG. 8B.

Example 2: Assessment of Acute Nerve Cryoinjury and Recovery with the Cryoprotectant Agent Ex vivo models were used to determine the cryoinjury threshold and to quantify the extent of cryoinjury mitigation provided by the cryoprotective composition. Specifically, as described in further detail herein, fresh phrenic nerves procured from swine and fresh sciatic nerves from rats were dissected and verified for function.

Fresh nerves from swine and rats were selected by the inventors for ex vivo testing because such nerves are believed to be comparable to human anatomy. Several papers have investigated and compared the anatomy of nerves in humans to pigs, rats, or mice. For example, the following papers have addressed these issues: Stakenborg, et al., "Comparison between the cervical and abdominal vagus nerves in mice, pigs and humans," *Neurogastroenterology & Motility* (2020): 32; Ding, et al., "Anatomical anomalies of the laryngeal branches of the vagus nerve in pigs," *Laboratory Animals* (2012) 46:338-340; and Pelot, "Quantified Morphology of the cervical and subdiaphragmatic Vagus nerves of Human, Pig, and Rat," *Frontiers in Neuroscience* (2020) 14. Most of these studies focus on the vagus nerve because vagal nerve stimulation is evaluated as a novel approach to treat immune-mediated disorders, such as Crohn's disease. Nevertheless, the present inventors believe that these studies show that human nerves are comparable to porcine phrenic nerves and sciatic nerves of rats in terms of myelinated and unmyelinated fibers. In particular, the nerve composition is believed to be particularly comparable between humans and pigs leading to the conclusion that porcine nerves and nerves obtained from rats are a valuable substitute to human nerves. In particular, the Pelot article studied the morphology of nerve fibers in human, pigs, and rats in detail. Pelot observed a greater variability in human nerve morphology than pigs and rats. Porcine nerves were generally found to be slightly smaller in size than human nerves, but there were ten times more fascicles in the porcine nerve for the same size. The rat nerves were ten times smaller and had a smaller protective perineurium.

For these reasons, the present inventors consider porcine nerves as a valuable substitute for the nerve study. The fact that there are ten times more fascicles in the same nerve may also render it more suitable as a substitute of the human erectile nerves. It is believed that rat nerves are more vulnerable as they are of smaller size (10×) and less protected by the perineurium.

A compound action potential recording system coupled with an oxygenated bath was set up to assess the changes in nerve function due to injury and recovery over a period of 3 hours. A cryostage with precise control of the surface temperature and its rate of change was used to simulate the thermal conditions experienced by the neurovascular bundle during cryosurgery. The cryostage was configured to apply temperatures according to the temperature profile in FIG. 8B. During ex vivo testing, the phrenic and sciatic nerves were exposed to one of the following conditions: (i) cryoprotectant agent perfusion, (ii) freezing conditions, or (iii) both the cryoprotectant agent perfusion and the freezing conditions. The action potential of the nerves following exposure to the cryoprotectant agent and/or freezing was then measured. A series of cryoprotectant agents were evaluated in terms of toxicity and effectiveness in preserving action potentials of the neurovascular bundle using the ex vivo nerves.

Figure 9:
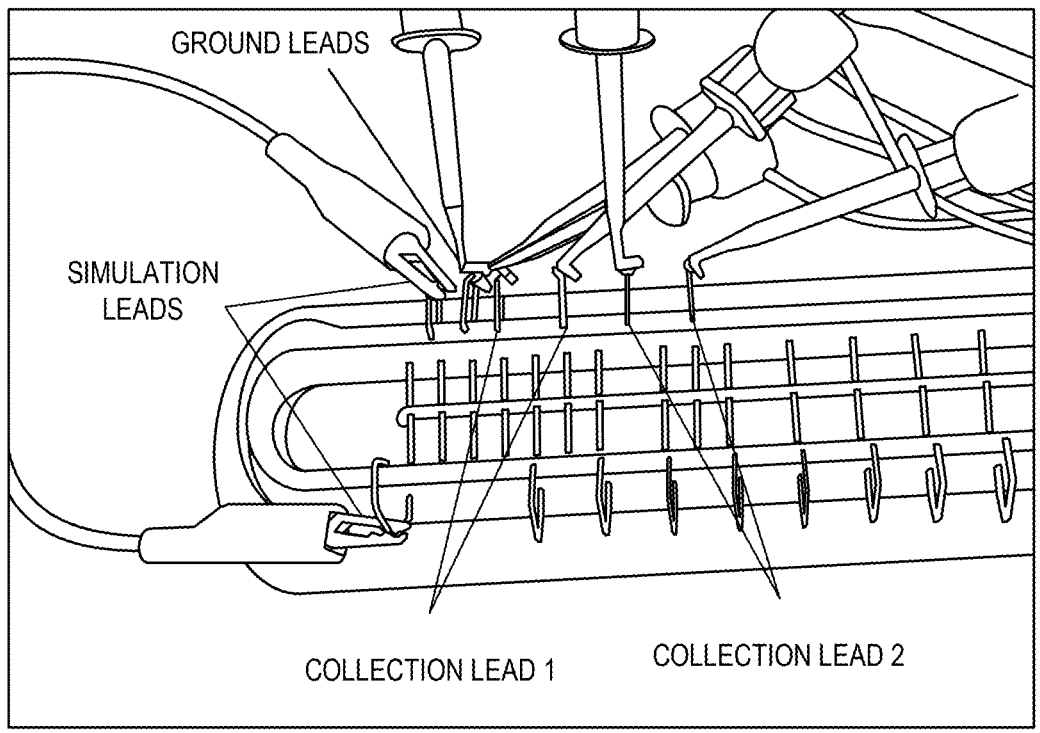
FIG. 9 is a photograph of a nerve and stimulation and measurement leads for testing nerves during examples of the present disclosure.

More specifically, in order to assess the extent of cryo-injury through ex vivo models, a bipolar compound action potential (AP) stimulation and recording system was constructed. The compound action potential recording system was a bipolar compound action potential stimulation and recording system based on well-established experiments from McGill University. See The McGill Physiology Virtual Lab, Compound Action Potential, http://www.medicine.mcgill.ca/physio/vlab/CAP/prep.htm. The system comprises: a series of electrodes in contact with the nerves; stimulation leads for evoking an action potential that travels down the nerves; and two pairs of collection leads for recording the action potential proximal and distal to the freezing site. Both the stimulation and recording of the action potential are synchronized with a computer. A procedure for preparation of the nerves is described in Goff, R. P., Bersie, S. M., & Iaizzo, P. A. (2014), *In vitro assessment of induced phrenic nerve cryothermal injury. Heart rhythm*, 11(10), 1779-1784. Specifically, two phrenic nerves were dissected from swine and placed in modified Krebs-Henseleit buffer (i.e., "Krebs solution"), after which fatty sheaths and connective tissue surrounding the nerves were removed. The prepared nerves were then placed in a nerve recording chamber. The nerves were exposed to a constant temperature of 37° C. and a constant supply of oxygen once placed in the chamber. A photograph of the system is shown in FIG. 9.

Figure 10:
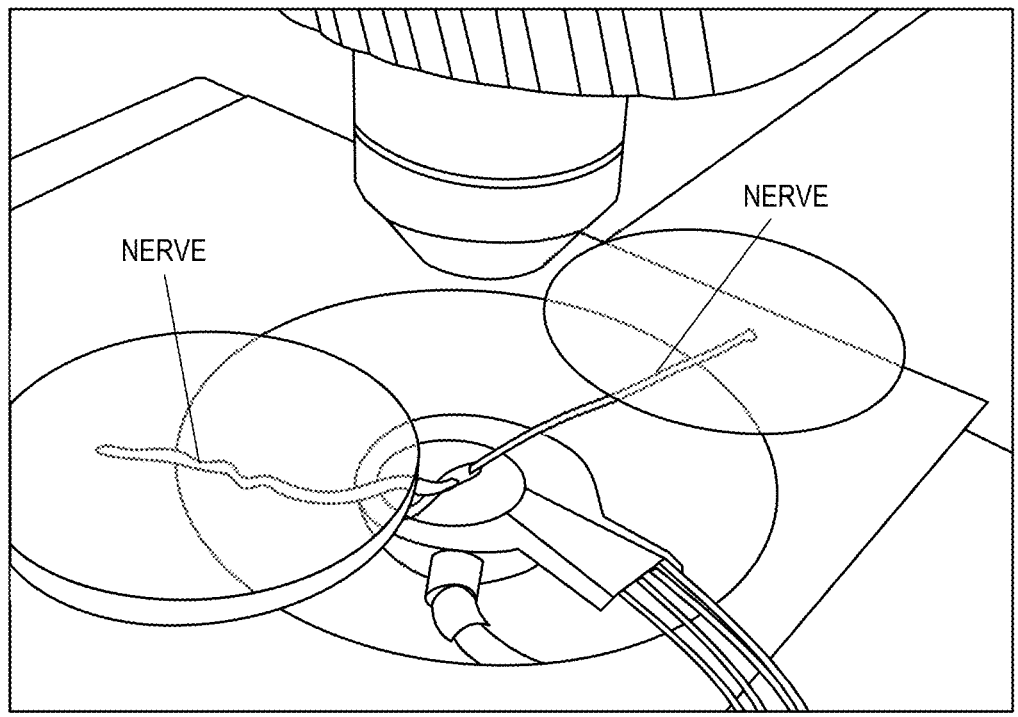
FIG. 10 is a photograph showing a cryostage device for freezing nerves used during examples of the present disclosure.

In the freezing setup, the nerves were laid on a cryostage with freezing and warming stages programmed to provide the temperature profile shown in FIG. 8B. A photograph of the freezing setup used for exposing the nerves to freezing conditions is shown FIG. 10. It was determined that a 5 mm section of the nerves that were in contact with the cooling surface of the cryostage was susceptible to the freezing conditions. Further, temperatures measured by thermocouples or collection leads positioned in proximity to this 5 mm section of the nerves were found to be in good agreement with a temperature indicator on the cryostage. In neural conduction experiments, a frozen region of the nerves was marked and placed between the proximal and distal recording leads Immediately after a freezing step, the nerves were placed in oxygenated Krebs solution at 37° C., and changes in action potential were monitored every 30 minutes for 3 hours. This example aimed to approximate behavior of nerves following acute injury and fast recovery.

Figure 11:
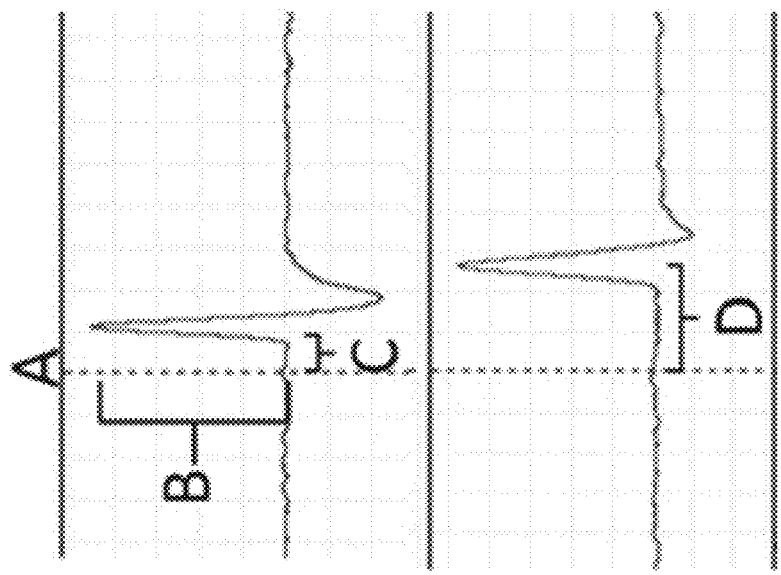
FIG. 11 is a graph showing action potentials measured during testing of nerves.
Figure 12:
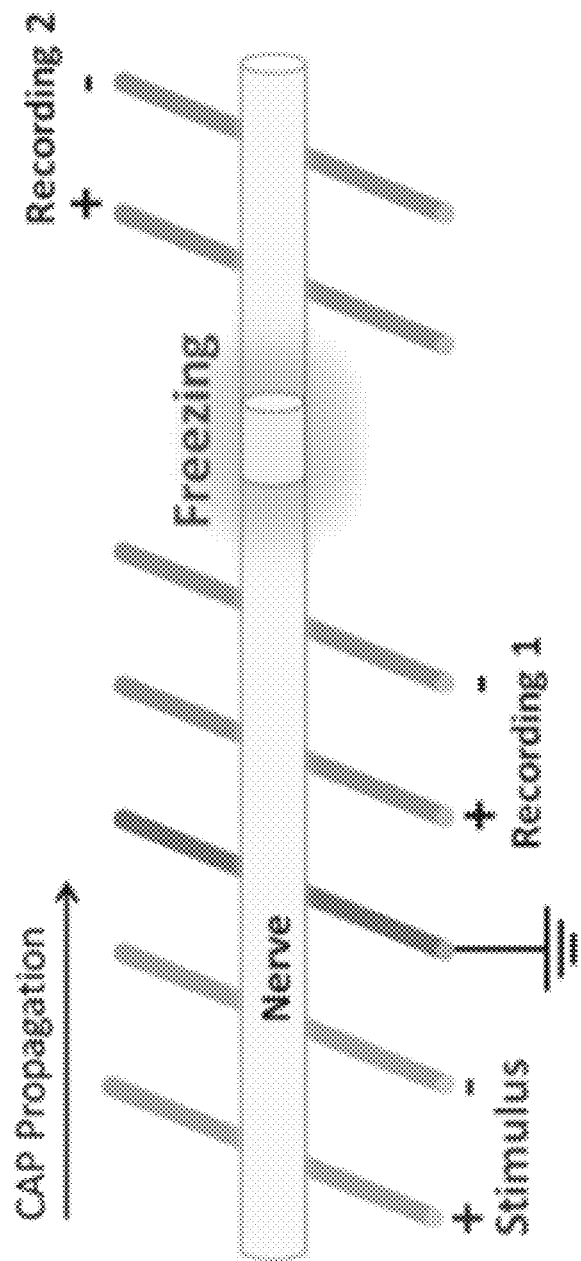
FIG. 12 is a schematic drawing showing an experimental set-up for testing nerves including a frozen section used for examples of the present disclosure.

A schematic diagram showing the experimental setup for testing action potential of the nerves after freezing is shown in FIG. 12. The present inventors believe that impacts of freezing can be quantified by comparing the action potential proximal and distal to the freezing site. In particular, upon stimulation of the nerves, the evoked action potential propagates along the nerves. The action potential can be measured at the proximal leads before reaching the site of injury. Depending on the extent of injury and its recovery, the conduction of the nerves may be completely lost so that no action potential is recorded at the distal leads. However, nerves that are only partially injured or has partially recovered from injury still retains conduction capability, and the action potential can travel past the injury site and be recorded at the distal leads. An example of this comparison is shown by comparing the graphs of FIG. 11, in which the dotted line A indicates the time at which the stimulus was applied, the magnitude B and latency peak C indicate an AP proximal to the freezing site, and the distance D represents the distance traveled by the generated signal through the freezing site. The waveform spike following the distance D indicate the AP following the freezing site.

In the experiments for determining the injury threshold, the nerves were subjected to a variety of freezing conditions consisting of three key parameters—the end temperature, cooling rate, and warming rate. The action potential recovery was measured for each example. Ranges for these three parameters were determined from a series of simulations that cover a wide range of situations during cryosurgery.

Action potential measurements for each example are reported herein as a normalized action potential amplitude. The normalized action potential amplitude (magnitude of the AP at distal leads/magnitude of the AP at proximal leads) is believed to be a key indicator of the continuity of action potential transduction, with 0 indicating complete blockage of the evoked action potential at the freezing site. In addition to the action potential magnitude, an increase in latency (slower conduction speed) and a decrease in voltage gradient (slower depolarization and repolarization of the cells) may also be indicators of injury to the nerves.

Evaluation of Cryoprotectant Agent Toxicity and Freezing Protection

Dissected porcine phrenic nerves and rat sciatic nerves were exposed to a cryoprotectant agent (CPA) containing modified Krebs solution and incubated for 30 min After exposure to the CPA, both porcine phrenic nerves and rat sciatic nerves were subject to the freezing and warming conditions shown in FIG. 8B. After both exposure to the CPA and freezing, recovery of the evoked AP in the nerves is monitored for 3 hours.

Four categories of cryoprotectant agents were evaluated and compared: (1) conventional DMSO-based cryoprotectant agents, (2) modified DMSO-based cryoprotectant agents developed with the goal of reducing the usage of DMSO, (3) branded cryoprotectant agents used in the cryopreservation of cells, tissue, and organs, and (4) alcohol (and their derivatives) based cryoprotectant agents that are free of DMSO. Experimental results for the most promising cryoprotectant agents are reported herein and shown in FIGS. 13A-18.

Figures 13A, 13B:
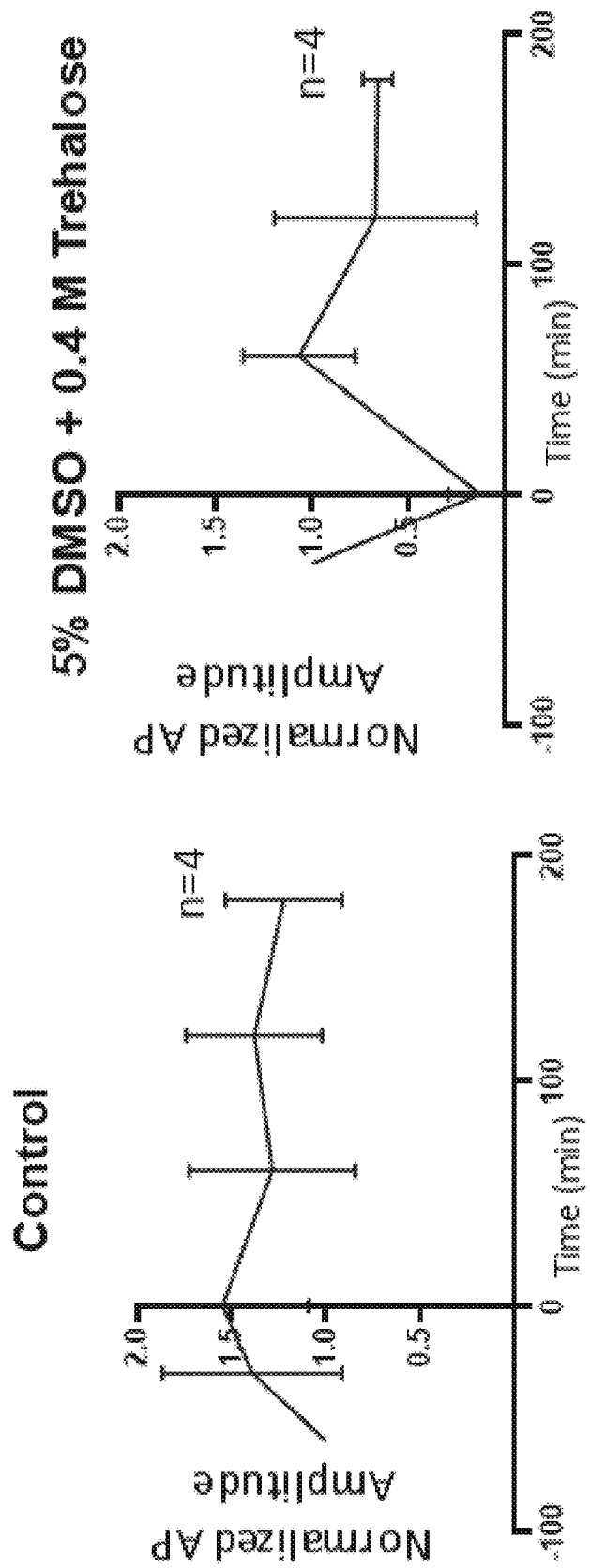
FIGS. 13A-13F are graphs showing experimental results for testing of a cryoprotectant agent on phrenic nerves of a swine.
Figures 13C, 13D:
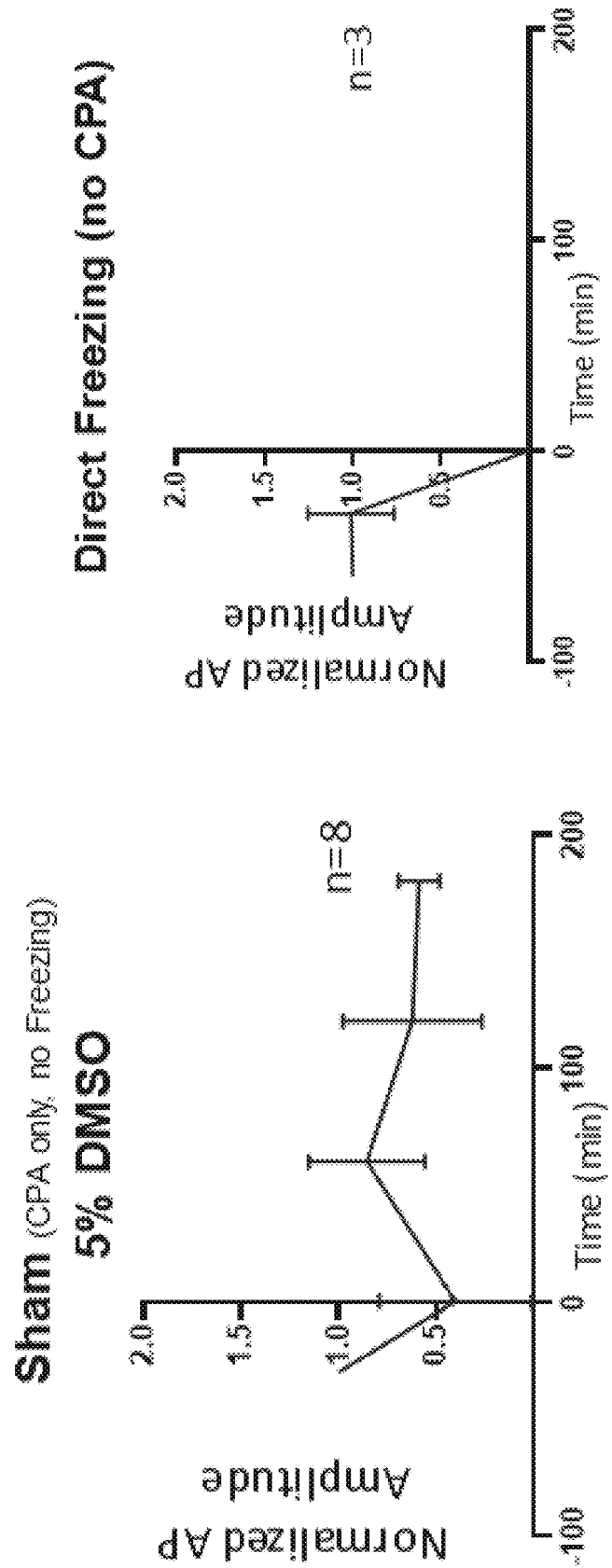
Figure 13F:
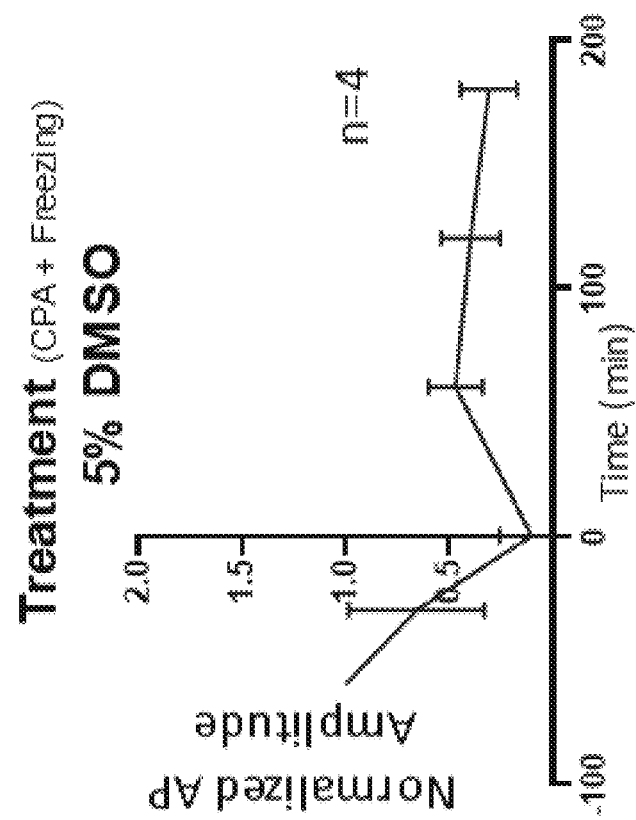
Figure 13E:
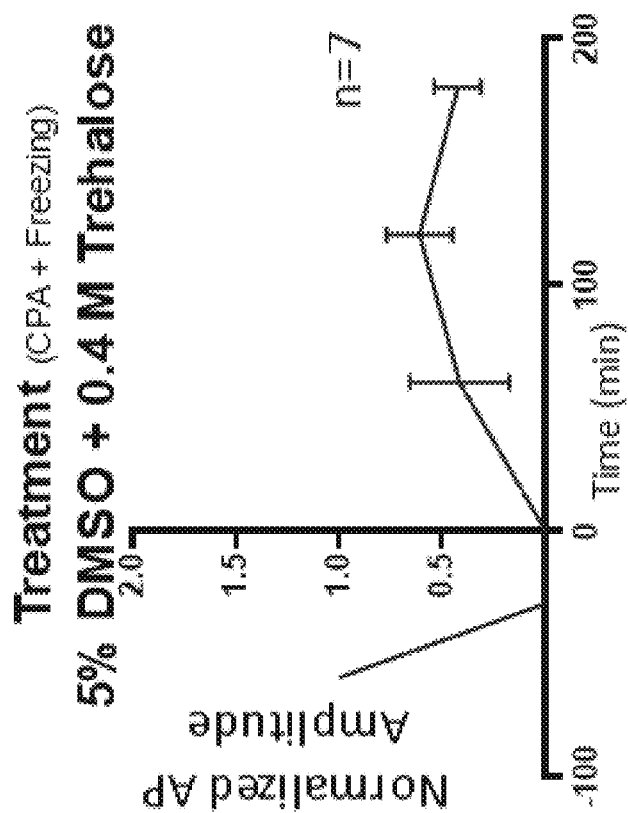

Experimental results for phrenic nerve CPA toxicity testing are shown in FIGS. 13A-13F, which are graphs showing changes in normalized action potential over time for different cryoprotectant agents (both with and without freezing). FIGS. 13A-13C show effects of exposing the phrenic nerves to CPA without freezing. Specifically, FIG. 13A shows a control, where no CPA was applied to the phrenic nerves; FIG. 13B shows exposure of the phrenic nerves to a CPA solution of 5% DMSO+0.4M Trehalose; and FIG. 13C shows exposure of the nerves to a CPA solution of 5% DMSO. FIGS. 13D-13F show effects of both freezing and exposure of the phrenic nerves to the CPA. Specifically, FIG. 13D shows a control in which the phrenic nerves are frozen without being exposed to the CPA solution; FIG. 13E shows effects of freezing and exposure to a CPA solution of 5% DMSO and 0.4 M Trehalose for the phrenic nerves; and FIG. 13F shows effects of freezing and exposure to a CPA solution of 5% DMSO. Normalized action potential values for other cryoprotectant agents are shown in Table 1, as follows.

TABLE 1

Effect of cryoprotectant agent (CPA) on the phrenic nerves

| | # of nerves with >30% AP Recovery at 180 min | | |
|---|---|---|---|
| | CPA Exposure | w/ Freezing | Averaged normalized AP amplitude at 180 min |
| 5% DMSO and 0.2M Trehalose | 6/6 | 3/4 | 0.48 |
| 5% DMSO and 0.4M Trehalose | 4/4 | 6/7 | 0.42 |
| 10% ethylene glycol (EG) and Sucrose | 3/3 | 2/4 | 0.23 |
| 5% DMSO | 4/4 | 1/4 | 0.31 |
| 5% M22 | 3/3 | 0/3 | 0.13 |
| 0.4 M Trehalose | 4/4 | 1/4 | 0.25 |
| 10% DMSO | 4/4 | 0/4 | 0.11 |
| 10% propylene glycol (PG) | 3/3 | 2/5 | 0.1 |
| 10% ethylene glycol (EG) | 3/3 | 0/4 | 0 |

Figures 14A, 14B:
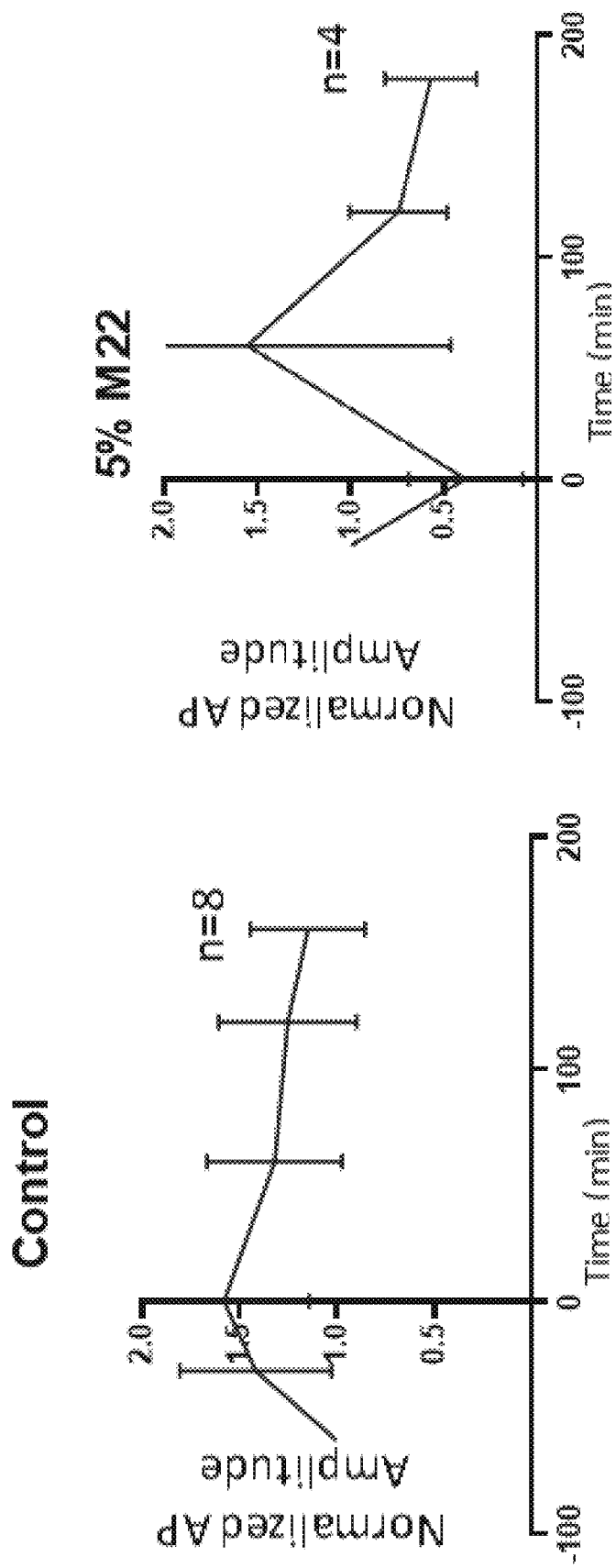
FIGS. 14A-14F are graphs showing experimental results for testing of a cryoprotectant agent on sciatic nerves of a rat.
Figures 14C, 14D:
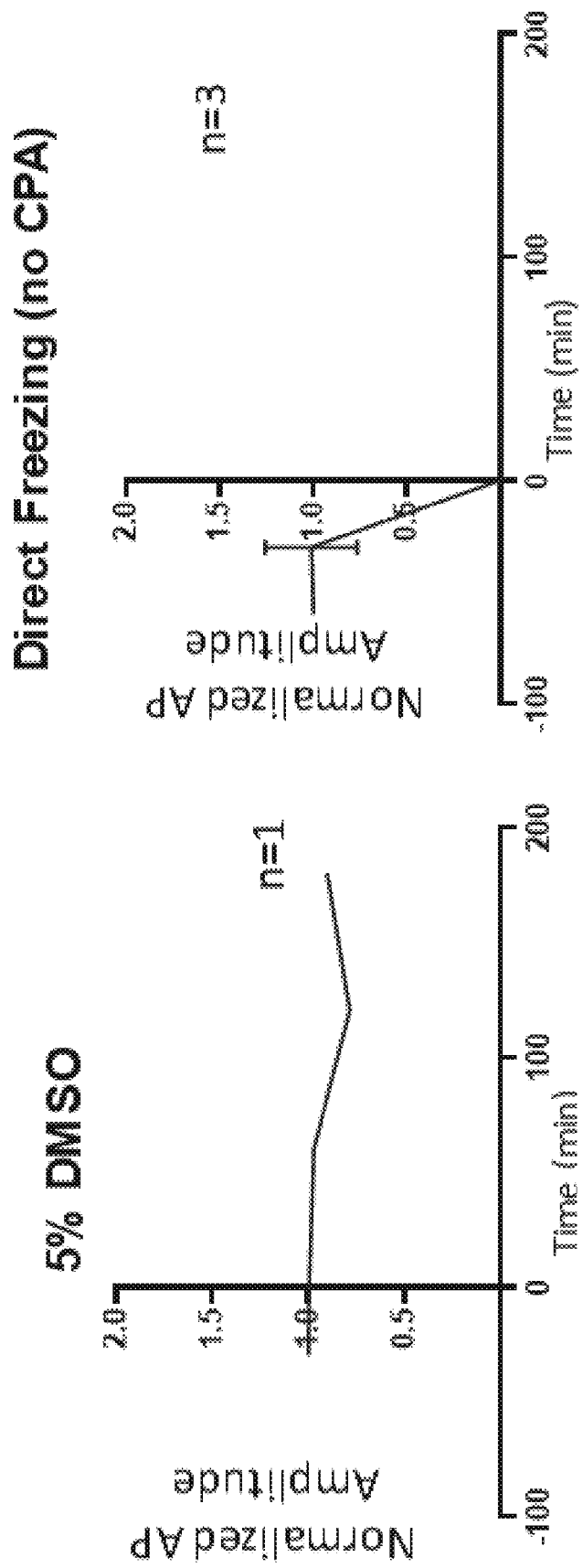
Figures 14E, 14F:
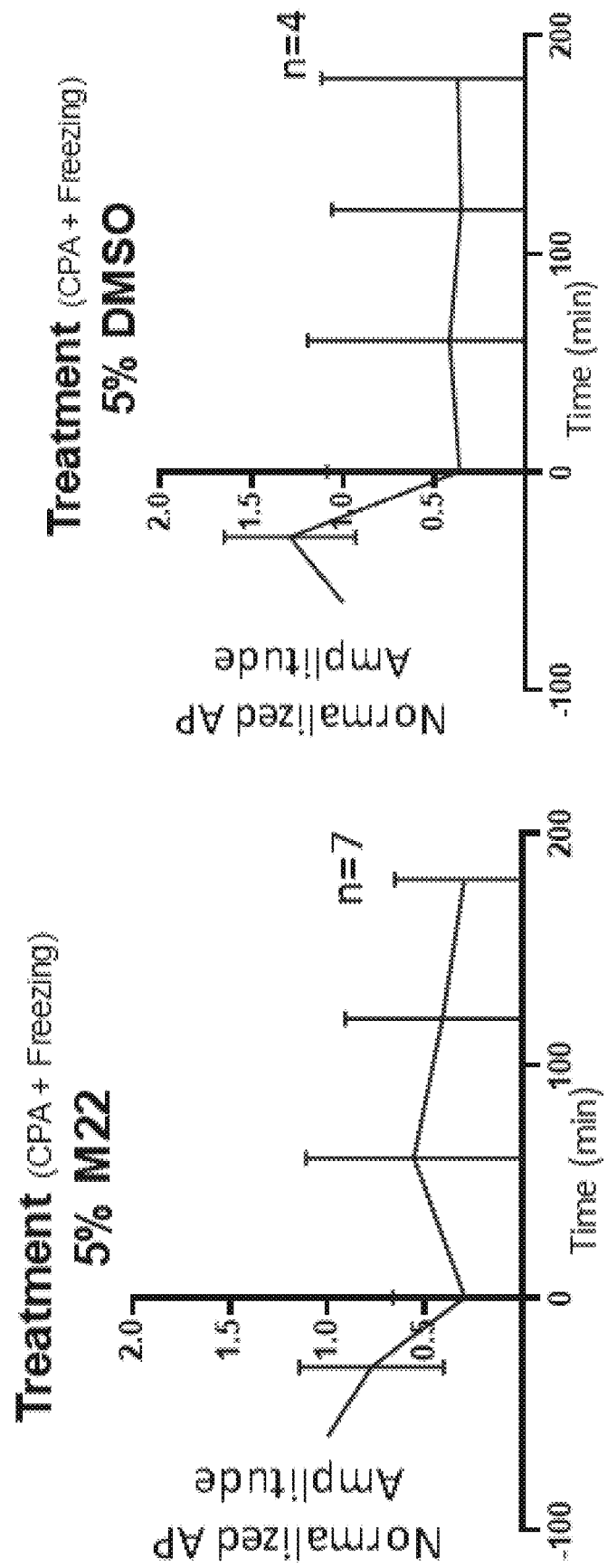

Experimental results for sciatic nerve CPA toxicity testing are shown in FIGS. 14A-14F. FIGS. 14A-14C show effects of exposing the sciatic nerves of a rat to CPA without freezing. Specifically, FIG. 14A shows a control, where no CPA was applied to the sciatic nerves; FIG. 14B shows exposure of the sciatic nerves to a CPA solution of 5% M22; and FIG. 14C shows exposure of the sciatic nerves to a CPA solution of 5% DMSO. FIGS. 14D-14F show effects of freezing and exposure to the CPA for the sciatic nerves. Specifically, FIG. 14D shows a control in which the sciatic nerves are frozen without being exposed to the CPA solution; FIG. 14E shows effects of freezing and exposing the sciatic nerves to a CPA solution of 5% M22; and FIG. 14F shows effects of freezing and exposure to a CPA solution of 5% DMSO. Normalized action potential values for other cryoprotectant agents are shown in Table 2, as follows.

TABLE 2

Effects of cryoprotectant agent (CPA) on the sciatic nerves

| | # of nerves with >30% AP Recovery at 180 min | | |
|---|---|---|---|
| | CPA Exposure | w/ Freezing | Averaged normalized AP amplitude at 180 min |
| 5% M22 | 3/4 | 4/7 | 0.3 |
| 5% DMSO | 3/3 | 1/4 | 0.37 |
| 10% DMSO | 3/3 | 0/7 | 0.11 |
| 15% DMSO | 3/5 | 0/3 | 0 |
| 5% DMSO + 0.2M Trehalose | 4/4 | 0/4 | 0 |

As shown in FIGS. 13D and 14D, the phrenic nerves and the sciatic nerves do not present any detectable AP after freezing. As shown by comparing FIG. 13A with FIGS. 13B and 13C (also by comparing FIG. 14A with FIGS. 14B and 14C), applying the CPA solution to the nerves reduced the action potential compared to when no CPA was present. As shown by comparing FIG. 13D with FIGS. 13E and 13F (also by comparing FIG. 14D with FIGS. 14E and 14F), applying the CPA solution to the nerves protected the nerves from freezing so that a detectable AP was observed following freezing when the nerves were exposed to the CPA composition.

Figure 15A:
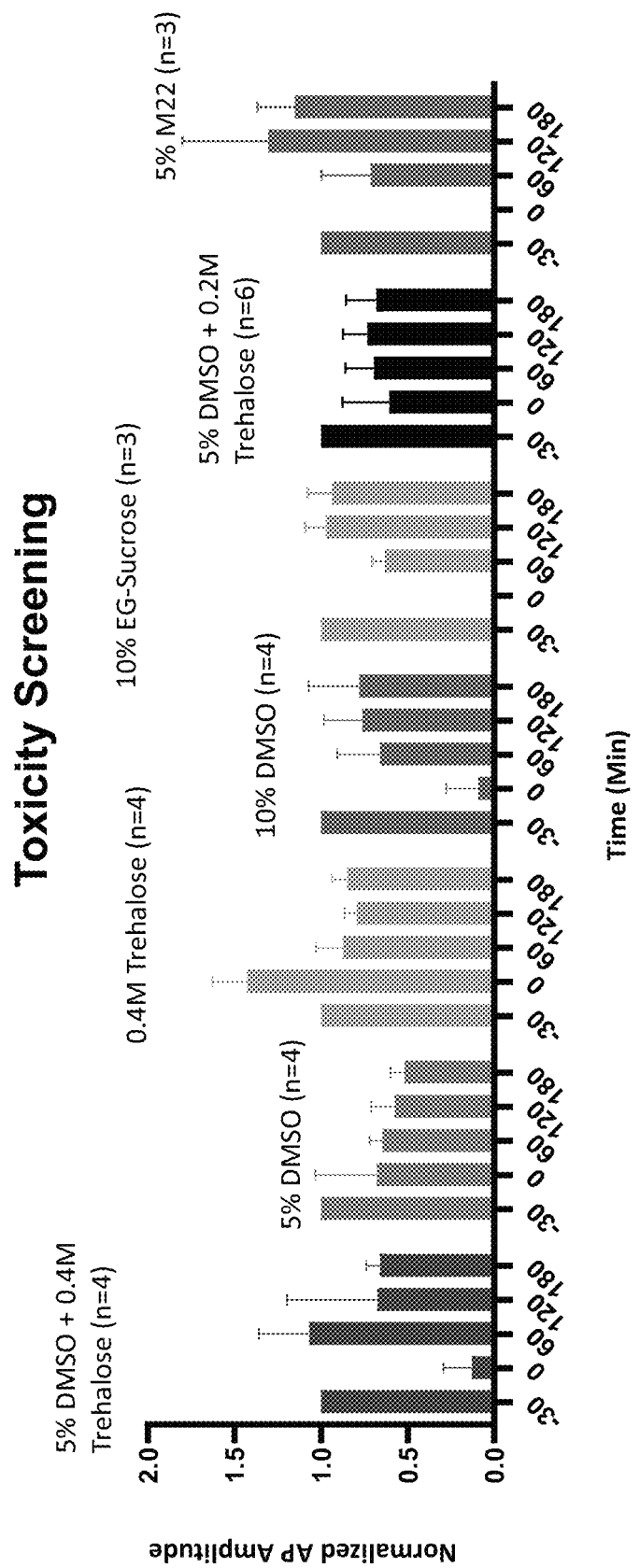
FIGS. 15A-15C are graphs showing additional experimental results for testing of a cryoprotectant agent on phrenic nerves of a swine.
Figure 15B:
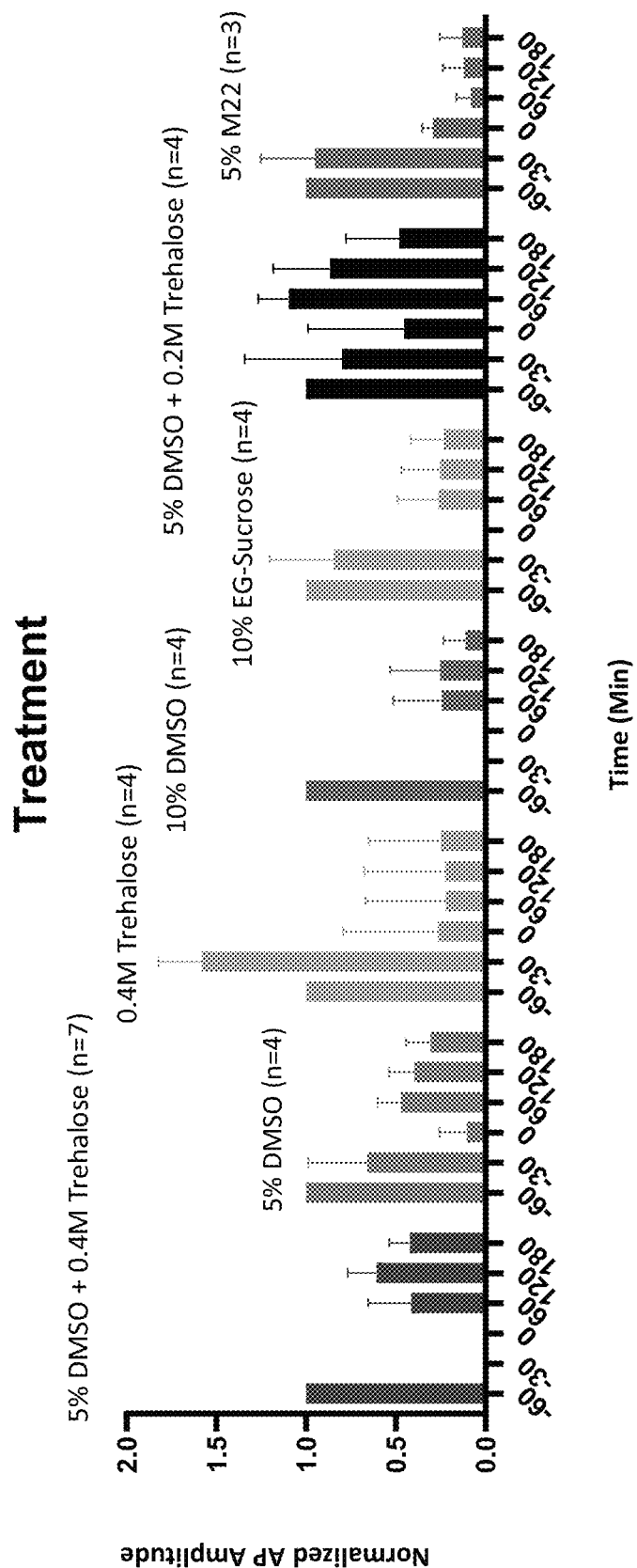
Figure 15C:
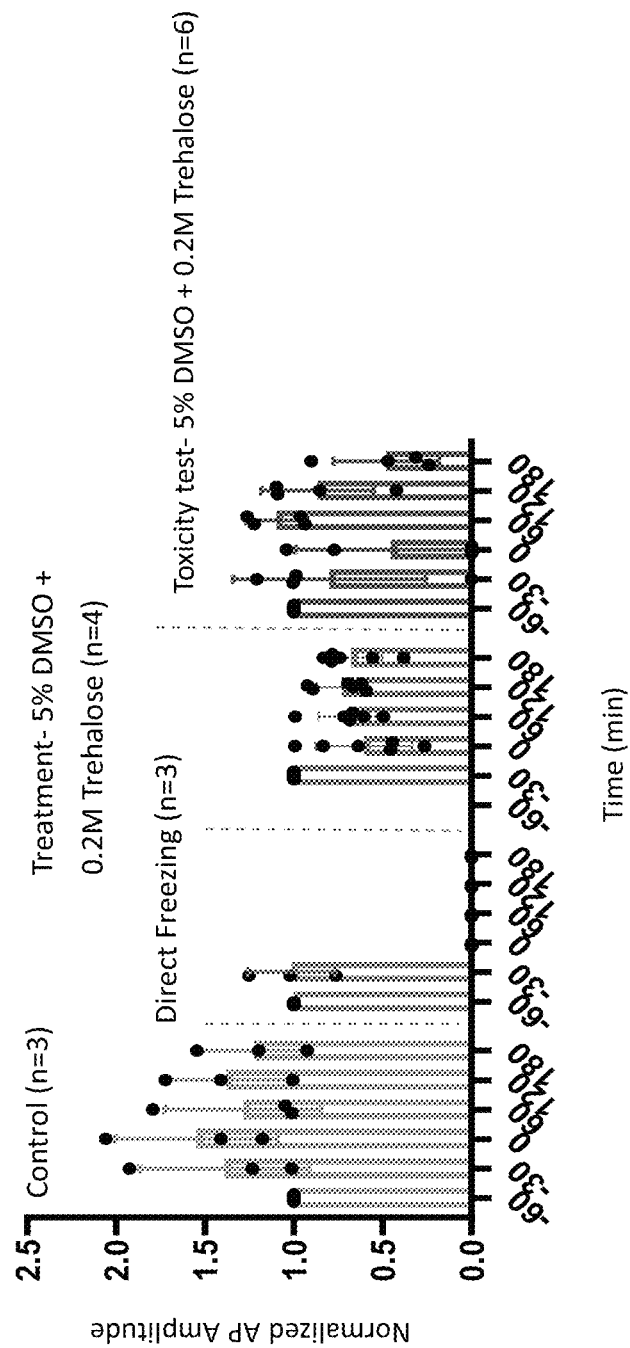

FIGS. 15A-15C show effects of the CPA and freezing on the phrenic nerves over time. FIG. 15A shows results for a toxicity screening in which the nerves were exposed to CPA without freezing. AP amplitude prior to exposure to CPA (−30 minutes), at exposure to CPA (0 minutes), and 60 minutes, 120 minutes, and 180 minutes following exposure to the CPA for the porcine phrenic nerves. The CPAs tested were: 5% DMSO+0.4M Trehalose; 5% DMSO; 0.4M Trehalose; 10% DMSO; 10% EG-Sucrose; 5% DMSO+0.2M Trehalose; and 5% M22. FIG. 15B shows AP amplitude over time for the phrenic nerves for a treatment screening with the nerves exposed to both the CPA solution and to freezing for the following CPA solutions: 5% DMSO+0.4M Trehalose; 5% DMSO; 0.4M Trehalose; 10% DMSO; 10% EG-Sucrose; 5% DMSO+0.2M Trehalose; and 5% M22. FIG. 15C shows a comparison between a control (no CPA or freezing), direct freezing, toxicity, and treatment for 5% DMSO+0.2M Trehalose.

Figure 16A:
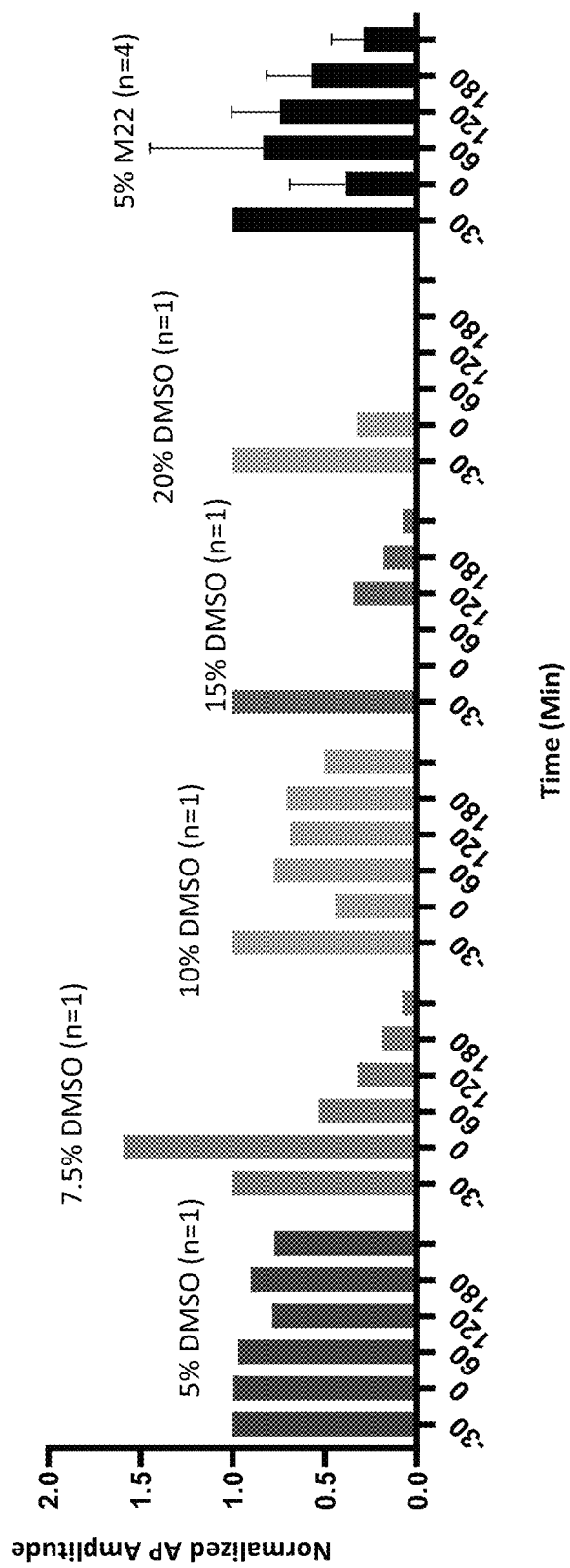
FIGS. 16A-16C are graphs showing additional experimental results for testing of a cryoprotectant agent on sciatic nerves of a rat.
Figure 16B:
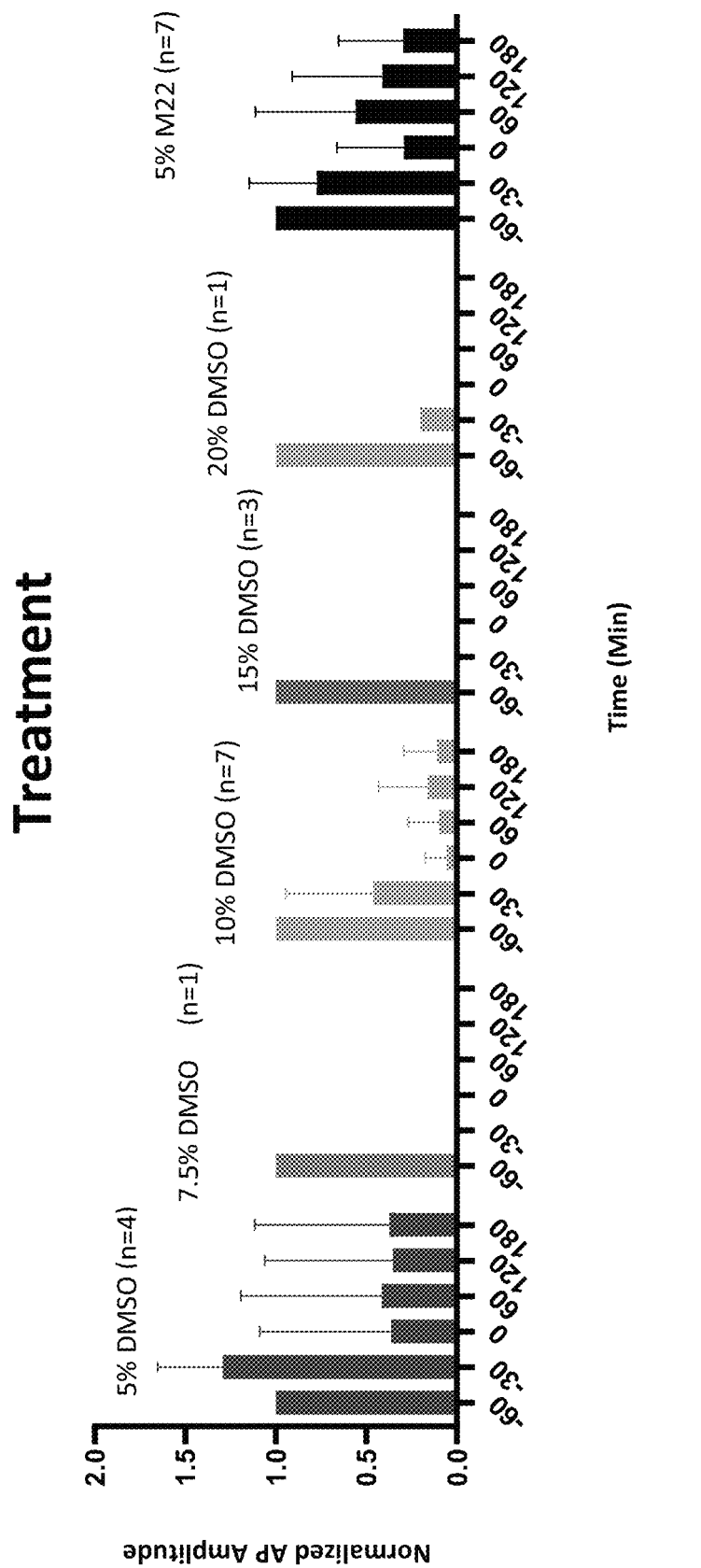
Figure 16C:
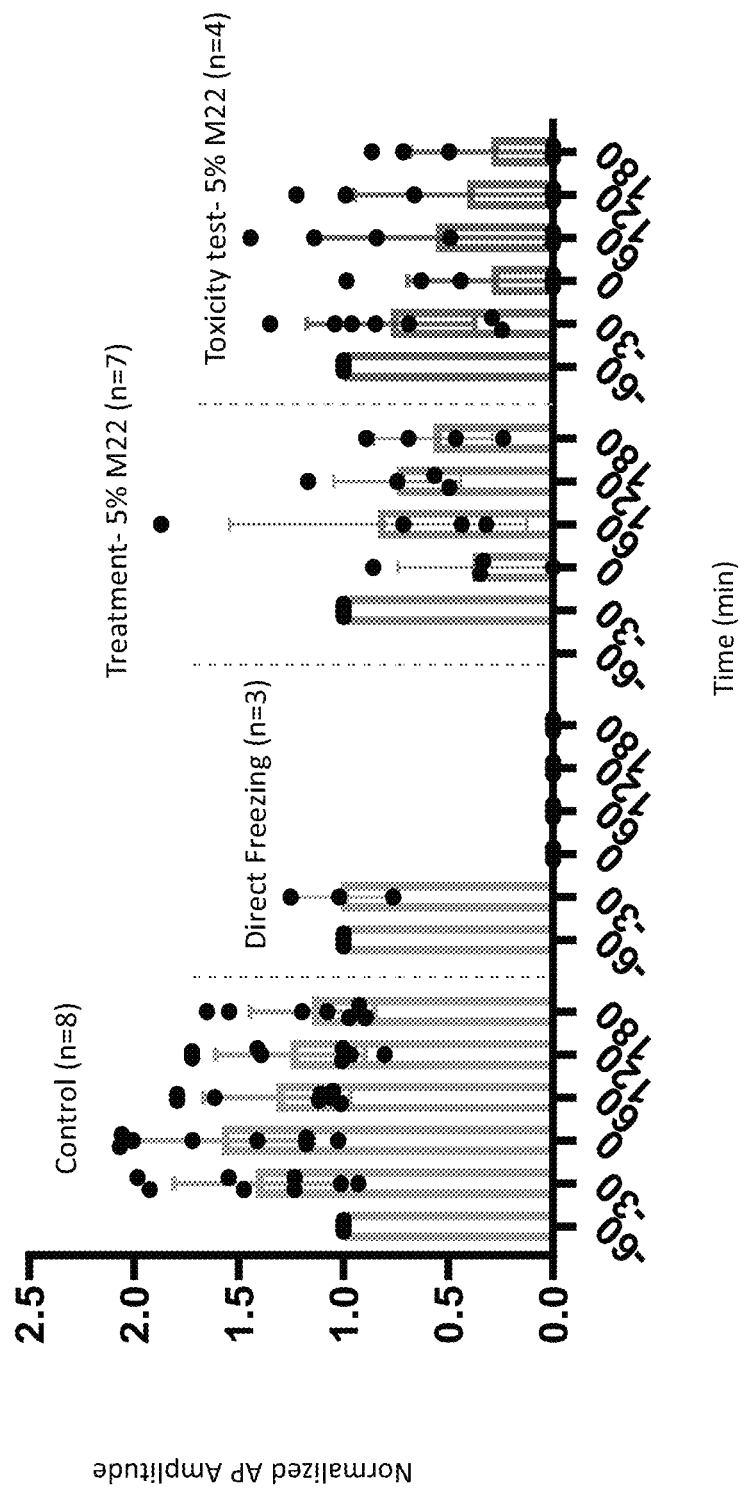

FIGS. 16A and 16B show effects of the CPA and freezing on the sciatic nerves over time. FIG. 16A shows AP amplitude prior to exposure to CPA (−30 minutes), at exposure to CPA (0 minutes), and 60 minutes, 120 minutes, and 180 minutes following exposure to the CPA for the rat sciatic nerves. FIG. 16B shows AP amplitude over time for the sciatic nerves exposed to both the CPA solution and to freezing. The CPAs tested were 5% DMSO, 7.5% DMSO, 10% DMSO, 15% DMSO, 20% DMSO, and 5% M22. FIG. 16C shows a comparison between a control (no CPA or freezing), direct freezing, toxicity, and treatment for 5% M22.

Figures 17A, 17B:
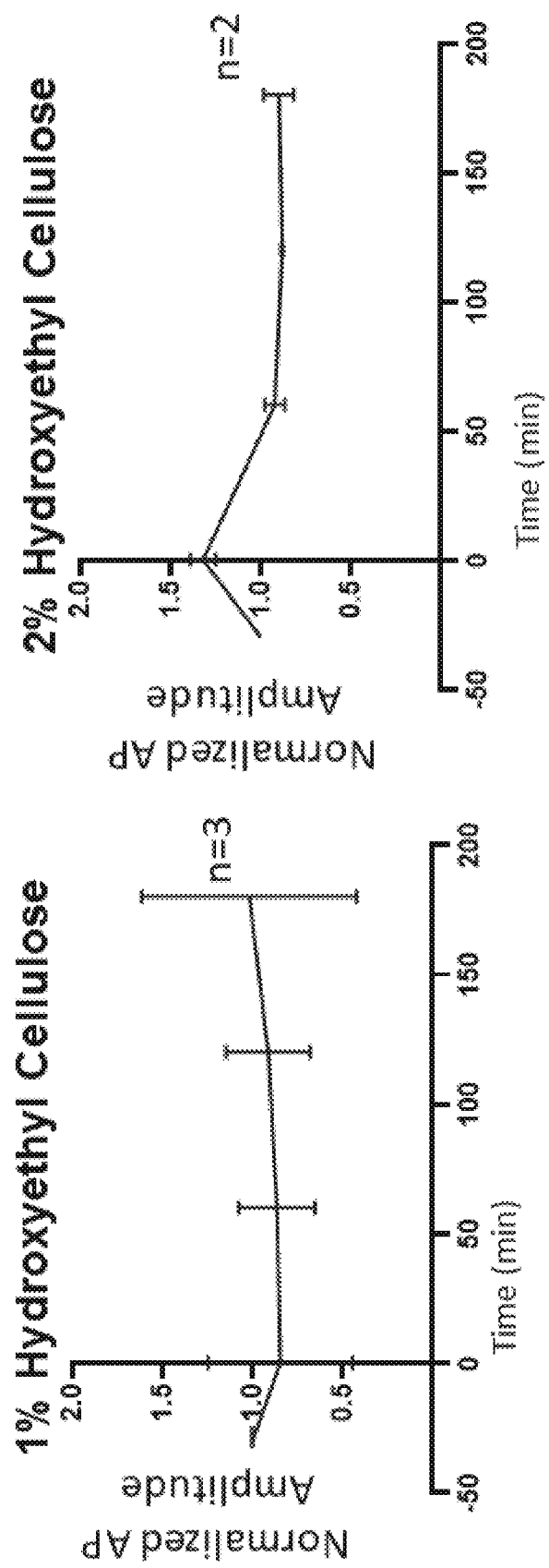
FIGS. 17A-17D are graphs showing experimental results for toxicity testing of hydroxyethyl cellulose.
Figures 17C, 17D:
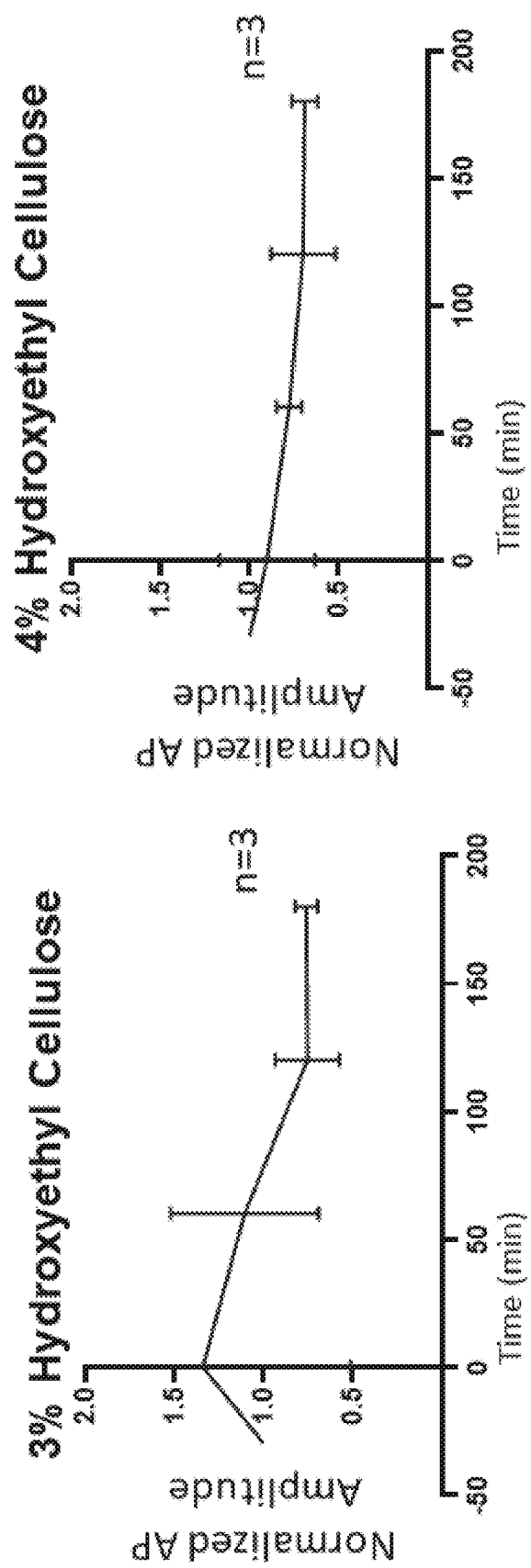

As previously described, the cryoprotective composition can comprise a fluid agent, such as a gel, that increases the viscosity of the composition. In some examples, the fluid agent comprises cellulose, such as hydroxyethyl cellulose. FIGS. 17A-17D show experimental results for toxicity tests for a composition comprising 1% hydroxyethyl cellulose (FIG. 17A), 2% hydroxyethyl cellulose (FIG. 17B), 3% hydroxyethyl cellulose (FIG. 17C), or 4% hydroxyethyl cellulose (FIG. 17D). In each case, an action potential was observed for the nerves following exposure to the composition comprising hydroxyethyl cellulose.

Figure 18:
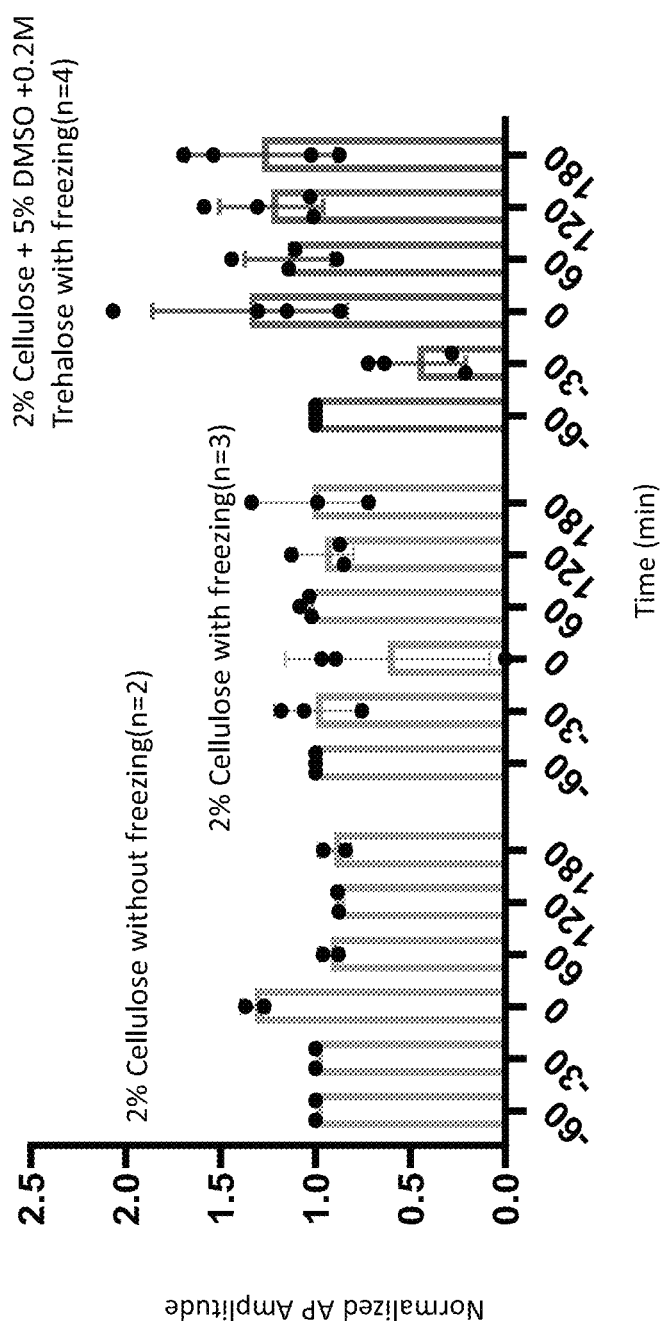
FIG. 18 is a graph showing experimental results for toxicity and freezing testing of a cryoprotective composition including cellulose and a cryoprotectant agent, according to an example of the present disclosure.

FIG. 18 shows effects of a composition comprising a gel (e.g., hydroxyethyl cellulose) in combination with a cryoprotectant agent. Specifically, FIG. 18 compares the normalized action potentials over time for 2% hydroxyethyl cellulose without freezing (left side of FIG. 18), 2% hydroxyethyl cellulose with freezing (middle of FIG. 18), and 2% hydroxyethyl cellulose, 5% DMSO, and 0.2M Trehalose (right side of FIG. 18). As shown in FIG. 18, each example including the 2% hydroxyethyl cellulose composition generated action potentials, indicating that 2% hydroxyethyl cellulose is not toxic for the phrenic nerve cells. Further, the averaged normalized AP amplitude over 180 minutes (as shown in following Table 3) for a composition with 2% hydroxyethyl cellulose alone was found to be 1.02. In contrast, the averaged normalized AP amplitude over 180 minutes for the composition of 2% hydroxyethyl cellulose, 5% DMSO, and 0.2M Trehalose was 1.3, indicating that addition of the cryoprotectant agent increased action potential amplitude compared to when no cryoprotectant agent was present.

TABLE 3

Effect of gel/CPA on the phrenic nerves

| | # with >50% AP Recovery at 180 min | | |
|---|---|---|---|
| | CPA Exposure | With Freezing | Averaged normalized AP amplitude at 180 min |
| 2% Hydroxyethyl cellulose | 2/2 | 3/3 | 1.02 |
| 2% Hydroxyethyl cellulose + 5% DMSO + 0.2M Trehalose | 3/3 | 4/4 | 1.3 |

Figure 19B:
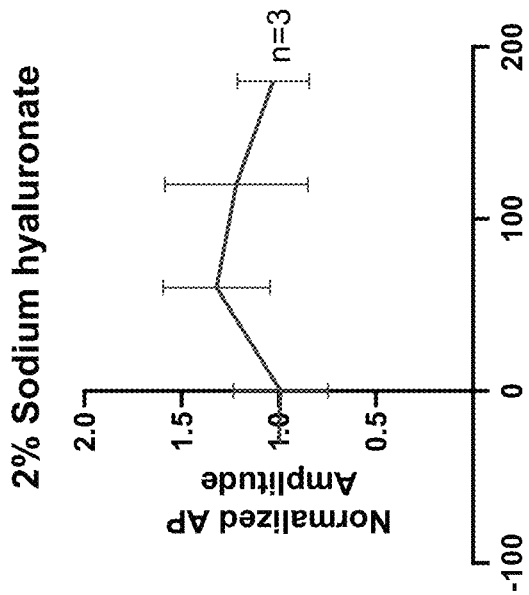
FIGS. 19A and 19B are graphs showing experimental results for toxicity testing of sodium hyaluronate.
Figure 19A:
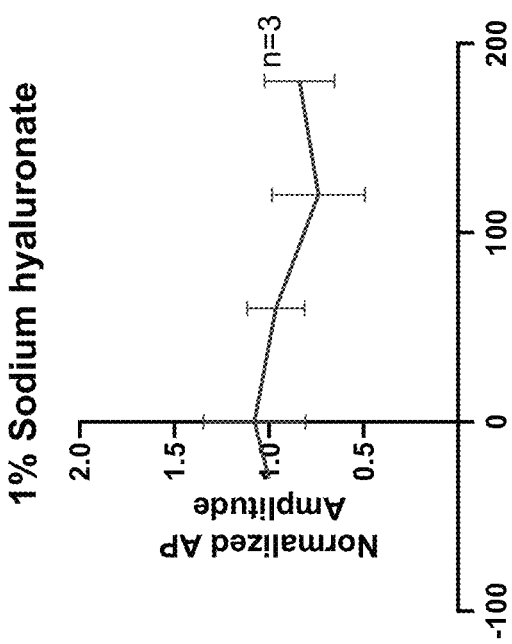
Figure 19C:
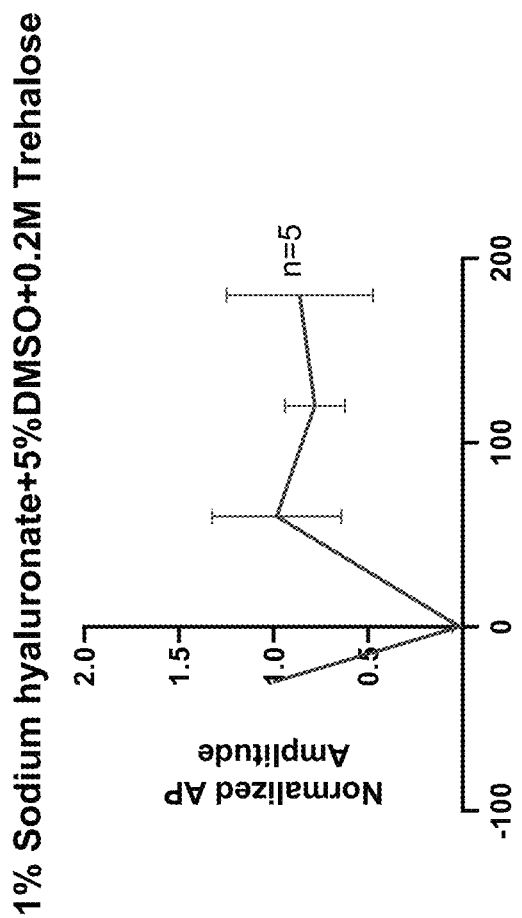
FIG. 19C is a graph showing experimental results for toxicity testing of a composition of sodium hyaluronate, DMSO, and trehalose.

As previously discussed, another example of a gel-like fluid agent, which can be used with the cryoprotective composition of the present disclosure, is a hyaluronic acid composition, such as sodium hyaluronate. FIGS. 19A and 19B show experimental results for toxicity tests for a composition comprising 1% sodium hyaluronate (FIG. 19A) and 2% sodium hyaluronate (FIG. 19B). In each case, an action potential was observed for the nerves following exposure to the composition comprising the sodium hyaluronate. FIG. 19C shows experimental results for toxicity tests for a composition comprising 1% sodium hyaluronate, 5% DMSO, and 0.2M trehalose. An action potential was also observed for the nerves following exposure to this composition, which indicates that the composition has low toxicity or at least that addition of sodium hyaluronate does not substantially modify toxicity of a composition comprising 5% DMSO and 0.2M trehalose.

The preceding examples and embodiments of the invention have been described with reference to various examples. Modifications and alterations will occur to others upon reading and understanding the foregoing examples. Accordingly, the foregoing examples are not to be construed as limiting the disclosure.

What is claimed is:

1. A method of protecting a surgical site during prostate cryosurgery comprising injecting a therapeutically effective amount of a cryoprotective composition into a periprostatic space surrounding a neurovascular bundle (NVB) adjacent to a prostate of a patient in proximity to the cryosurgery in order to separate the NVB from the surgical site
   wherein the cryoprotective composition comprises:
      at least one biodegradable and/or bioerodible fluid agent comprising a gel comprising from about 1 weight percent to about 10 weight percent of the cryoprotective composition; and
      at least one non-toxic cryoprotectant agent contained in the gel, the at least one non-toxic cryoprotectant agent comprising Dimethyl sulfoxide (DMSO) and trehalose,
   wherein the therapeutically effective amount of the cryoprotective composition deposited in the periprostatic space remains within at least a portion of the periprostatic space for a duration of the cryosurgery in order to maintain separation of the body tissue to be protected from the surgical site for the duration of the cryosurgery, and
   wherein a majority of nerves of the NVB remain viable when exposed to a temperature of negative 10° C. during the cryosurgery and with the majority of the nerves having at least about a 30% action potential recovery following the cryosurgery.

2. The method of claim 1, wherein the at least one non-toxic cryoprotectant agent comprises from about 1 weight percent to about 10 weight percent of the cryoprotective composition.

3. The method of claim 1, wherein the at least one non-toxic cryoprotectant agent comprises Dimethyl sulfoxide (DMSO) comprising from about 1 weight percent to about 5 weight percent of the cryoprotective composition.

4. The method of claim 1, wherein the at least one non-toxic cryoprotectant agent is free of ethylene glycol.

5. The method of claim 1, wherein the duration of the cryosurgery is from about 10 minutes to about 5 hours.

6. The method of claim 1, wherein the at least one non-toxic cryoprotectant agent causes less than about a 30% decrease of viability compared to saline and/or causes less than a 30% decrease of action potential amplitude compared to Krebs solution.

7. The method of claim 1, wherein the cryoprotective composition does not cause substantial nerve damage when positioned in the periprostatic space for the duration of the cryosurgery.

8. The method of claim 1, wherein the cryoprotective composition inhibits freezing and/or crystallization of the NVB and surrounding body tissue proximate to the periprostatic space when cryotherapy agents are used for the cryosurgery.

9. The method of claim 1, wherein the therapeutically effective amount of the cryoprotective composition comprises an amount of the cryoprotective composition sufficient to inhibit freezing and/or crystallization of the NVB and surrounding tissue proximate to the periprostatic space when cryotherapy agents are used for the cryosurgery.

10. The method of claim 1, wherein, when applied to the NVB of the patient, the cryoprotective composition does not substantially inhibit generation of action potentials by nerves of the NVB.

11. The method of claim 1, wherein the cryoprotective composition further comprises at least one of Krebs phosphate solution or phosphate-buffered saline.

12. The method of claim 1, wherein the at least one biodegradable and/or bioerodible fluid agent comprises at least one of cellulose and/or hyaluronic acid.

13. The method of claim 1, wherein the at least one non-toxic cryoprotectant agent comprises Dimethyl sulfoxide (DMSO) comprising from about 1 weight percent to about 5 weight percent of the cryoprotective composition, and
wherein the at least one biodegradable and/or bioerodible fluid agent comprises hydroxyethyl cellulose comprising from about 1 weight percent to about 4 weight percent of the cryoprotective composition.

14. The method of claim 1, wherein the at least one non-toxic cryoprotectant agent comprises Dimethyl sulfoxide (DMSO) comprising from about 1 weight percent to about 5 weight percent of the cryoprotective composition and from about 0.2M to about 0.4M trehalose, and
wherein the at least one biodegradable and/or bioerodible fluid agent comprises hydroxyethyl cellulose comprising from about 1 weight percent to about 4 weight percent of the cryoprotective composition.

15. The method of claim 1, wherein the at least one non-toxic cryoprotectant agent comprises Dimethyl sulfoxide (DMSO) comprising about 5 weight percent of the cryoprotective composition and about 0.2M trehalose, and
wherein the at least one biodegradable and/or bioerodible fluid agent comprises hydroxyethyl cellulose comprising from about 1 weight percent to about 4 weight percent of the cryoprotective composition.

16. The method of claim 1, wherein the at least one non-toxic cryoprotectant agent comprises Dimethyl sulfoxide (DMSO) comprising from about 1 weight percent to about 5 weight percent of the cryoprotective composition and from about 0.2M to about 0.4M trehalose, and
wherein the at least one biodegradable and/or bioerodible fluid agent comprises hyaluronic acid comprising from about 1 weight percent to about 4 weight percent of the cryoprotective composition.

17. The method of claim 1, wherein the at least one non-toxic cryoprotectant agent comprises Dimethyl sulfoxide (DMSO) comprising about 5 weight percent of the cryoprotective composition and about 0.2M trehalose, and
wherein the at least one biodegradable and/or bioerodible fluid agent comprises hyaluronic acid comprising from about 1 weight percent to about 2 weight percent of the cryoprotective composition.

18. The method of claim 1, wherein a size of a needle used for the injection of the cryoprotective composition into the periprostatic space ranges from an 18 gauge needle to a 22 gauge needle.

19. The method of claim 18, wherein the injection is performed with ultrasound visualization of the needle and the periprostatic space with the patient in a lithotomy position.

20. The method of claim 19, wherein the ultrasound visualization is provided by a transrectal ultrasound.

21. The method of claim 1, wherein the injection of the cryoprotective composition to the periprostatic space comprises:
inserting a tip of a syringe needle through a perineum of the patient,
under ultrasound guidance, advancing the tip of the needle from an insertion site in the perineum to perforate a Denonvillier's fascia of the periprostatic space distal to the prostate,
injecting a first amount of the cryoprotective composition to a portion of the periprostatic space between the prostate and rectum, thereby separating a portion of the prostate comprising the surgical site from the rectum, and
continuing to inject the cryoprotective composition from the tip of the needle while retracting the needle from a base of the prostate to an apex of the prostate.

22. The method of claim 21, wherein the injection of the cryoprotective composition to the periprostatic space further comprises injecting a second amount of the cryoprotective composition to spaces surrounding the NVB adjacent to the prostate, thereby separating the portion of the prostate comprising the surgical site from the NVB.

23. The method of claim 1, wherein the cryoprotective composition is injected into the periprostatic space between a base of the prostate and an apex of the prostate.

24. The method of claim 1, wherein the injected cryoprotective composition substantially or fully envelops the NVB of the patient adjacent to the prostate.

25. The method of claim 1, wherein the cryosurgical procedure comprises tumor ablation of a prostate tumor.

26. The method of claim 1, wherein the gel has a viscosity at about 20° C. to about 25° C. suitable to be ejected from a needle cannula into the body space.

27. The method of claim 1, wherein the at least one biodegradable and/or bioerodible fluid agent remains as a gel at the temperature of negative 10° C.

* * * * *

UNITED STATES PATENT AND TRADEMARK OFFICE
CERTIFICATE OF CORRECTION

PATENT NO. : 12,426,594 B2  
APPLICATION NO. : 17/482898  
DATED : September 30, 2025  
INVENTOR(S) : Franz Schmidlin et al.

Page 1 of 1

It is certified that error appears in the above-identified patent and that said Letters Patent is hereby corrected as shown below:

On the Title Page

Column 1, item (71) Applicants, Line 2, delete "Zug (CH)" and insert -- Baar (CH) --

Column 1, item (73) Assignees, Line 2, delete "Zug (CH)" and insert -- Baar (CH) --

Signed and Sealed this  
Ninth Day of December, 2025

John A. Squires  
*Director of the United States Patent and Trademark Office*